(12) United States Patent
Lewkonya et al.

(10) Patent No.: US 10,850,044 B2
(45) Date of Patent: Dec. 1, 2020

(54) SAFE AUTO-NEEDLE DEVICE

(71) Applicant: DALI MEDICAL DEVICES LTD., Yavne (IL)

(72) Inventors: Gad Lewkonya, Neve Mivtach (IL); Ehoud Carmel, Yehud-Monson (IL); David Daily, Herzlia (IL); Lior Raday, Hof Ashkelon (IL); Hagay Drori, Tel Aviv-Jaffa (IL)

(73) Assignee: DALI MEDICAL DEVICES LTD., Yavne (IL)

( * ) Notice: Subject to any disclaimer, the term of this patent is extended or adjusted under 35 U.S.C. 154(b) by 0 days.

(21) Appl. No.: 15/669,987

(22) PCT Filed: Feb. 10, 2016

(86) PCT No.: PCT/IL2016/050160
§ 371 (c)(1),
(2) Date: Aug. 7, 2017

(87) PCT Pub. No.: WO2016/128977
PCT Pub. Date: Aug. 18, 2016

(65) Prior Publication Data
US 2017/0354791 A1    Dec. 14, 2017

Related U.S. Application Data

(60) Provisional application No. 62/114,095, filed on Feb. 10, 2015.

(51) Int. Cl.
*A61M 5/32* (2006.01)
*A61M 5/20* (2006.01)
(Continued)

(52) U.S. Cl.
CPC ............ *A61M 5/3204* (2013.01); *A61M 5/20* (2013.01); *A61M 5/2033* (2013.01);
(Continued)

(58) Field of Classification Search
CPC .... A61M 5/2033; A61M 5/24; A61M 5/3243; A61M 5/326; A61M 5/3287;
(Continued)

(56) References Cited

U.S. PATENT DOCUMENTS 4,367,738 A * 1/1983 Legendre ............ A61M 5/5013
                                                            604/110
6,685,676 B2  2/2004 Jansen et al.
(Continued)

FOREIGN PATENT DOCUMENTS

WO    2014037946 A1    3/2014

*Primary Examiner* — Laura A Bouchelle
(74) *Attorney, Agent, or Firm* — Naomi S. Rosenman-Helfand

(57) ABSTRACT

The invention provides a safe auto-needle device for injection, comprising: a main housing and a syringe-support receiving a disposable prefilled syringe terminating in a needle covered by a needle sheath (NS). The speed of depressing of the syringe plunger is manually controllable by a user. In a first embodiment, a locking mechanism is present, for preventing premature advancement of the needle. A second embodiment comprises an interlock, for preventing depressing of a plunger, prior to advancement of the syringe-support to a needle penetration location. Additional components include a drive mechanism; and a needle shield moveable between: a needle covered position; a partially exposed position, to a fully extended needle safe position. The invention also discloses a needle sheath (NS) remover.

27 Claims, 63 Drawing Sheets

(51) Int. Cl.
*A61M 5/31* (2006.01)
*A61M 5/315* (2006.01)

(52) U.S. Cl.
CPC ...... *A61M 5/3129* (2013.01); *A61M 5/31501* (2013.01); *A61M 5/31511* (2013.01); *A61M 5/3243* (2013.01); *A61M 2005/3125* (2013.01); *A61M 2005/3247* (2013.01)

(58) Field of Classification Search
CPC ................ A61M 5/5013; A61M 5/502; A61M 2005/206; A61M 2005/208; A61M 2005/2418
See application file for complete search history.

(56) References Cited

U.S. PATENT DOCUMENTS

| | | | |
|---|---|---|---|
| 7,918,824 B2* | 4/2011 | Bishop | A61M 5/24 604/136 |
| 8,758,304 B2* | 6/2014 | Kemp | A61M 5/2033 604/198 |
| 2010/0016803 A1 | 1/2010 | Liversidge | |
| 2011/0054411 A1 | 3/2011 | Dowds et al. | |
| 2012/0191047 A1* | 7/2012 | Raday | A61M 5/2033 604/198 |
| 2012/0238961 A1 | 9/2012 | Julian et al. | |

* cited by examiner

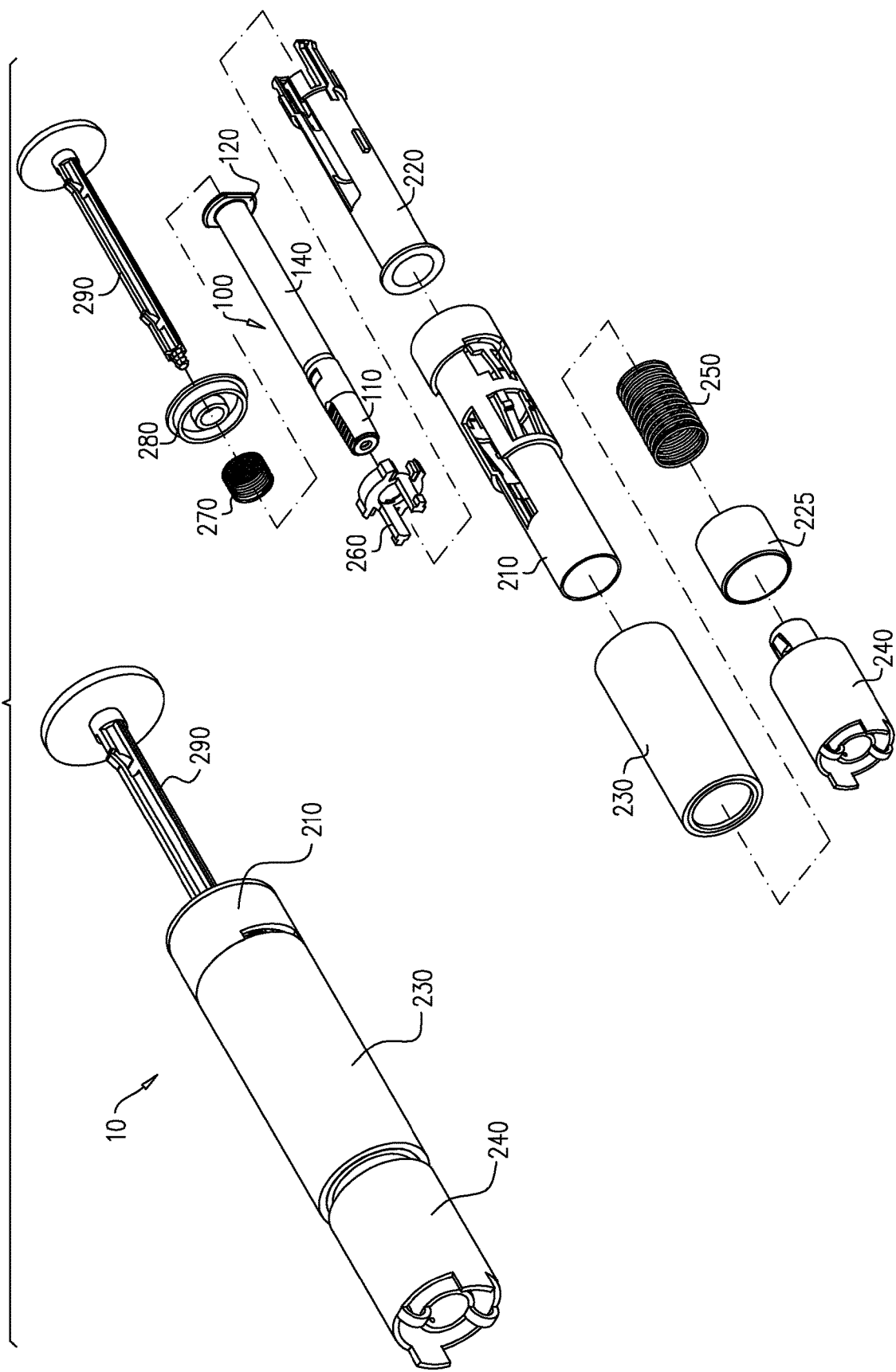

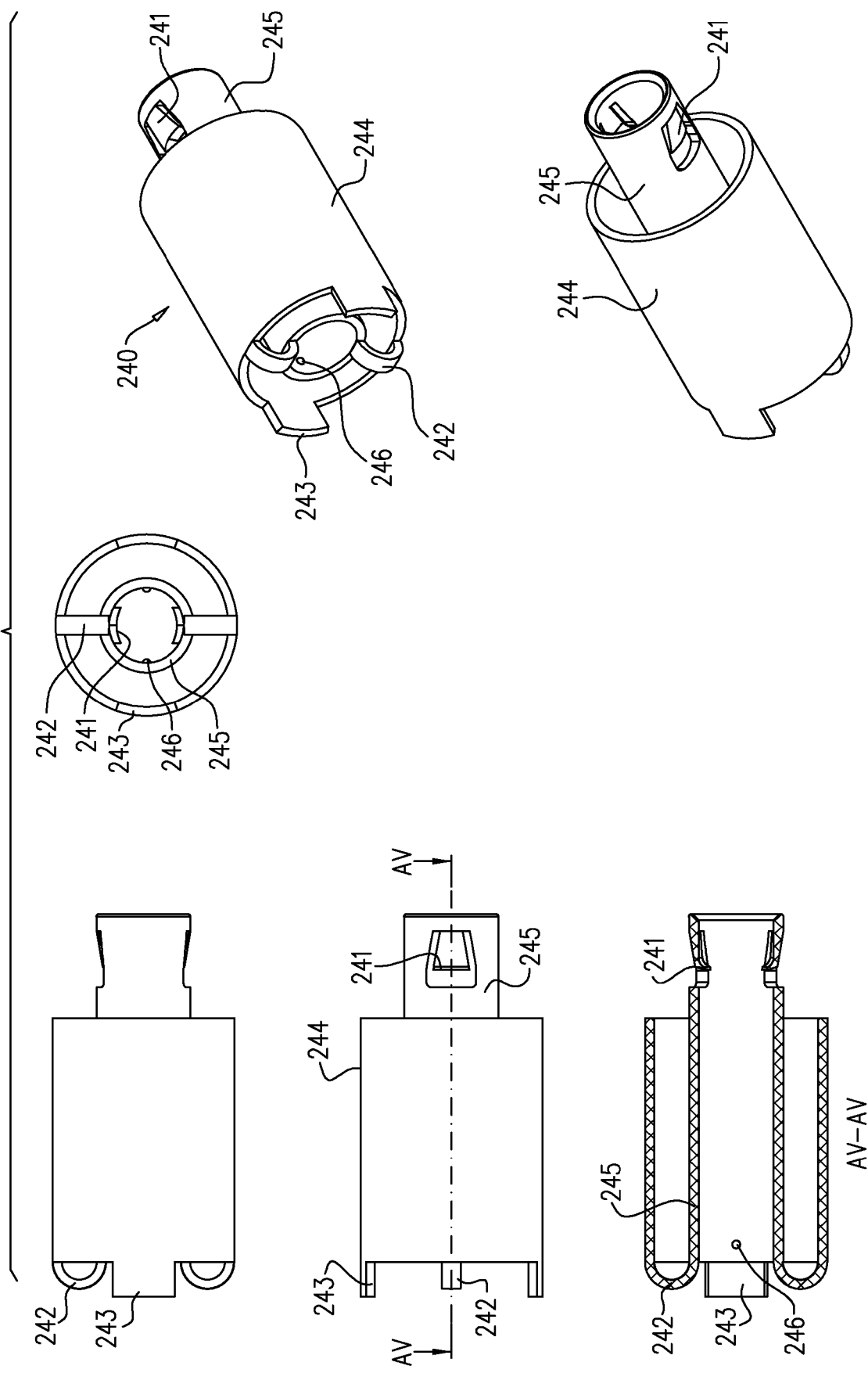

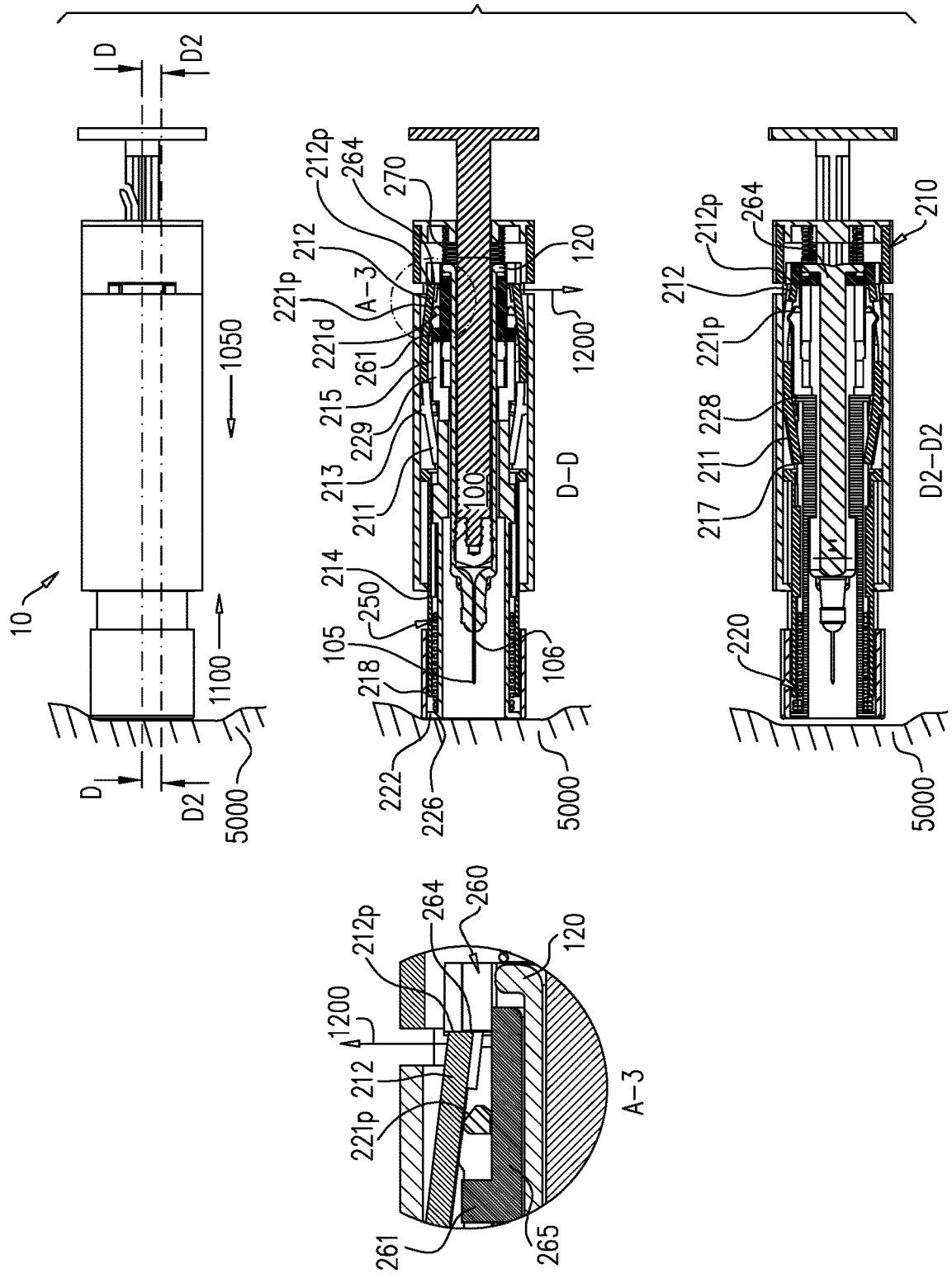

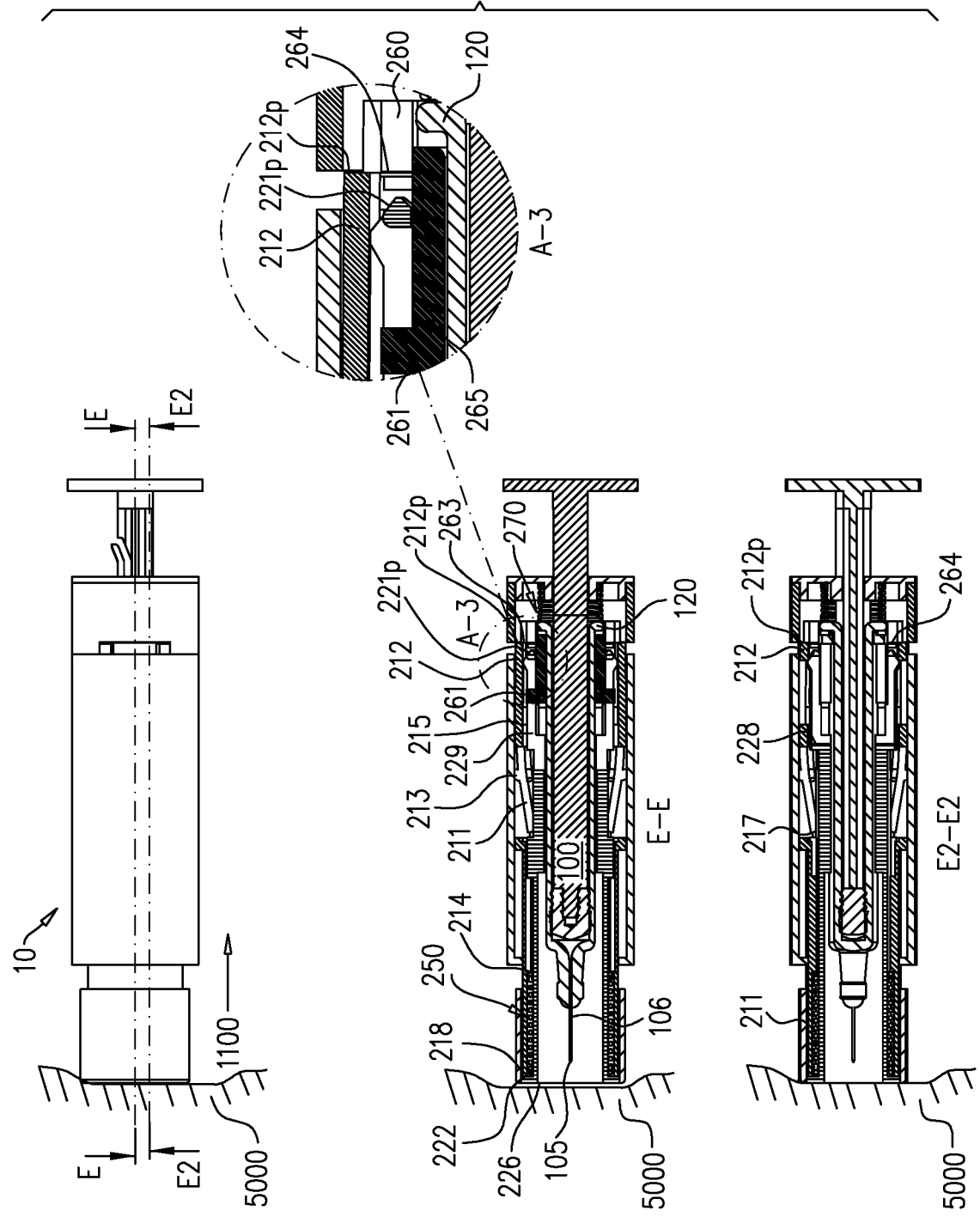

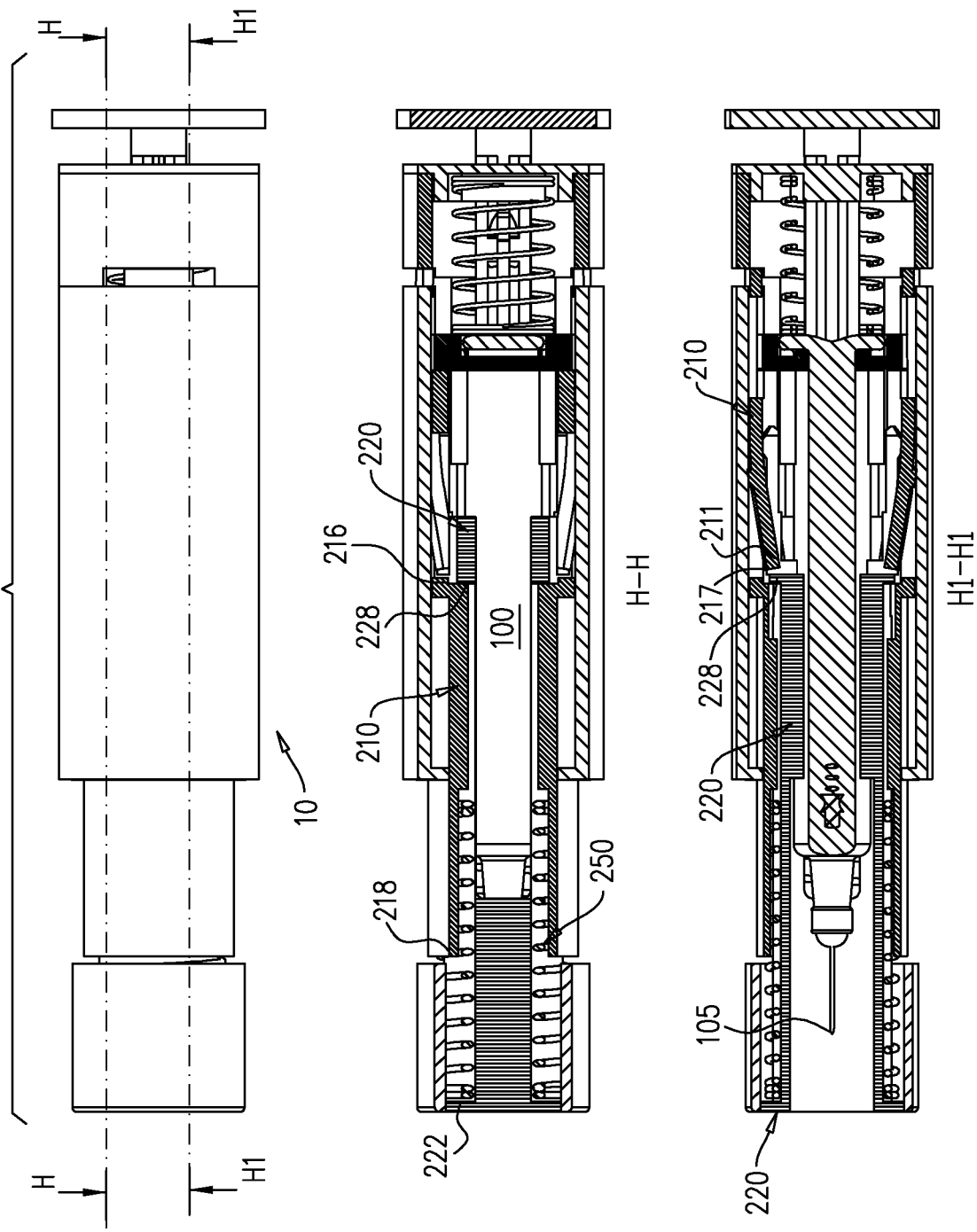

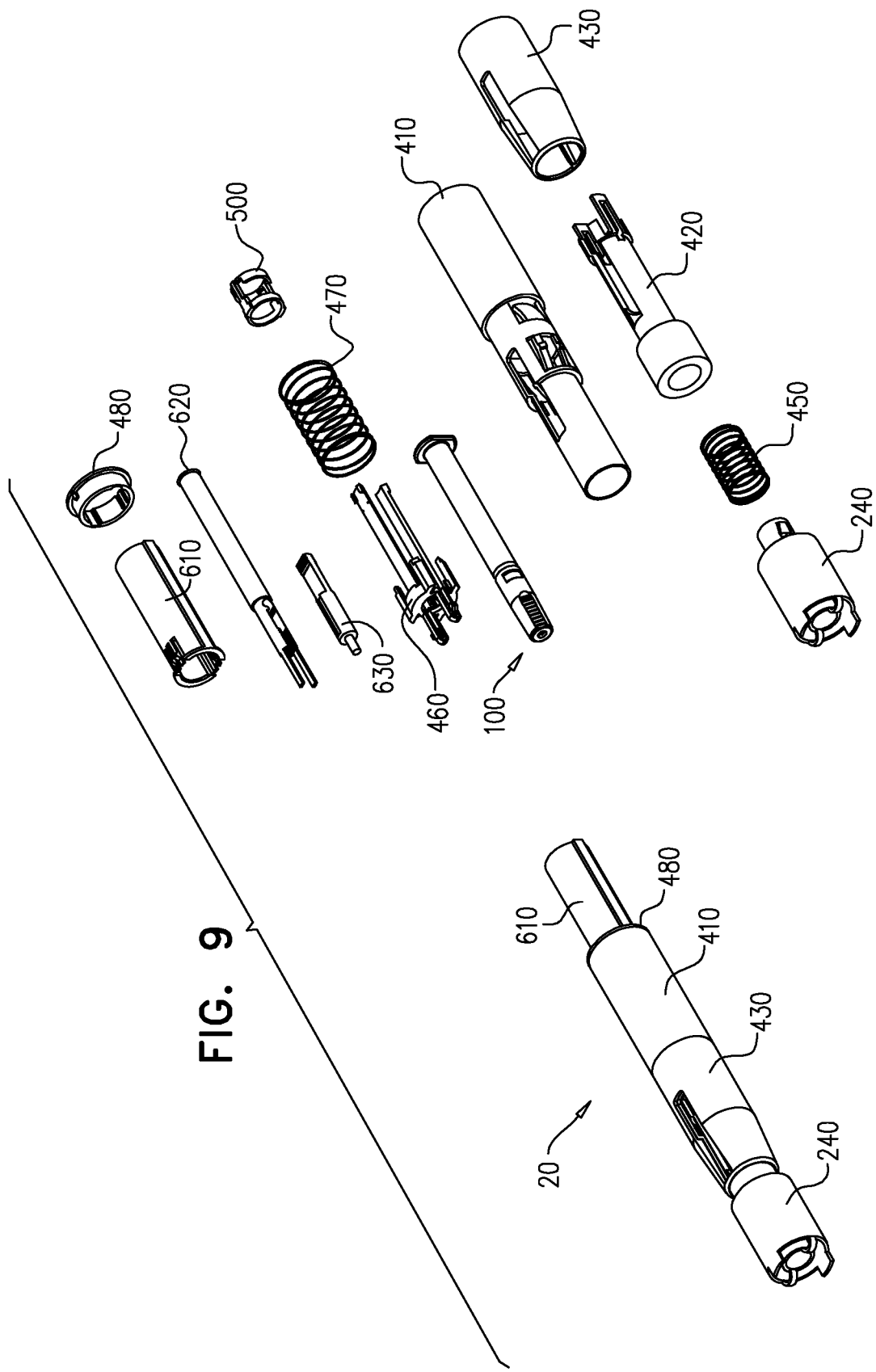

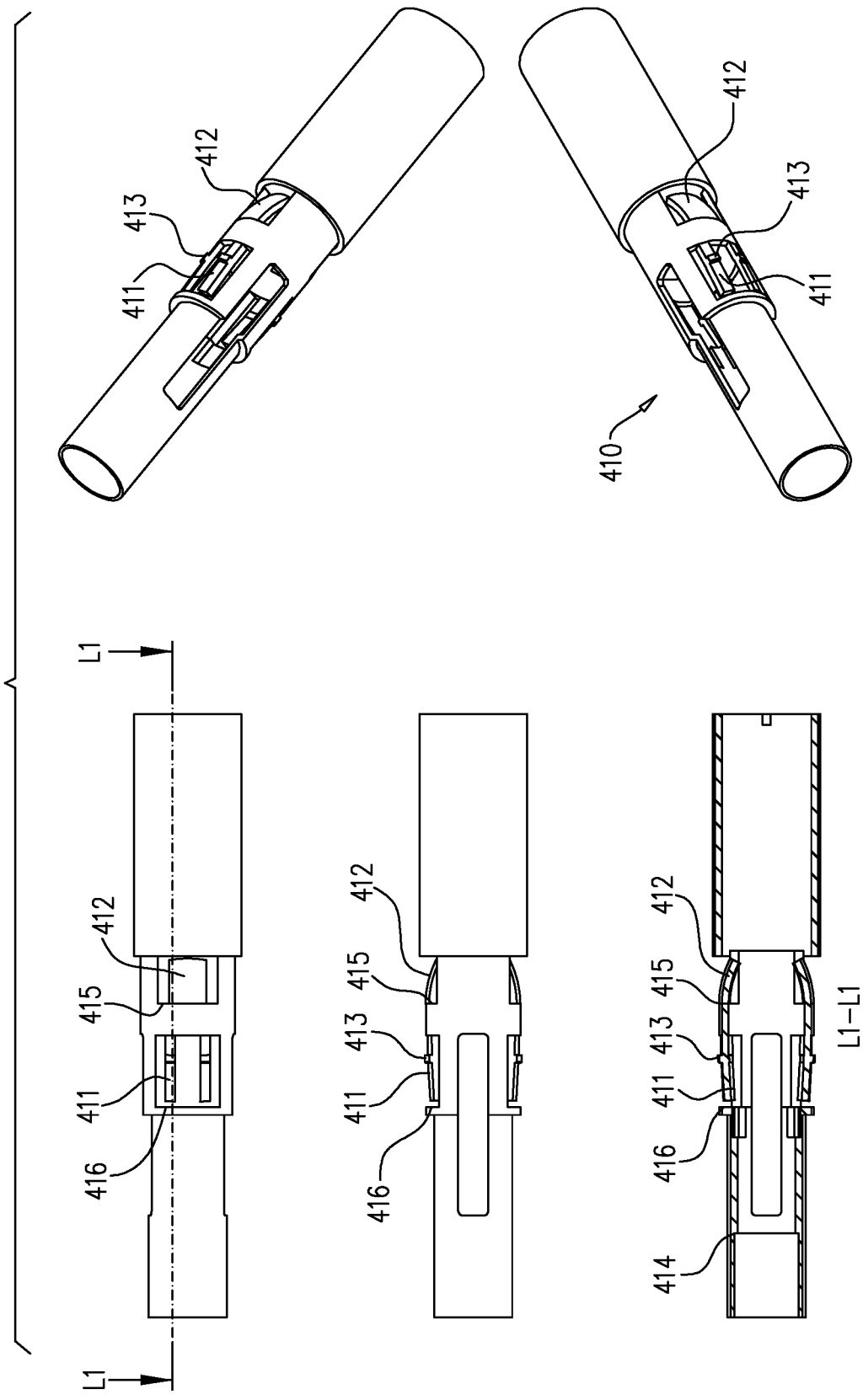

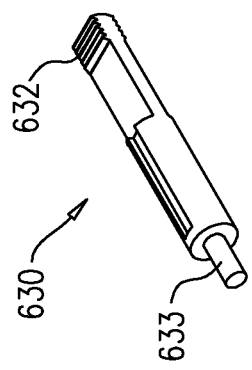
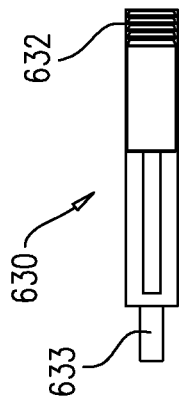
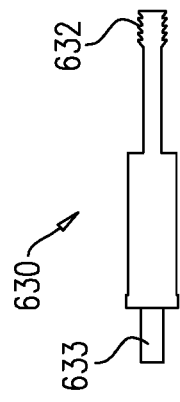
FIG. 10H
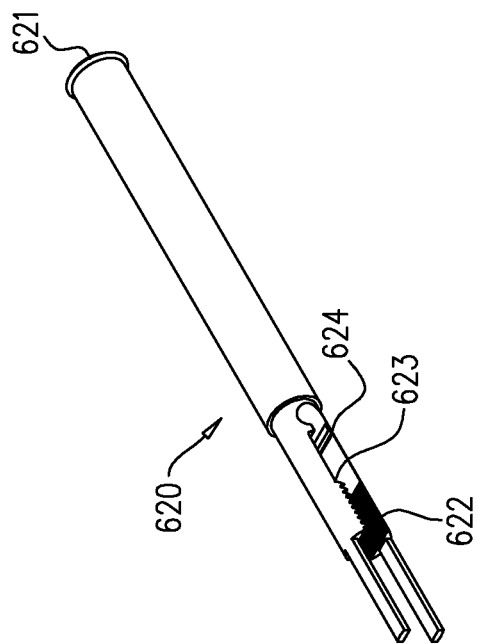
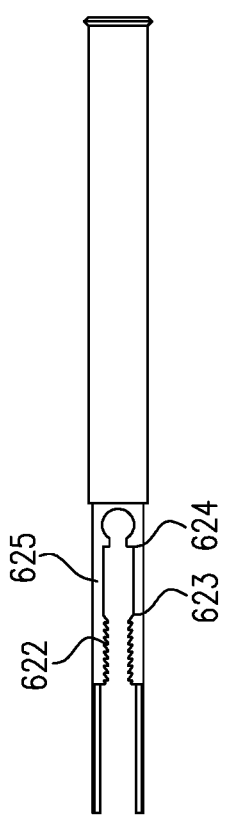
FIG. 10G

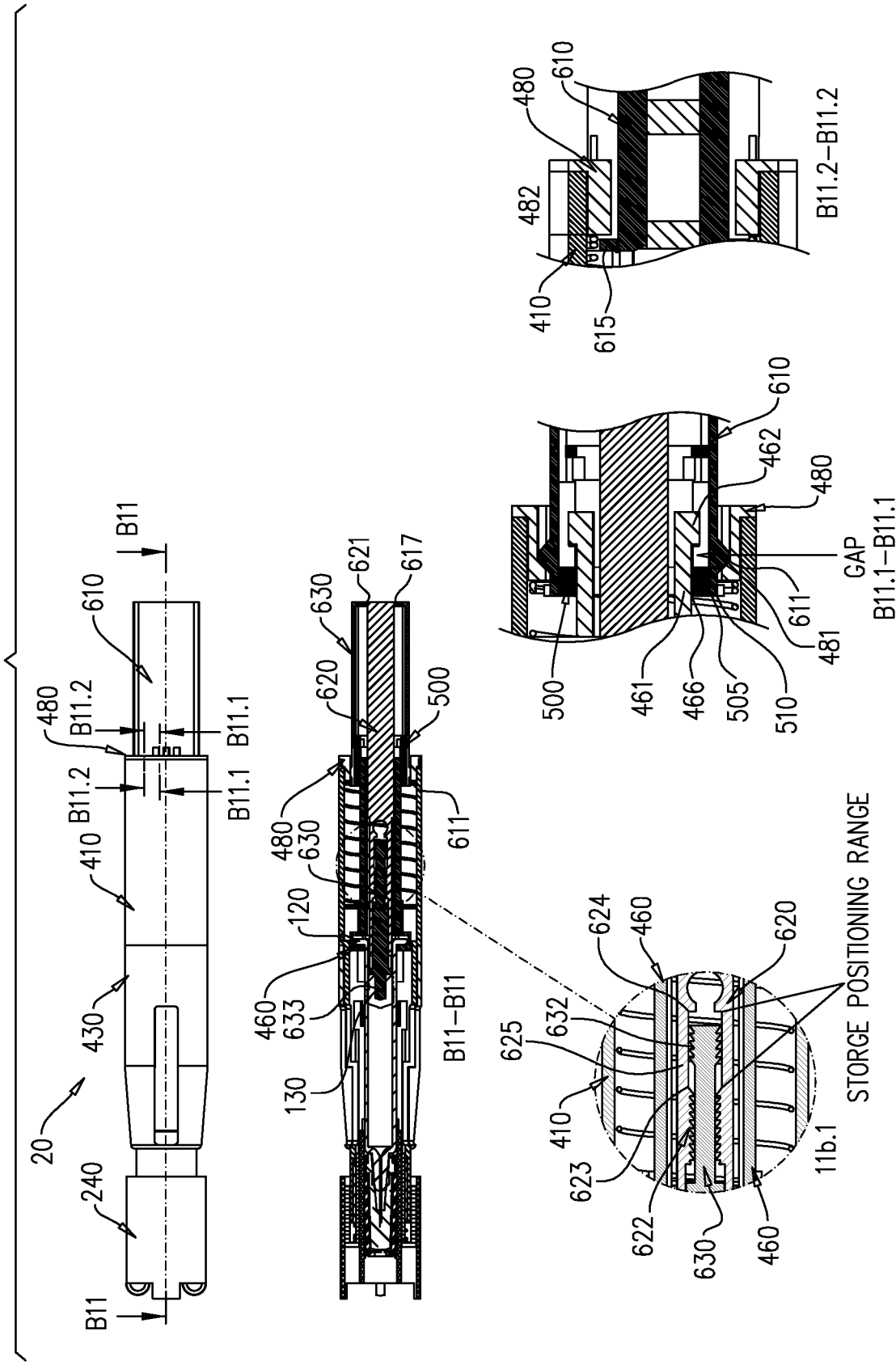

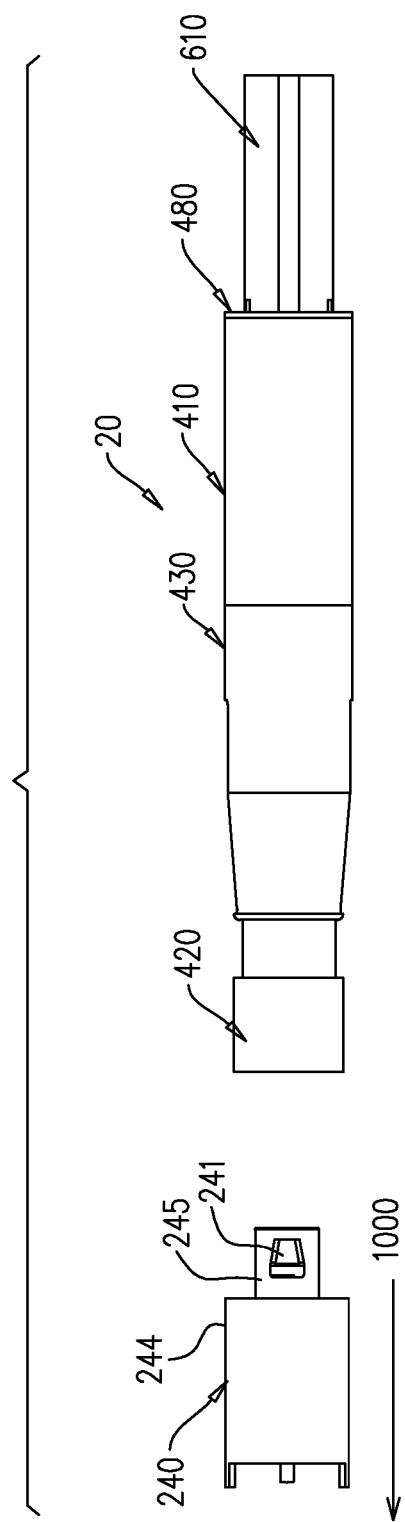

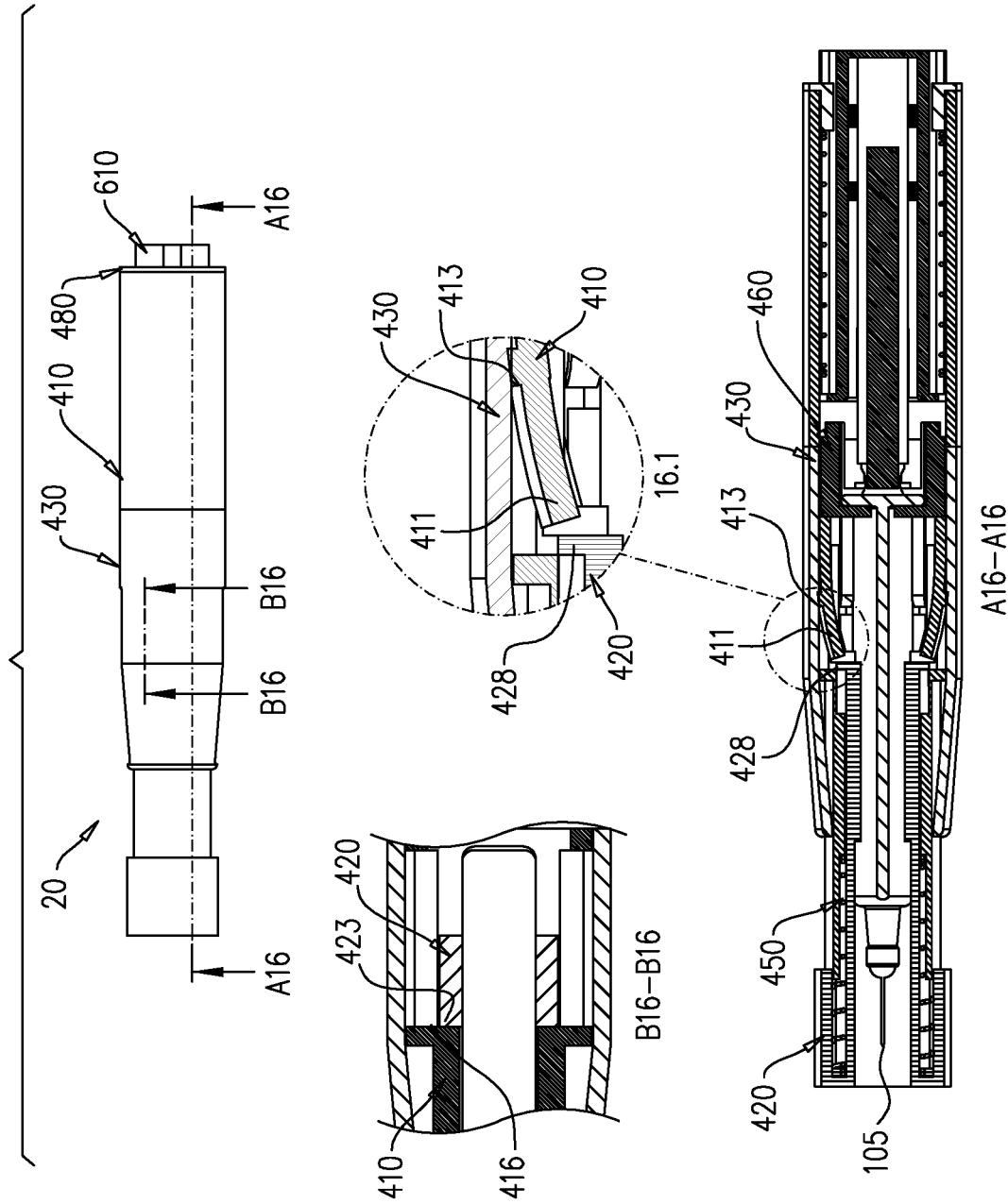

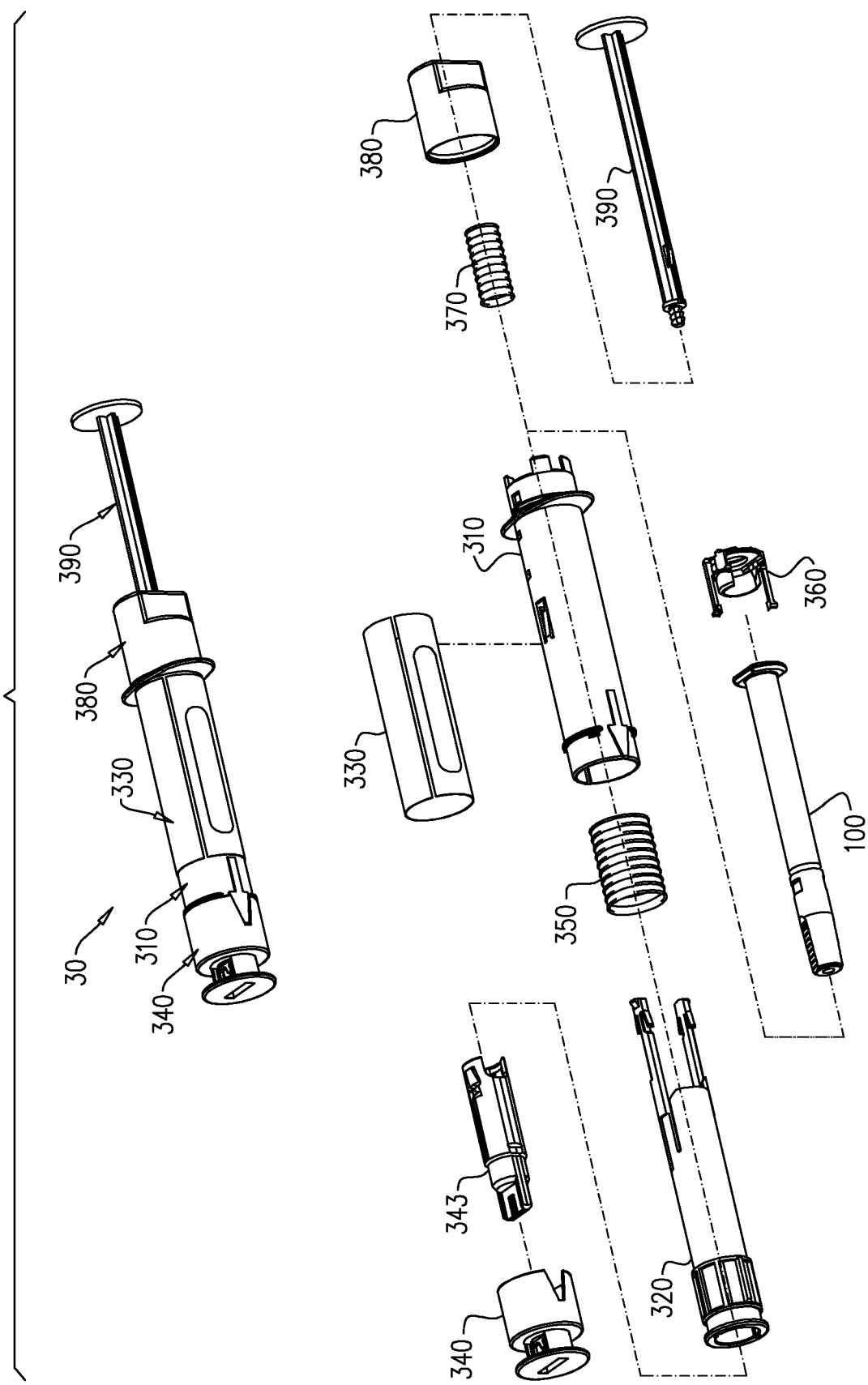

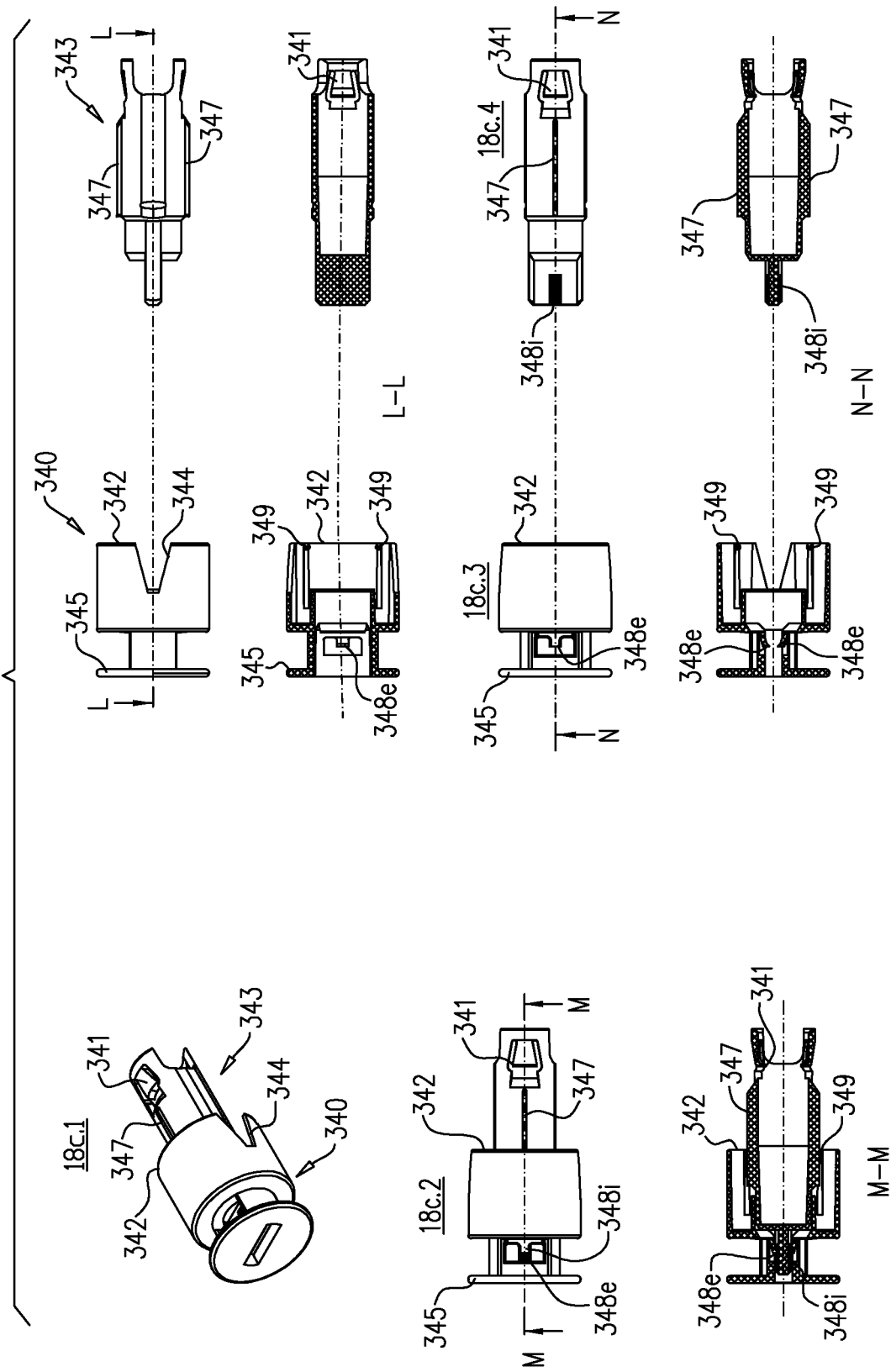

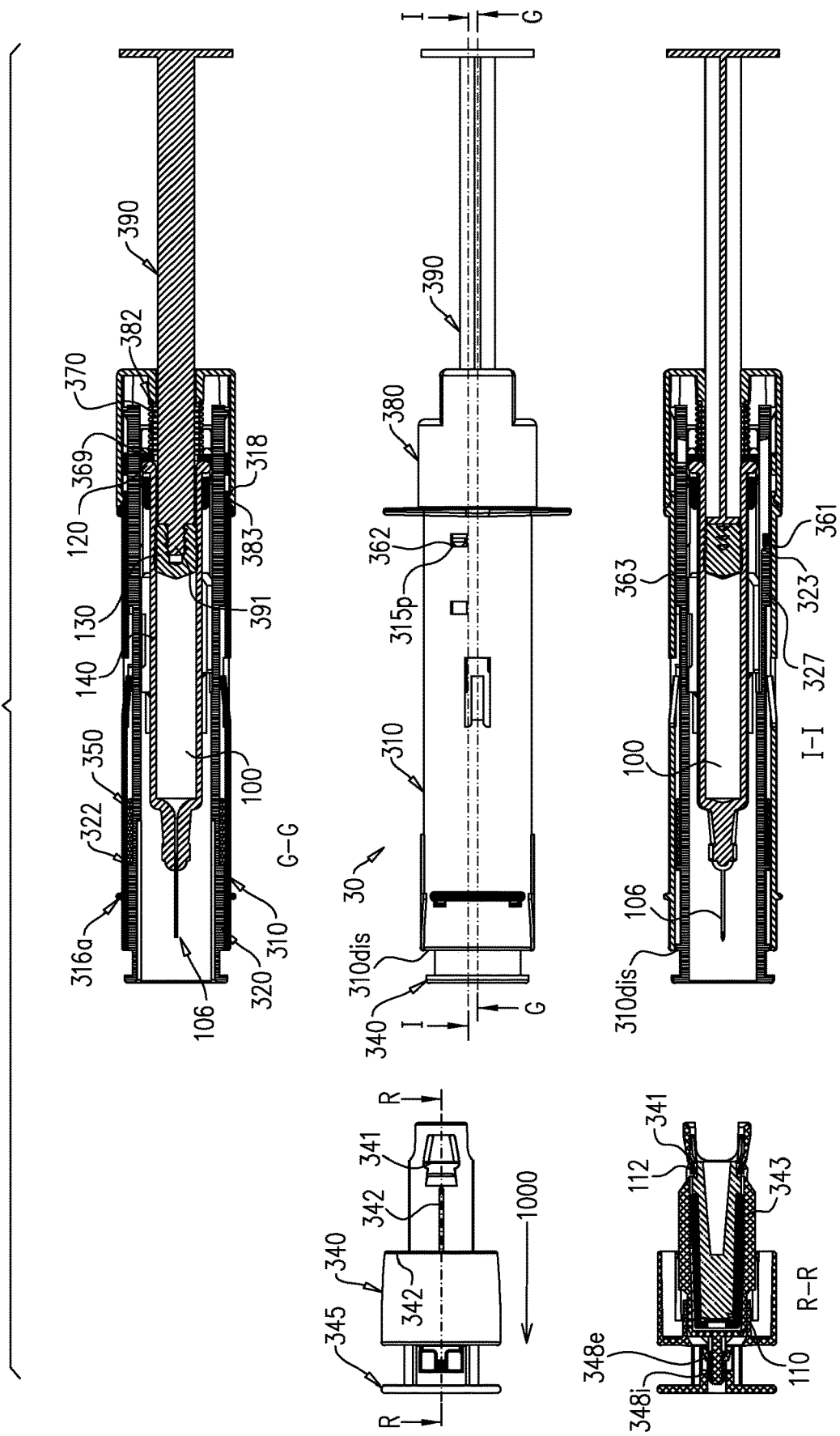

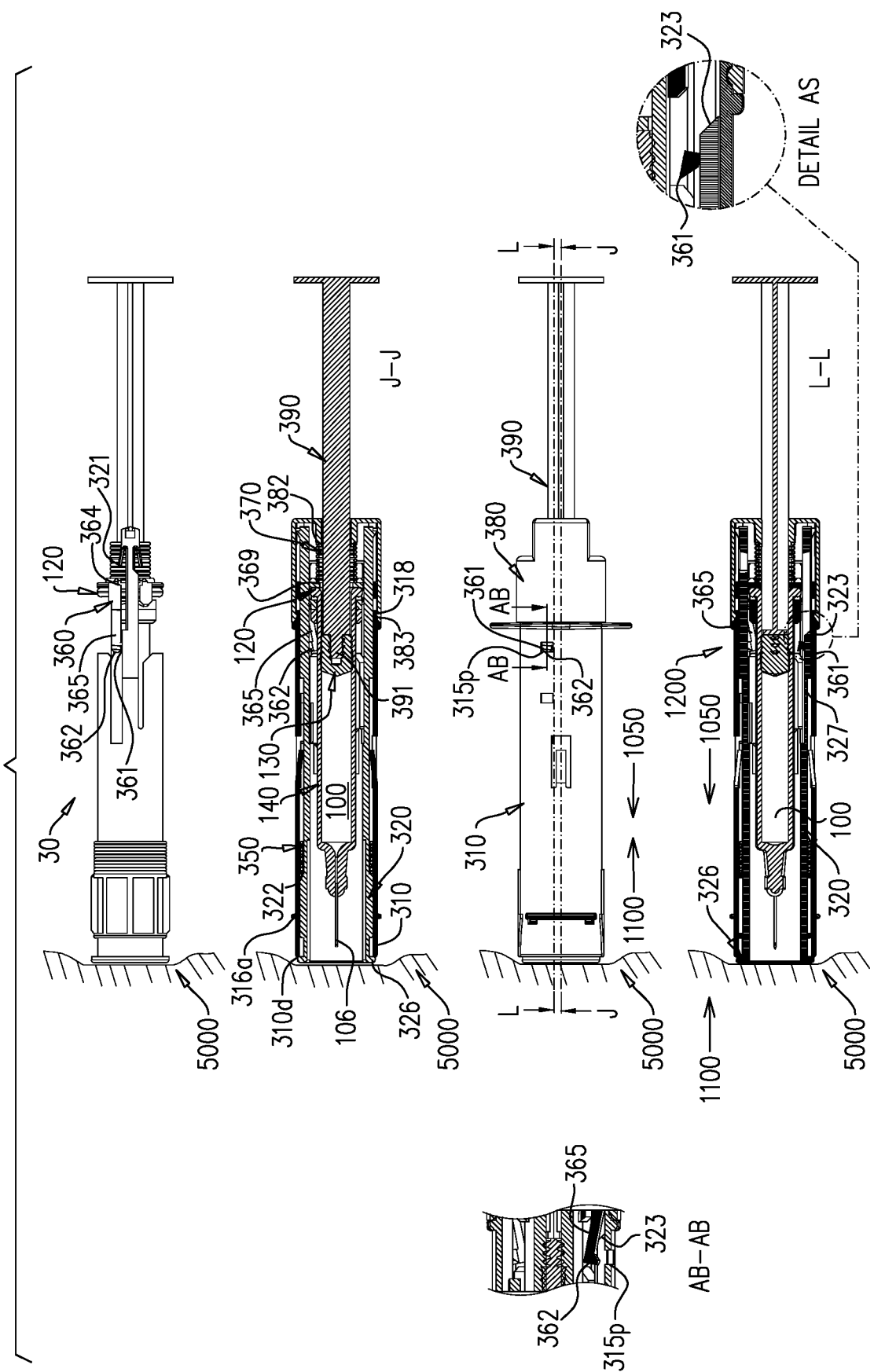

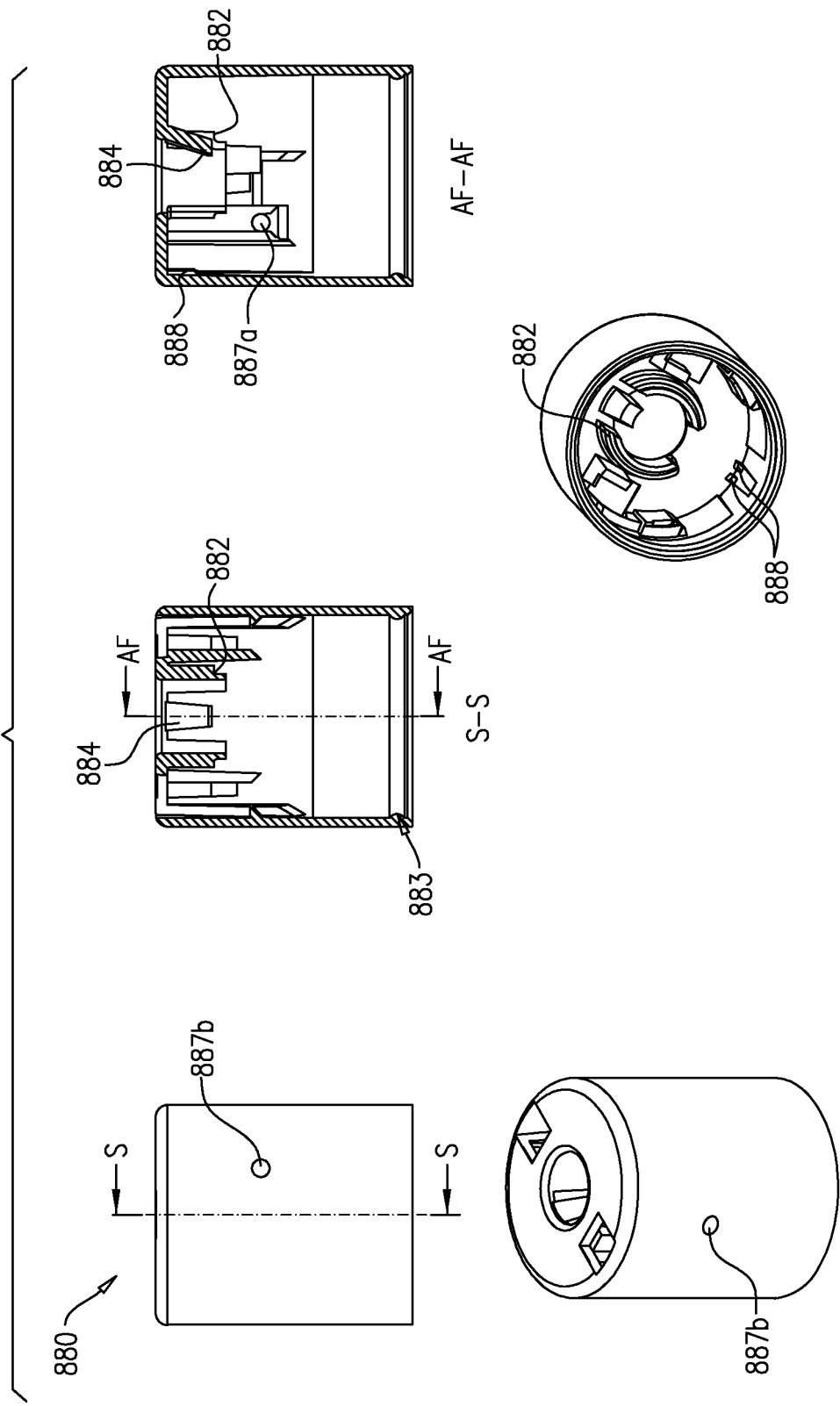

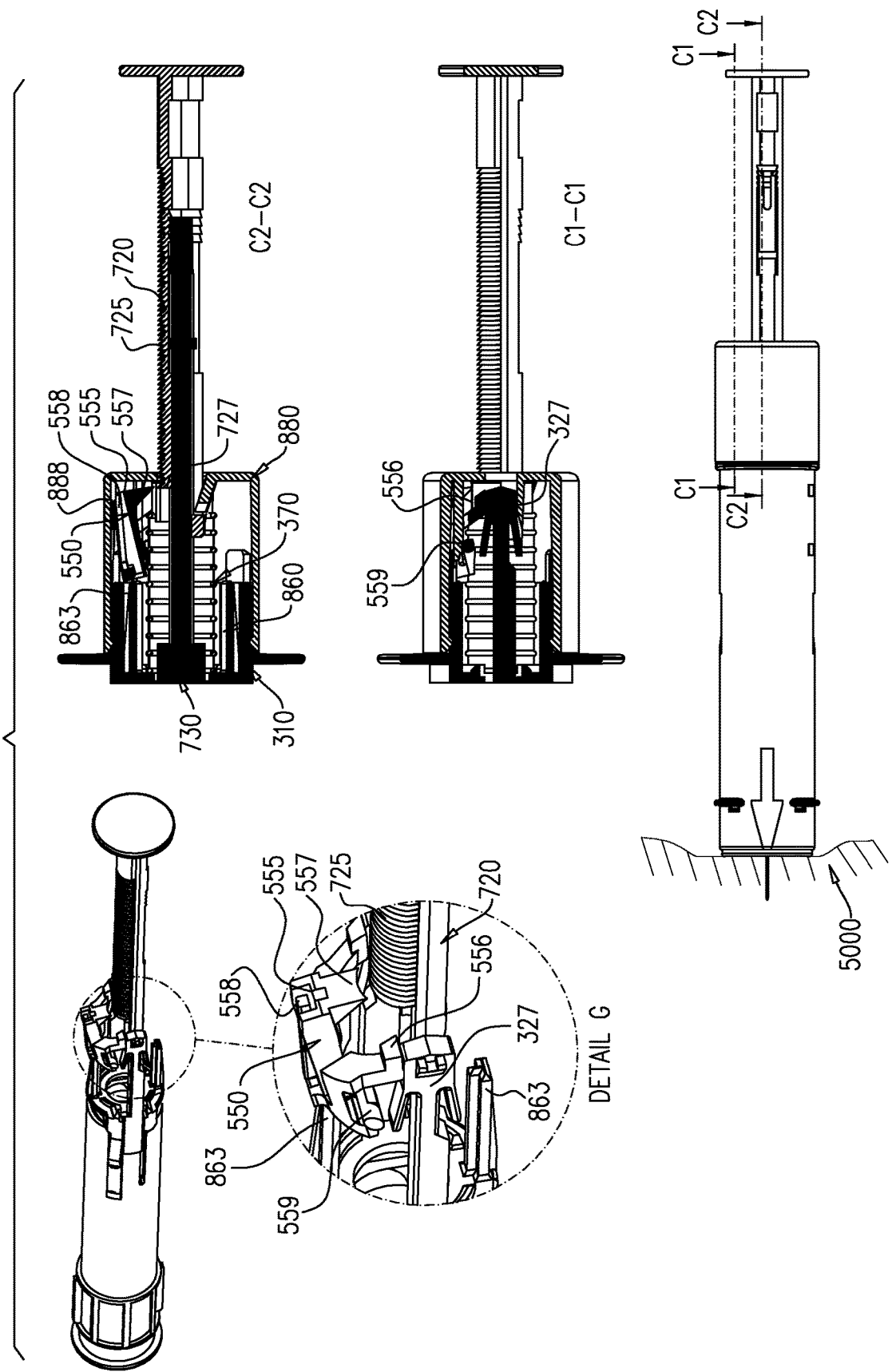

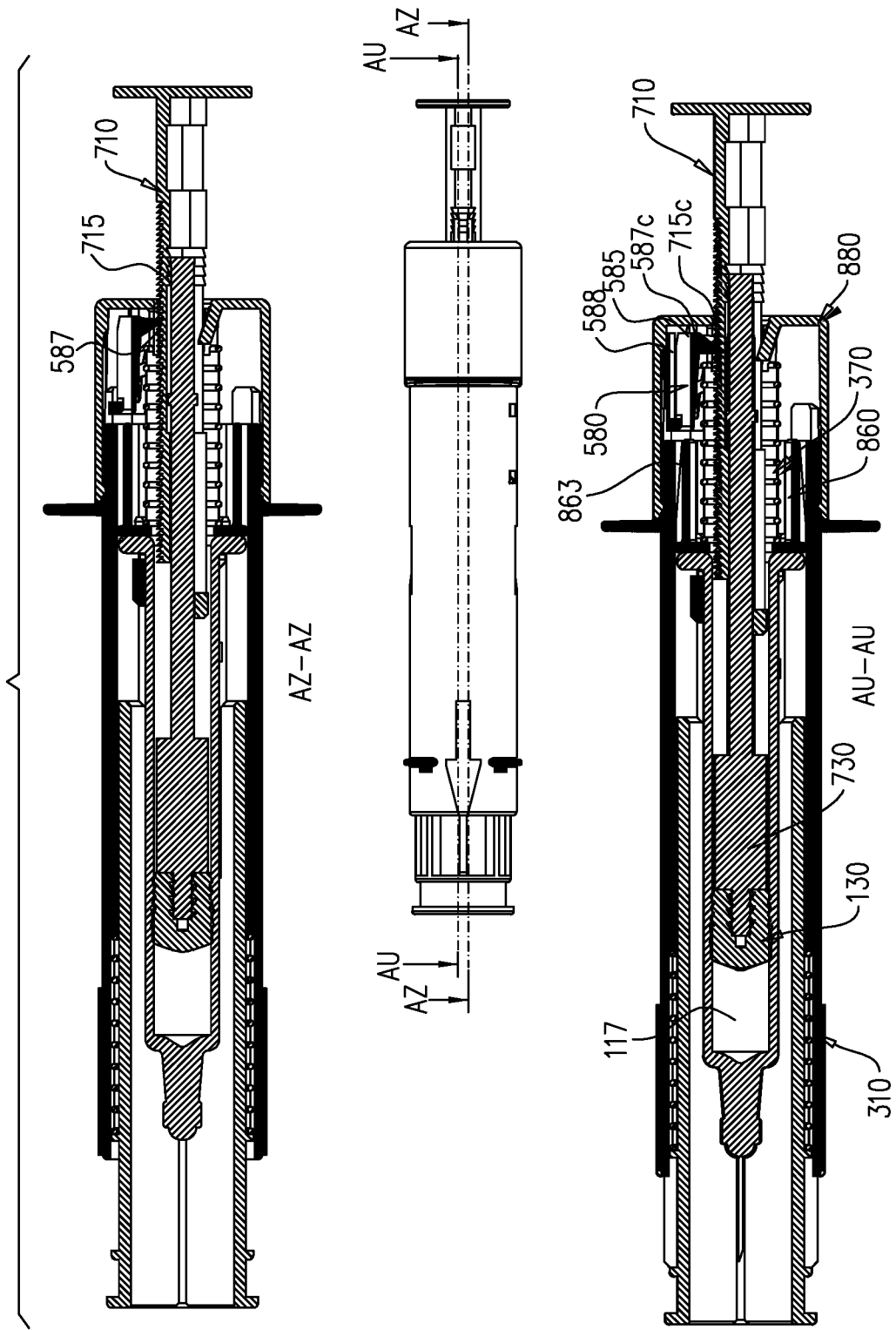

SAFE AUTO-NEEDLE DEVICE

FIELD OF THE INVENTION

The invention relates generally to medical syringe devices, and more specifically to a device for auto-injection such as is performed by a laymen.

BACKGROUND

Patients with a chronic illness may require repeated injection of medicaments to treat their condition, and may prefer to administer their own injections, to maximize convenience.

Typical errors made by laymen attempting to perform self-injection, include: triggering a premature discharge of the drug prior to insertion of the needle, accidental needle pricks, unintentional distortion of the needle prior to use, and breakage of the syringe by inadvertently dropping a glass syringe.

Safe needles are relatively simple syringes, which protect a user from unintentional needle pricks by either removing or sheathing the needle after use. While many safe needles, or more costly auto-injectors, provide protection from accidental needle pricks, the need exists to protect a layman from the remaining errors listed hereinabove. While auto-injectors usually prevent most laymen errors, they are relatively expensive for the end user or the pharmaceutical companies. Auto-injectors may be preloaded for a single use, requiring extensive refrigerated storage space. They typically come with a fixed injection speed which may be painful for the user. They are often complex in structure, requiring many user steps and thus are difficult to use. When they are non-disposable and accept prefilled syringes, they require an initial pricey acquisition expense.

State-of-the-art injection solutions currently available for use by both healthcare professionals and laymen, include standard needles and syringes, and safety needles such as U.S. 2010/0016803. These are typically attachable through a luer/luer-lock connector to standard luer syringes and safety syringes, preferably to prefilled glass/plastic syringes with staked needles, such as U.S. Pat. No. 6,685,676, or disposable and reusable "pens" and auto-injectors such as U.S. Pat. No. 8,376,998 (disposable, single-use) and WO 2014/037946 (reusable, electronic). None of these overcome the aforementioned disadvantages.

The safe auto-needle of the present invention provides the novel advantage of allowing the user to control the injection speed, providing increased compliance and comfort. This feature is not known in prior art disposable auto-injectors. The invention also offers the major advantages of an auto-injector, namely, the needle is hidden in all stages of operation and automatically penetrates the skin upon pressing the device against the injection site, thus reducing patient anxiety and perceived pain, and enabling consistent and appropriate needle penetration depth. After use, the needle is automatically locked in a covered position to prevent needle-stick injuries.

The auto-needle of the invention is characteristically disposable, and is relatively inexpensive for the end-user to purchase.

It is the object of the present invention to provide a layman with an auto-needle which is simple to use and protects the user from typical layman errors such as premature discharge of the medication, breakage of the syringe or bending of the needle prior to use. These and other features and advantages of the invention will be enlarged upon in the detailed description of the invention that follows.

BRIEF DESCRIPTION OF THE DRAWINGS

For a better understanding of the invention, with regard to the embodiments described, reference is made to the accompanying drawings, in which components are not necessarily drawn to scale, and in which:

FIGS. 1-33 describe five embodiments of the invention:

FIG. 1-8 relate to a basic Embodiment 1;

FIG. 9-16 describe Embodiment 2, having an interlock for preventing a user from pressing the plunger before the needle has completely penetrated the injection site. Additionally, a tri-component plunger is included that allows syringe movement for needle penetration without movement of the proximal plunger.

FIGS. 17-24 describe Embodiment 3, having an alternative two-component ratcheting NS remover.

FIGS. 25-32 describe Embodiment 4, comprising an alternative interlock design, to prevent pressing the plunger before complete needle penetration has occurred. Additionally, a plunger one-way ratchet system prevents additional movement of the plunger after use.

FIG. 33 describes Embodiment 5, in which the plunger is locked from moving, both prior to use of the device, and after use, to prevent spillage of a hazardous medicament.

SUMMARY

Figure 1A:
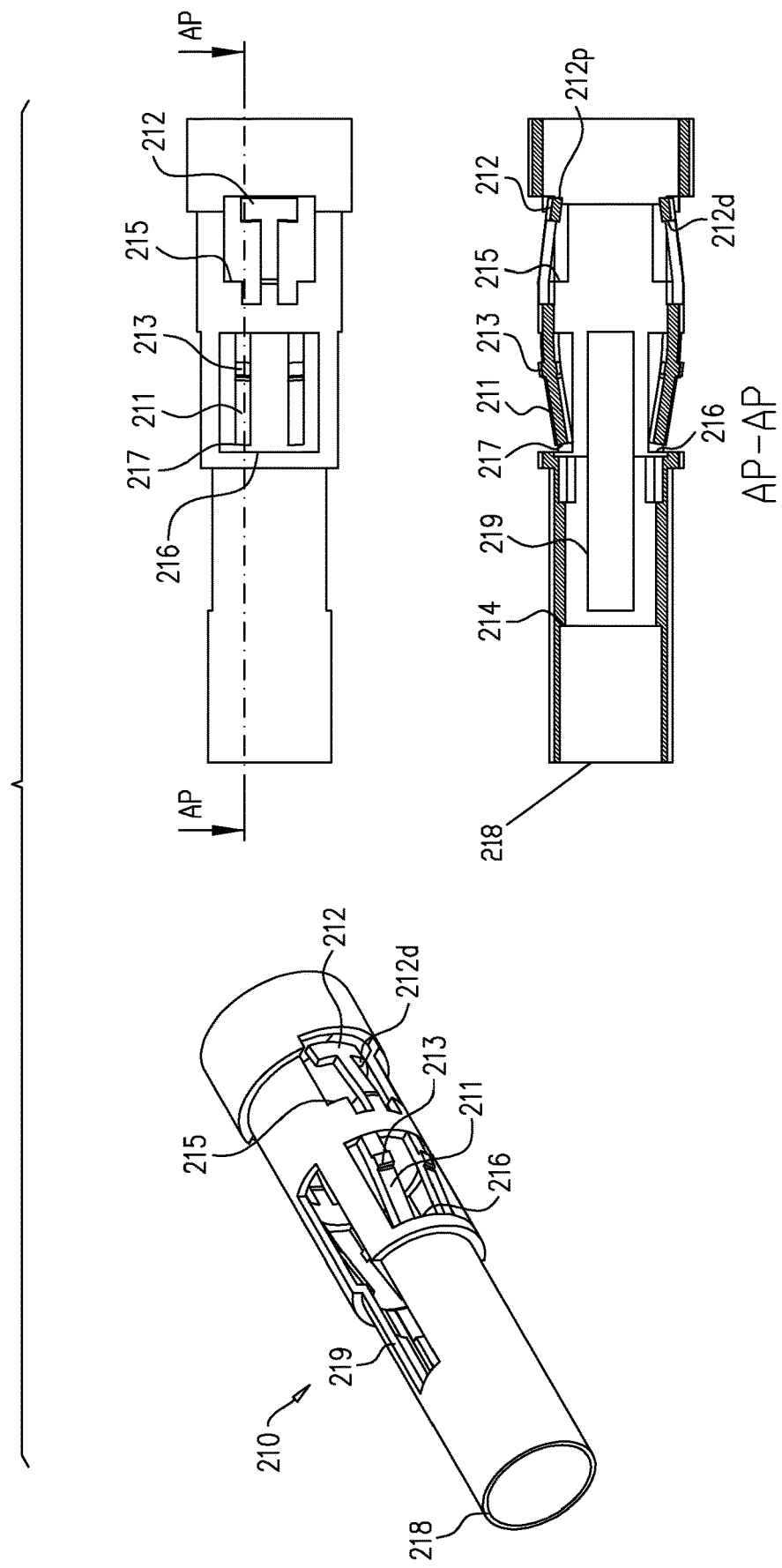

There is thus provided a safe auto-needle device for injection, comprising:
  a) a main housing;
  b) a syringe-support for receiving a proximal end of a disposable prefilled syringe; the disposable prefilled syringe comprises: a piston; a proximal end including a flange; and a distal end terminating in a needle; the needle covered by a needle sheath (NS);
  c) a drive mechanism for advancing the syringe-support distally towards an injection site;
  d) a generally tubular needle shield concentric to the main housing; the needle shield moveable from a first position wherein the needle is covered, to a second position in which the needle is at least partially exposed, to a third fully extended position in which the needle is irreversibly concealed;
    the generally tubular needle shield comprising a distal end for contacting an injection site, and a proximal end;
  e) a spring urging distal movement of the needle shield; and the needle shield comprising a spring seat;
  f) a needle sheath (NS) remover, designed to mate with and irreversibly grip the needle sheath (NS), for removal of the needle sheath prior to injection;
  g) a locking mechanism for preventing premature advancement of the needle; wherein the locking mechanism is constructed such that depressing upon the distal end of the generally tubular needle shield, results in release of the locking mechanism; and the tubular needle shield cannot be depressed prior to removal of the needle sheath (NS);
  h) a plunger rod for engaging the piston of the prefilled syringe, wherein the speed of depressing of the plunger is manually controllable by a user;
    wherein in use of the device, the NS remover is grasped and removed; the distal end of the needle shield is brought into contact with and pressed upon an injection site, resulting in release of the locking mechanism, and in drive of the syringe-support and the associated syringe, distally until needle penetration; and upon depressing of the plunger, a medicament may be injected.

In certain embodiments, the drive mechanism (c) comprises a compressed spring and a spring seat, for urging the syringe-support distally towards the injection site.

Optionally, the plunger rod comprises at least one locking tab to prevent pulling of the plunger rod in the proximal direction, instead of pressing of the plunger rod.

In such case, a rear cap may be included, having a hollow center through which the plunger rod enters, and an internal lock bracket, the lock bracket interacting with the locking tab of the plunger to prevent pulling of the plunger, ensuring unidirectional movement of the plunger.

Moreover, the locking mechanism (g) may comprise T-shaped locking arms of the main housing, opposing and pressing on the syringe-support; and release of the locking mechanism comprises lifting of the T-shaped locking arms radially outwards, by proximal movement of the needle shield.

Additionally, a locking mechanism may be included for locking the needle shield after injection, in the third fully extended position, fully covering a needle tip. The needle shield locking mechanism may comprise: lower locking arms present upon the main housing, which hold the needle shield in a fully extended position covering the needle, after use.

Furthermore, a terminal distal end of the NS remover may comprise bumpers to receive and dampen axial load applied to the NS remover when the device is dropped; thereby preventing breakage of a prefilled syringe.

In certain embodiments, the NS remover is comprised of an inner tubular portion comprising snap teeth for mating with an NS, and an outer concentric tubular portion comprising a grip face; and flexible connection arms connect the inner and outer portions.

The device may comprise a transparent viewing window in the main housing, allowing viewing of the state of a medicament present in a prefilled syringe held in the device.

In a presently preferred embodiment, the device comprises an interlock, for preventing depressing of a plunger, prior to advancement of the syringe-support to a needle penetration location. In such case, the interlock may comprise an outwardly facing locking face. Further, movement of the interlock, and premature pressing of the plunger, are prevented during storage, by engagement of locking face protrusions located upon anterior plunger pusher, within appropriate grooves of locking faces of a rear cap; and the outwardly facing locking face of the interlock prevents the locking face protrusions from bending inwardly. Additionally, release of the interlock can be performed by distal movement of the syringe-support, by the drive mechanism; resulting in distal movement of the interlock's locking face from its previous position opposite the locking face protrusions of the anterior plunger pusher; the protrusions are free to bend inwardly and disengage from the internal grooved locking faces of the rear cap; allowing the anterior plunger pusher to be pressed by a user.

In some embodiments, the plunger rod is a tri-component plunger having one-way ratchet teeth. The tri-component plunger may comprise: an anterior plunger pusher; and a proximal plunger having angled one-way ratchet teeth, which may engage appropriate one-way ratchet teeth upon a distal plunger; and the proximal plunger comprises in an internal face a storage area in which the ratchet teeth are disengaged prior to use of the device, the storage area allowing movement of the distal plunger due to internal air pressure in a syringe. In some instances, the tri-component plunger, advantageously does not prevent movement of the syringe-support for needle penetration, when a user forcefully grasps the anterior plunger pusher during use.

The invention additionally provides a NS remover comprised of:
an internal part for mating with the NS;
and an external part for transferring impact forces upon dropping of the device, to a stopper on the main housing;
and ratchet teeth are present on one of: the internal part, and the external part; for engaging flexible teeth upon the other of: the external part and internal part; the ratchet teeth allowing tolerance in position of the NS during storage.

The NS remover internal part may be guided axially on the needle shield thus preventing a bending load on the needle.

In some embodiments of the device, the locking mechanism (g) comprises locking arms present on the syringe-support; the locking arms entering stop windows on the main housing; and wherein in release of the locking mechanism, activation slopes located at the terminal end of the locking arms slide against activation slopes of the proximally moving needle shield; thereby bending the locking arms inward and removing the locking arms from the stop windows.

Moreover, the interlock may be structured to block pressing of the plunger until the syringe-support has advanced distally to a needle penetration position; thus preventing user error of premature discharge of a medicament.

Optionally, the plunger comprises a plurality of locking teeth present upon the length of the plunger;
and the interlock comprises a pivot hinge, and a flexible load beam for urging pivoting of the interlock on the hinge upon user initiation of an injection;
and the interlock terminates in at least one locking tooth designed to engage one or more of the locking teeth present upon the plunger, the engagement preventing the plunger from being pressed; and the engagement occurring prior to needle penetration.

In some instances, the interlock locking tooth is designed to engage the at least one plunger locking tooth, after use of the device.

Furthermore, the interlock may comprise one or more guiding holes designed to mate with and accept therein, one or more lengthened release fingers present upon the syringe-support; the mating preventing the at least one locking tooth of the interlock from disengaging from the locking teeth of the plunger; wherein distal advancement of the syringe-support towards an injection site results in removal of the one or more lengthened release fingers from within the one or more guiding holes.

In some instances, the device includes a plunger one-way ratchet system for preventing pulling of the plunger proximally and allowing only pressing of a plunger distally. In such case, optionally the plunger is a two component plunger comprised of a proximal plunger component and a distal plunger component; each of the plunger components having at least one ratchet tooth allowing mating of the two plunger components during pressing of a plunger; and the plunger components have a pre-engagement positioning, allowing the components to slide upon one another allowing for tolerance in axial positioning, prior to pressing of the plunger.

Optionally, the interlock is additionally structured to block movement the plunger after use of the device. In such case, the interlock comprises two terminal locking teeth angled in opposing directions and engaging appropriately angled locking teeth, present upon the length of the plunger.

Further, the device may comprise a plurality of longitudinal ribs located internally within the needle shield, the ribs providing axial support for the prefilled syringe.

In one embodiment, the main housing includes a viewing window allowing viewing of the contents of the prefilled syringe when the tubular needle shield is in the first position.

The invention also provides an NS remover, for use with an injection device comprising a syringe, a needle and a needle sheath; the NS remover comprising:

an internal part for mating with the needle sheath (NS);

and an external part for transferring impact forces upon dropping of the injection device, to a stopper on a main housing of the injection device;

and ratchet teeth are present on one of the internal part and the external part, for engaging flexible teeth upon the other of the external part and the internal part; the ratchet teeth allowing tolerance in position of the (NS) needle sheath during storage.

DETAILED DESCRIPTION OF THE INVENTION

In the following detailed description, numerous specific details are set forth in order to provide a thorough understanding of the present invention. There is no intention to limit the invention to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

In a general overview, the safe auto-needle of the invention is a cost-effective disposable device, into which disposable prefilled syringes are placed. The device provides several novel safety advantages, especially important for a layman user. Premature discharge of the contents of the syringe is prevented, as occasionally a user will attempt to press the syringe plunger before the needle has been fully deployed. Similarly, a mechanism is included to prevent the plunger from being extended instead of being depressed, to avoid unintentional medication spillage or introduction of air bubbles into the syringe. Prefilled syringes typically are marketed including a soft or rigid needle sheath (NS), which needs to be forcefully removed by the user prior to use, leading to accidental distortion of the needle tip, and dropping and breakage of glass syringes. The auto-needle of the invention includes a component termed the NS Remover, which allows effortless gripping of the needle sheath, prevents the user from bending the needle when removing the sheath, and is structured to provide shock absorbance in case the device is dropped. Additionally, the needle is shielded, until triggered by the user to advance to its pre-penetration position, and is once again automatically shielded after use, to prevent post-injection inadvertent pricks. In addition, the auto-needle of the invention allows the user to control the injection speed, providing reduced injection-related pain, similarly to simple hypodermic syringes (while maintaining the advantages of auto-injectors such as prevention of needle pricks, hiding the needle, and automatic needle penetration, thus reducing patient anxiety and perceived pain). The invention provides a solution for patients that prefer to control the injection speed, and may suffer from needle-phobia, allowing them to persist with their prescribed treatment.

In contrast, prior art simple safe needles do not provide these numerous safety features, while auto-injectors are costly and merely provide patient control of medication injection speed.

Referring now to FIG. 1, the components of the Safe Auto-Needle 10 are shown in both an isometric-exploded view.

Referring to the isometric view, the Safe Auto-Needle 10 of the invention, also termed the "SAN-P", includes a plunger rod 290 at its proximal end, a main housing 210, an outer cover 230 and an NS remover 240 which allows quick and proper removal of a needle sheath prior to use.

Referring to the exploded view in FIG. 1, plunger rod 290 includes one way locking and piston elements, to prevent pulling (hyperextension) of the plunger proximally, instead of compression of the plunger, described hereinbelow in relation to FIG. 1F and FIG. 2B.

A disposable prefilled syringe 100 containing a medicament is inserted by a pharmaceutical company or by a user into the auto-needle device 10 of the invention. Prefilled syringe 100 typically comprises a syringe barrel 140 including a flange 120, a piston (not shown), and a Needle Sheath "NS" 110 which conceals a needle tip (not shown).

The disposable prefilled syringe 100 is received and supported radially by a needle shield 220 and an upper syringe-support 260. Needle shield 220 slides upon the main housing 210 proximally while pressed against the injection site, when needle penetration is triggered by the user. Syringe spring 270 is compressed during assembly, and acts to urge the prefilled syringe 100 and the syringe-support 260 distally towards the injection site.

In the embodiment shown, needle shield 220 and the needle shield front 225 make up a needle shield assembly, and are joined together by any method (bonding, welding, snaps, etc.). The needle shield assembly can be produced as one integral part or produced from any number of parts and assembled thereof. Needle shield spring 250 urges the needle shield 220 distally.

NS remover 240 engages the NS preferably by a snap fit, and allows easy removal of the NS (Needle sheath) to ready the device for injection. The NS remover 240 preferably covers the needle shield front 225.

A rear cap 280 is also included to interact with the plunger rod 290 and syringe spring 270 and ensure unidirectional movement of the plunger rod 290, as described hereinbelow in relation to FIGS. 1E, 2B and 7.

Referring now to FIG. 1A, the main housing 210 is shown in isometric view, in side view and in cross-section view, taken along section line AP-AP in side view.

Referring to FIG. 1A, isometric view, T-shaped locking arms 212 press upon the syringe-support 260 (shown enlarged in FIG. 1D) which holds the prefilled syringe 100; thus locking arms 212 prevent prefilled syringe 100 from prematurely advancing distally before the injection process is initiated.

Figure 6A:
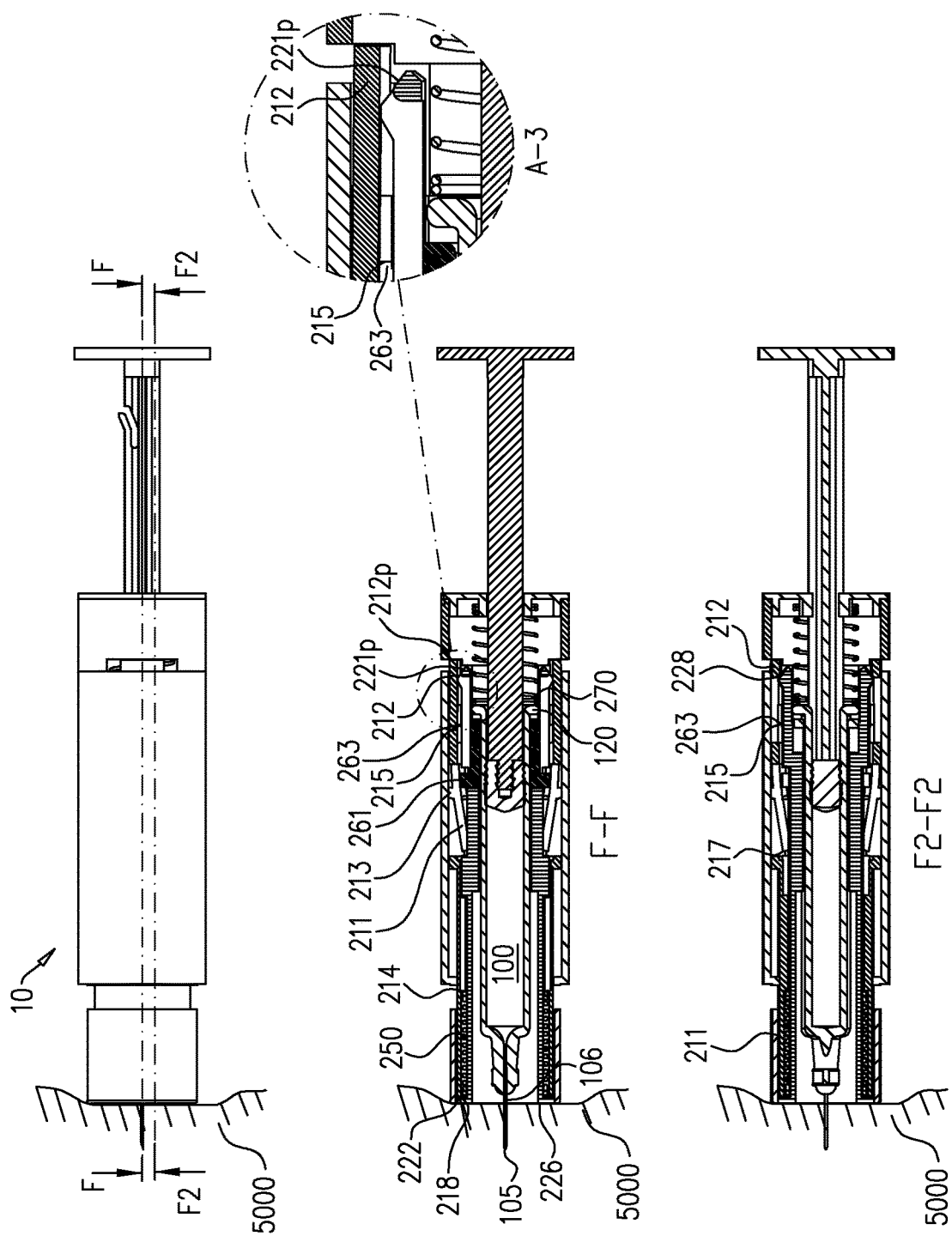
Figure 6B:
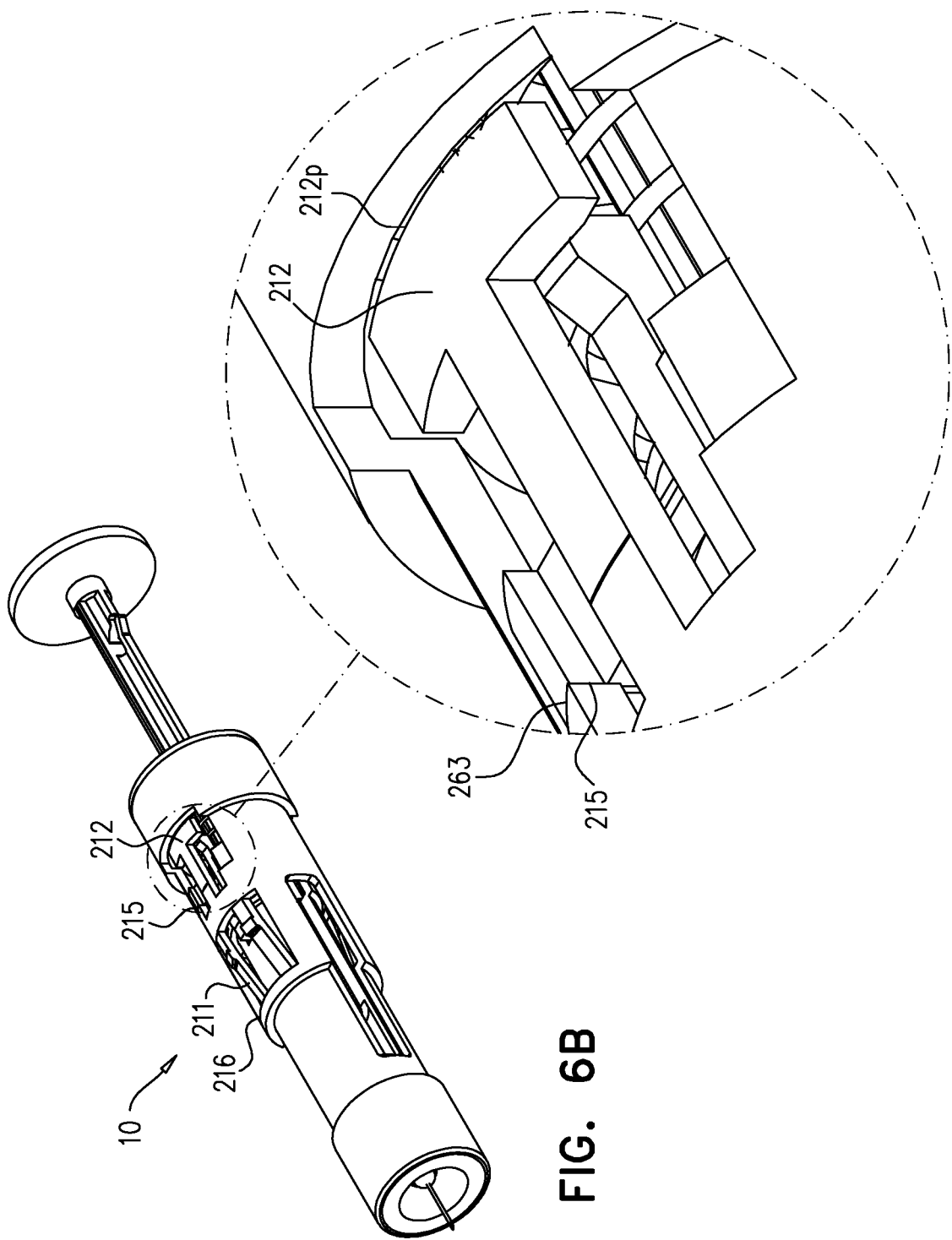

Syringe stop 215 of main housing 210 is described in relation to FIGS. 6A and 6B, as stopping movement of syringe-support 260 and syringe 100 in the needle penetration state.

Lower locking arms 211 are described in relation to FIG. 8 as interacting with the needle shield 220 (via ribs 228 of needle shield) after injection is complete, to hold needle shield in final fully extended position and prevent needle sticks during handling after use.

Figure 1B:
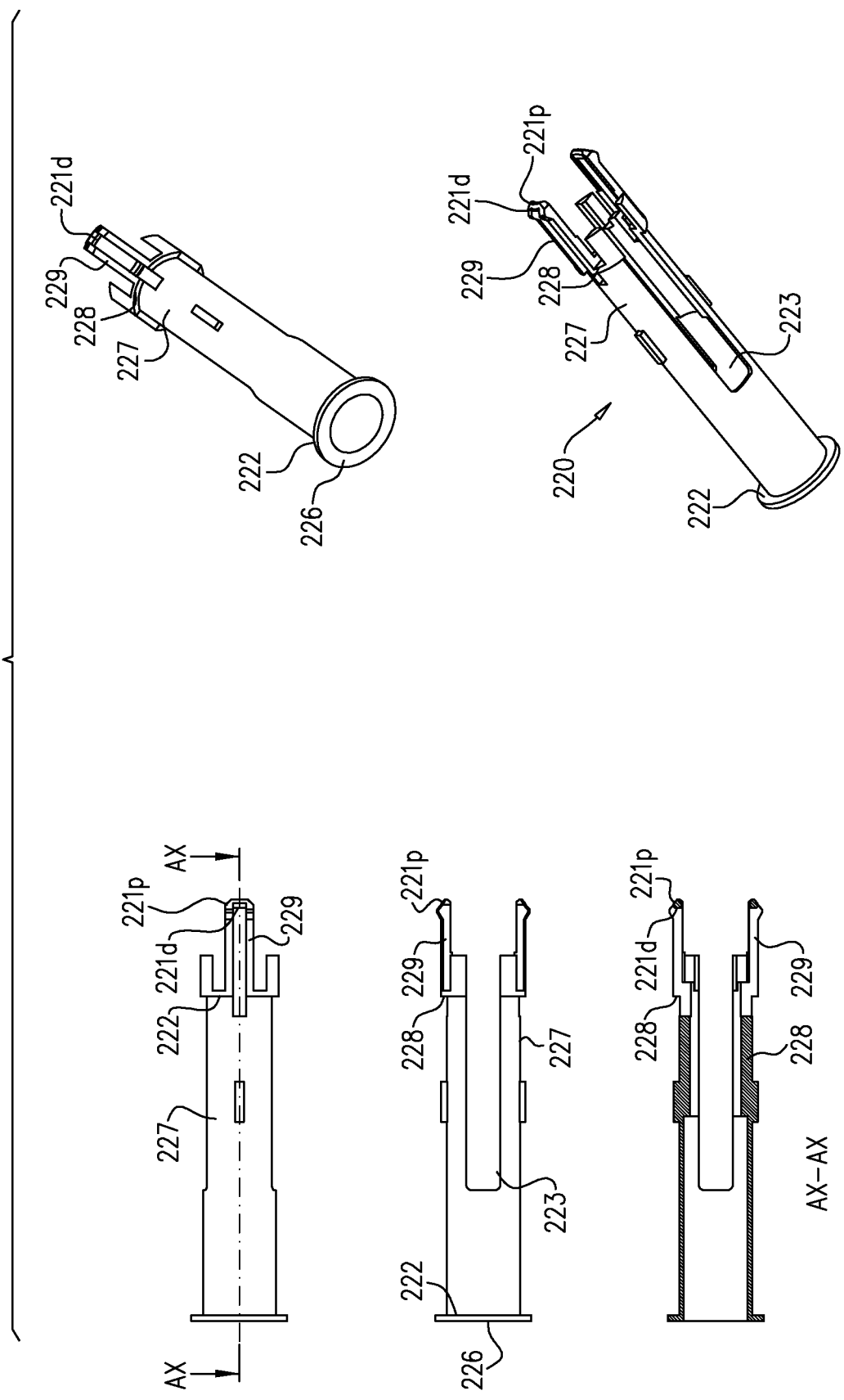

Referring now to FIG. 1B, needle shield 220 comprises rearward facing arms 229 which terminate in rib distal sides 221d and proximal facing tapers 221p. These elements (229, 221d) interact with the syringe-support 260 (not shown) to prevent premature distal movement of the needle shield (described in FIG. 2A). Additionally, during needle penetration, the rearward facing arms 229 and proximal facing tapers 221p force release of T-shaped locking arms 212 of the main housing (described in FIG. 4A).

In addition, needle shield 220 preferably comprises a generally tubular body portion 227 and spring seat 222 against which the needle shield spring 250 abuts (spring not shown).

Note rib 228 of needle shield 220 (best shown in isometric view at far right, and in side view bottom center) which acts to distally limit movement of needle shield 220 in fully extended position after use.

Referring now to FIG. 1C, an NS remover 240 is illustrated, which allows easy removal of the NS (Needle Sheath) to ready the device for injection.

Note (in isometric views), snap teeth 241 formed in the inner portion 245 of the NS remover 240. When a prefilled syringe (not shown) is inserted into the device, the snap teeth 241 engage with and irreversibly hold the proximal rigid rim 112 of the NS (shown in FIG. 1G, 3A). The NS remover 240 allows a user to grip and apply sufficient force to remove the NS, without distorting the needle.

Bumpers 243 can receive and dampen any axial load or shock applied on them, when the device is accidentally dropped, as bumpers 243 are located on the most distal (prominent) end of the device. The axial load or shock is transmitted to the flexible connection arms 242 which dampen the axial load or shock and thus limit the force transmitted to the inner portion 245 of the NS remover 240. This dampening reduces chances of breakage of the syringe barrel 140 and/or its flange 120, in cases the syringe barrel is made of glass (shown in FIG. 1G).

Note that any number of flexible connection arms 242 can be provided, in any shape that will provide flexible axial positioning between inner portion 245 and the gripping face 244 which is an outer area of the NS Remover 240.

Axial stoppers 246 are one or more protrusions, which prevent distal disengagement of the NS 110 from the NS remover 240 following removal of the NS remover. It can be understood that such axial stoppers can be produced by protrusions as shown, ribs, or any other shape.

Figure 1D:
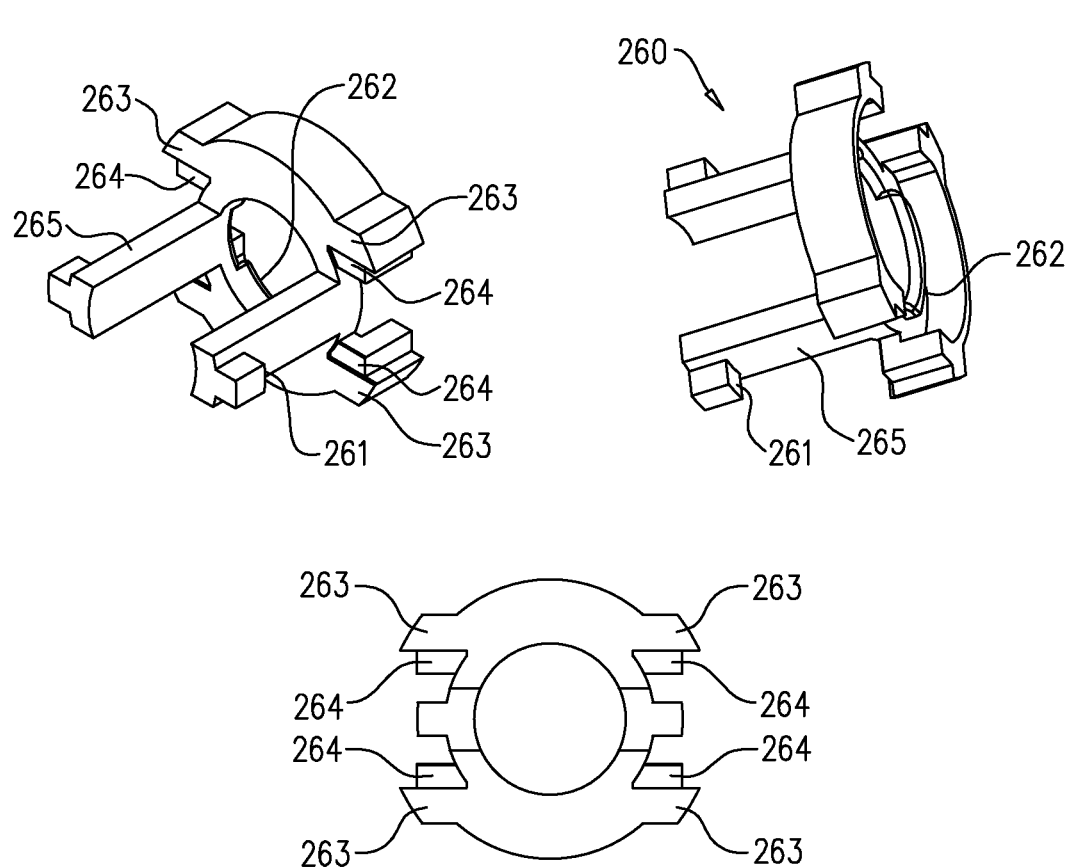

Referring now to FIG. 1D, syringe-support 260 receives and supports the proximal end of the prefilled syringe 100. The barrel of the prefilled syringe 100 is inserted into the central lumen of the support, and the flange of the syringe (shown as 120 in FIG. 1G) is supported distally and radially by the syringe seat 262.

Protrusion 261 interacts with the needle shield 220 to prevent the needle shield 220 from prematurely advancing distally and prematurely triggering a needle prick. This is enlarged upon below in relation to FIG. 2A.

Referring to the upper left view of FIG. 1D, syringe-support edge 263 plays a role in controlling the extent of penetration of the needle to the outermost limit where needle penetration is considered complete, as described in relation to FIG. 6A.

Figure 1E:
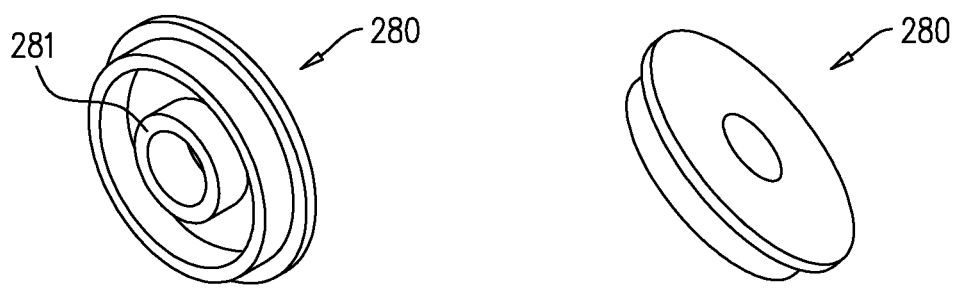

Referring to FIG. 1E, rear cap 280 is shown. Rear cap 280 has a hollow center through which the plunger rod enters.

Lock bracket 281 of the rear cap interacts with a front locking segment on the plunger rod (291 in FIG. 1F), to prevent a user from pulling and hyper-extending the plunger instead of pressing it. (Described in relation to FIG. 2B).

Figure 1F:
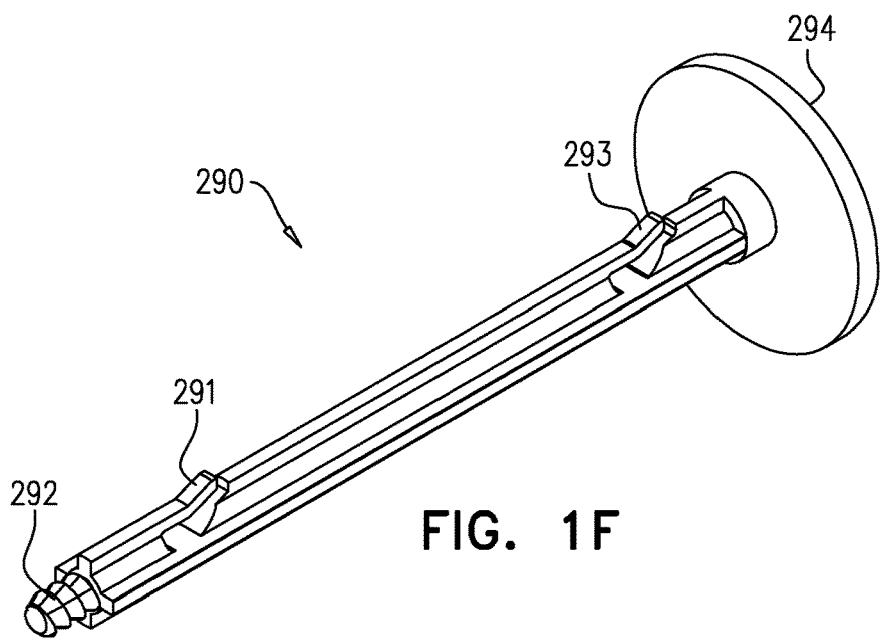

Referring now to FIG. 1F, the plunger rod 290 includes a forward facing tip 292 which engages a piston of prefilled syringe 100 (not shown). A plunger back end 294 needs to be pressed by a user to advance the piston and inject medication present in the prefilled syringe 100.

A front locking segment 291 is a tab which prevents a user from pulling and hyper-extending the plunger instead of pressing it, as such action will thrust the front locking segment 291 against the lock bracket 281 of the rear cap 280, stopping hyper-extension of the plunger 290. The front locking segment 291 is flexible to allow it to pass through the syringe barrel 140 during injection.

An additional tab, termed the rear locking segment 293, similarly prevents extension of the plunger by a user (as the plunger should only be pressed and not extended). The rear locking segment 293 flexibly passes through the lock bracket 281 of the rear cap 280 when the plunger 290 is pressed.

It can be understood that any number of locking segments (such as 291 and 293) can be provided. Additional locking segments along the plunger rod 290 can provide additional stops for preventing residual fluid spill out of the syringe barrel 140 if the piston is disengaged from the barrel. Alternatively, the plunger rod 290 can be produced without any such locking elements, or with only one of them.

Figure 1G:
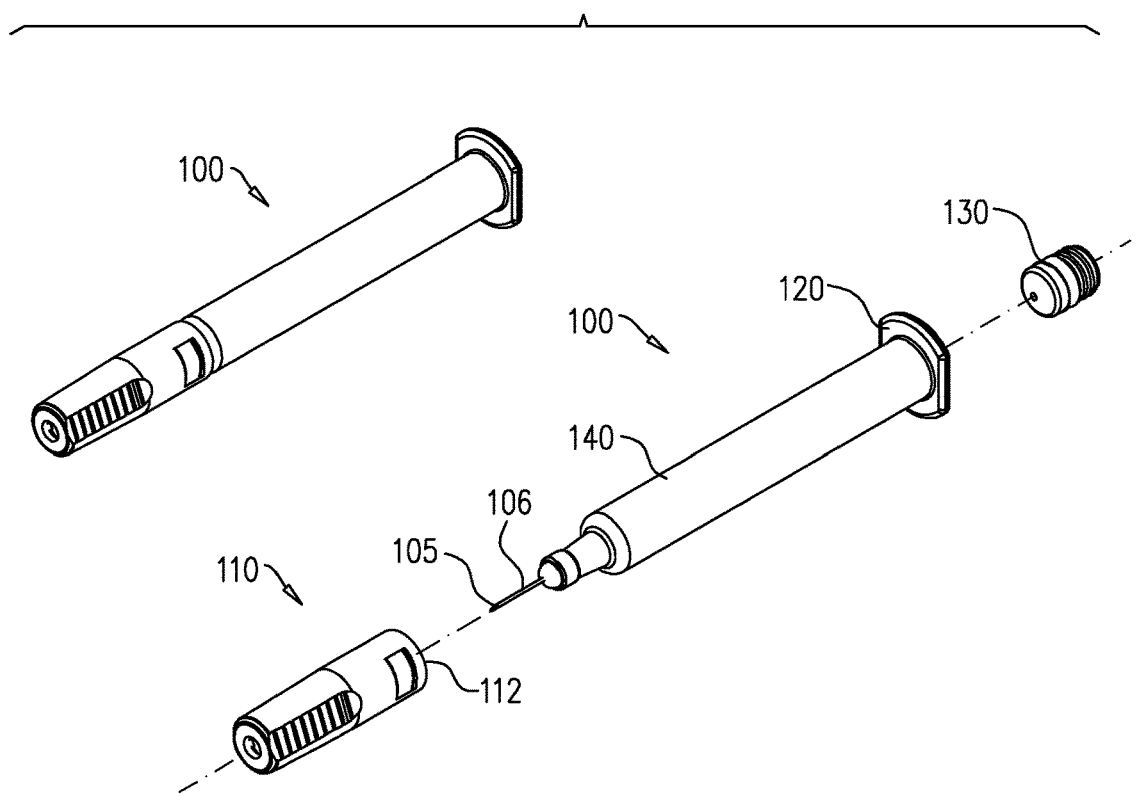

Referring to FIG. 1G, a prefilled syringe 100 is shown, comprising a syringe barrel 140 which includes a flange 120, a piston 130, a needle 106 with a needle tip 105, and a rigid needle sheath (NS) 110 which conceals the needle tip 105. The NS 110 can be a rigid or a soft needle sheath.

Note the proximal rigid rim 112 of the NS which engages irreversibly with the snap teeth 241 of the NS remover (not shown), allowing removal of the NS prior to use of the device.

Figure 2A:
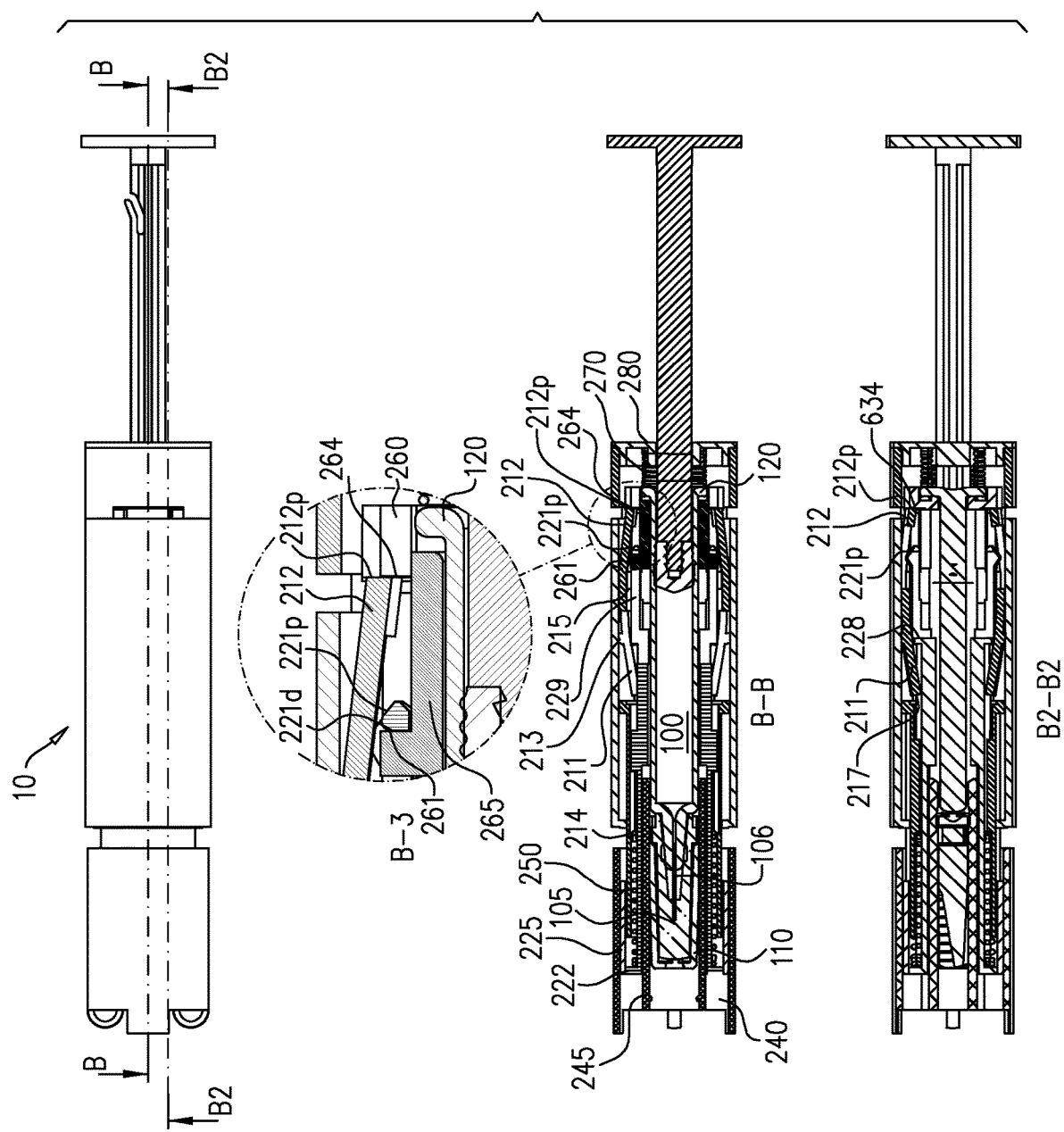
Figure 2B:
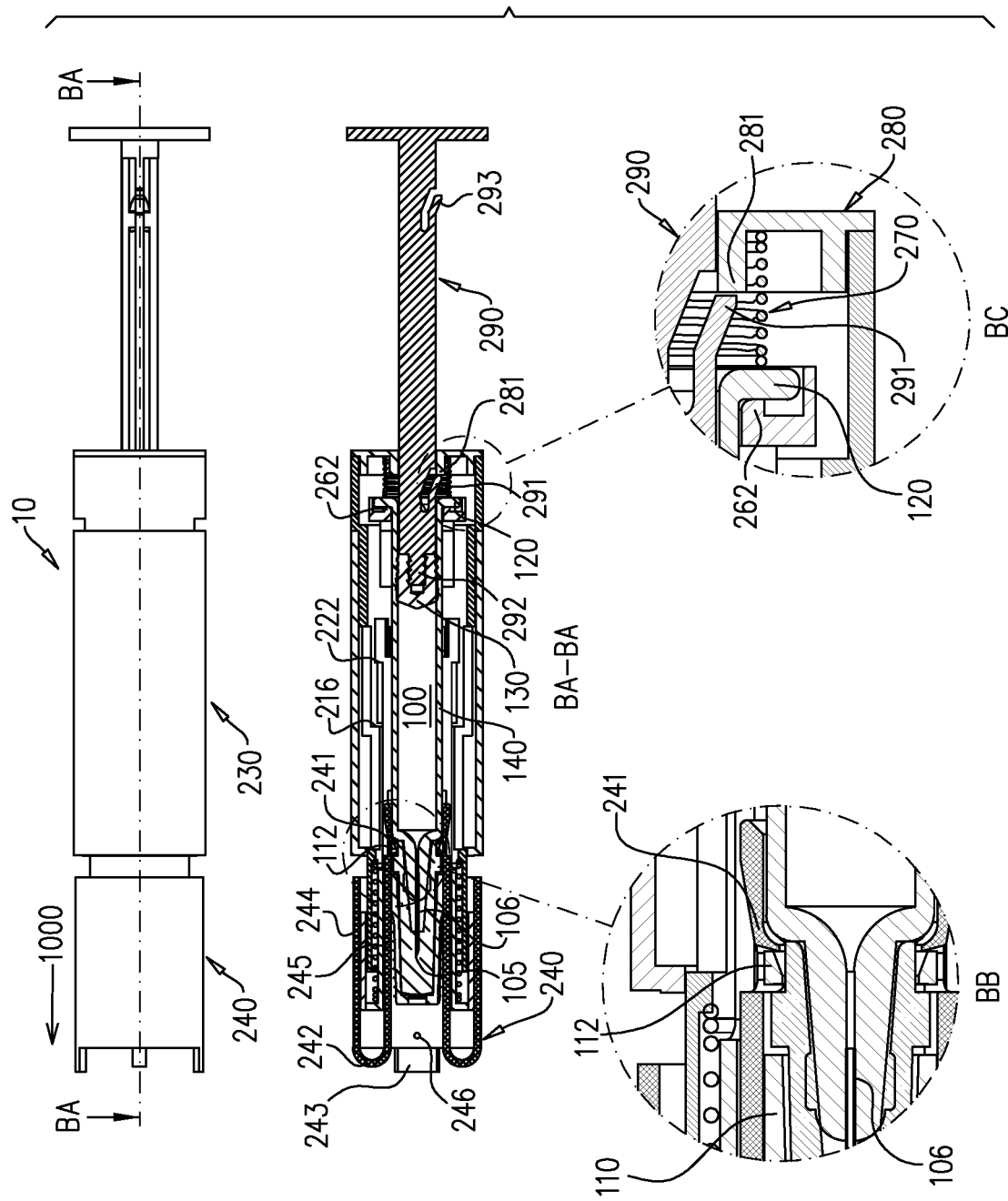

Referring to FIGS. 2A and 2B, the Safe Auto-Needle (SAN-P) of the invention is shown, in its fully assembled storage state.

The syringe spring 270 is supported on the rear cap 280 and distally on the flange 120 of the prefilled syringe 100.

In another embodiment (not shown), there are one or more elements which separate between the distal side of syringe spring 270 and flange 120.

The NS remover 240 preferably covers the needle shield front 225, and is engaged to the NS 110 which conceals the needle 106 including the needle tip 105 of the prefilled syringe 100. The NS remover 240 also prevents access to the needle shield 220, and thus prevents accidental pressing on the needle shield and its movement in the proximal direction, which would result in premature needle penetration.

The outer cover 230 is mounted on the main housing 210, and is fixed by any method of bonding, welding, one or more snaps, etc. Outer cover 230 is preferably made of transparent or clear material, but it may be formed with one or more viewing through windows to allow viewing of the contents of the prefilled syringe 100. Alternatively, outer cover 230 can be made of an opaque material, e.g., in cases where there is no need to view the contents of the prefilled syringe 100.

In FIG. 2B, enlargement BB, the snap teeth 241 of the NS remover 240 have engaged with and grip the proximal rigid rim 112 of the NS 110, to allow effortless removal of the NS using the NS remover 240.

The NS remover bumpers 243 of NS remover 240 receive potential axial load or shock applied on it, this dampening reduces chances for breakage of the syringe barrel 140 and/or its flange 120. The syringe spring 270 provides additional damping further reducing chances for breakage of the syringe barrel 140 and/or it's flange 120.

The plunger rod 290 is engaged with the piston 130 at its forward facing tip 292. This engagement can be of any form, such as a screw as shown, as a snap-fit, or any other suitable form.

Referring to FIG. 2B, enlargement BC, unidirectional movement of plunger 290 in correct orientation is ensured, as follows: plunger rod front locking segment 291 prevents the piston 130 from being pulled out from prefilled syringe 100, by colliding with plunger rod lock bracket 281 of rear cap 280. The plunger rod front locking segment 291 is flexible to allow it to pass through the syringe barrel 140 during injection.

The syringe spring 270 urges the prefilled syringe 100 and the syringe-support 260 distally. The flange 120 of syringe barrel 140 of prefilled syringe 100 is supported distally and radially on the syringe seat 262 of syringe-support 260.

Referring back to FIG. 2A, cross-sectional View B-B, the needle shield spring 250 is supported proximally on the spring seat 214 of main housing 210. The needle shield spring 250 urges the needle shield 220 distally by pushing on the needle shield spring seat 222.

Referring to Enlargement B-3, rib distal sides 221d, and proximal facing tapers 221p, of needle shield 220 interact with protrusion 261 of the syringe-support 260 to prevent premature distal movement of the needle shield 220.

The T-shaped lock arms 212 of the main housing 210 oppose the syringe-support 260 which holds the prefilled syringe 100, thus preventing syringe from prematurely advancing distally.

As best seen in FIG. 2B, Cross-Sectional View BA-BA, the NS remover 240 is shown in the device, after the snap teeth 241 have engaged with the NS 110. A user may now utilize the NS remover 240 to effortlessly remove the NS; the NS remover 240 assures that the needle tip (not shown) will not be bent by the forces applied.

Additionally, gripping face 244 is an outer area of the NS remover. An axial load applied by the user on the NS remover gripping face 244 in the direction shown by arrow 1000, will remove the NS 110, as the NS remover snap teeth 241 have engaged with and grasp the NS distal rigid rim 112 of the NS 110.

One or more NS remover snap teeth 241 may be provided.

In order to protect the Needle 106 from damage, during removal of the NS remover 240 and the NS 110, the inner portion 245 of the NS remover 240 is guided axially within the needle shield 210 (best seen in cross sectional views B-B in FIG. 2A and BA-BA in FIG. 2B), thus preventing any bending load on the needle 106.

Figure 3A:
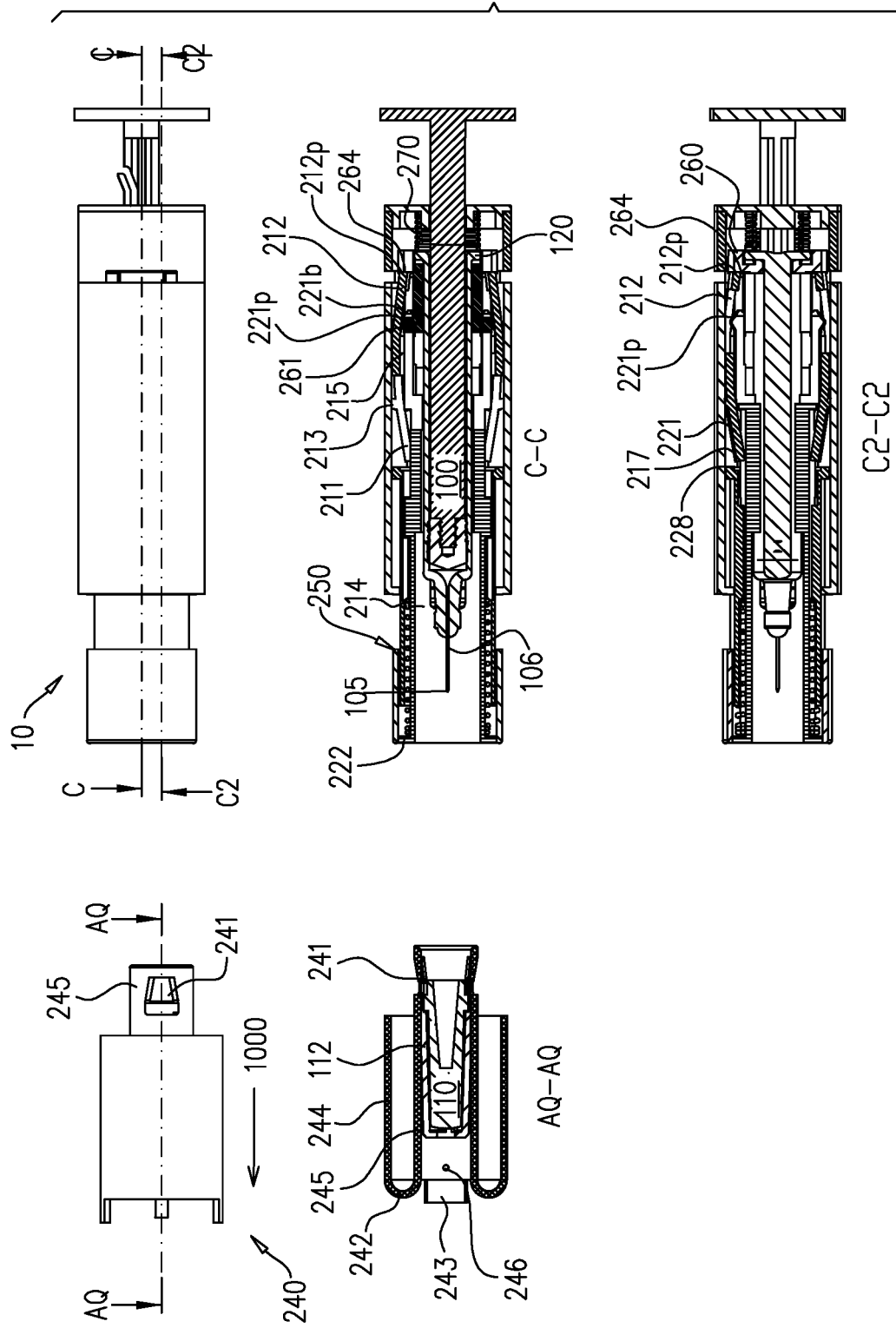

Referring to FIG. 3A, the device 10 is shown after removal of the NS. No additional changes have occurred in the positioning of other components of the device 10.

The needle 106 remains essentially hidden throughout this stage.

The NS remover 240 includes one or more protrusions termed "axial stoppers" 246, which prevent distal disengagement of the NS 110 from the NS remover 240 following removal. It can be understood that such axial stoppers can be protrusions as shown, ribs, or may have any other shape.

Figure 3B:
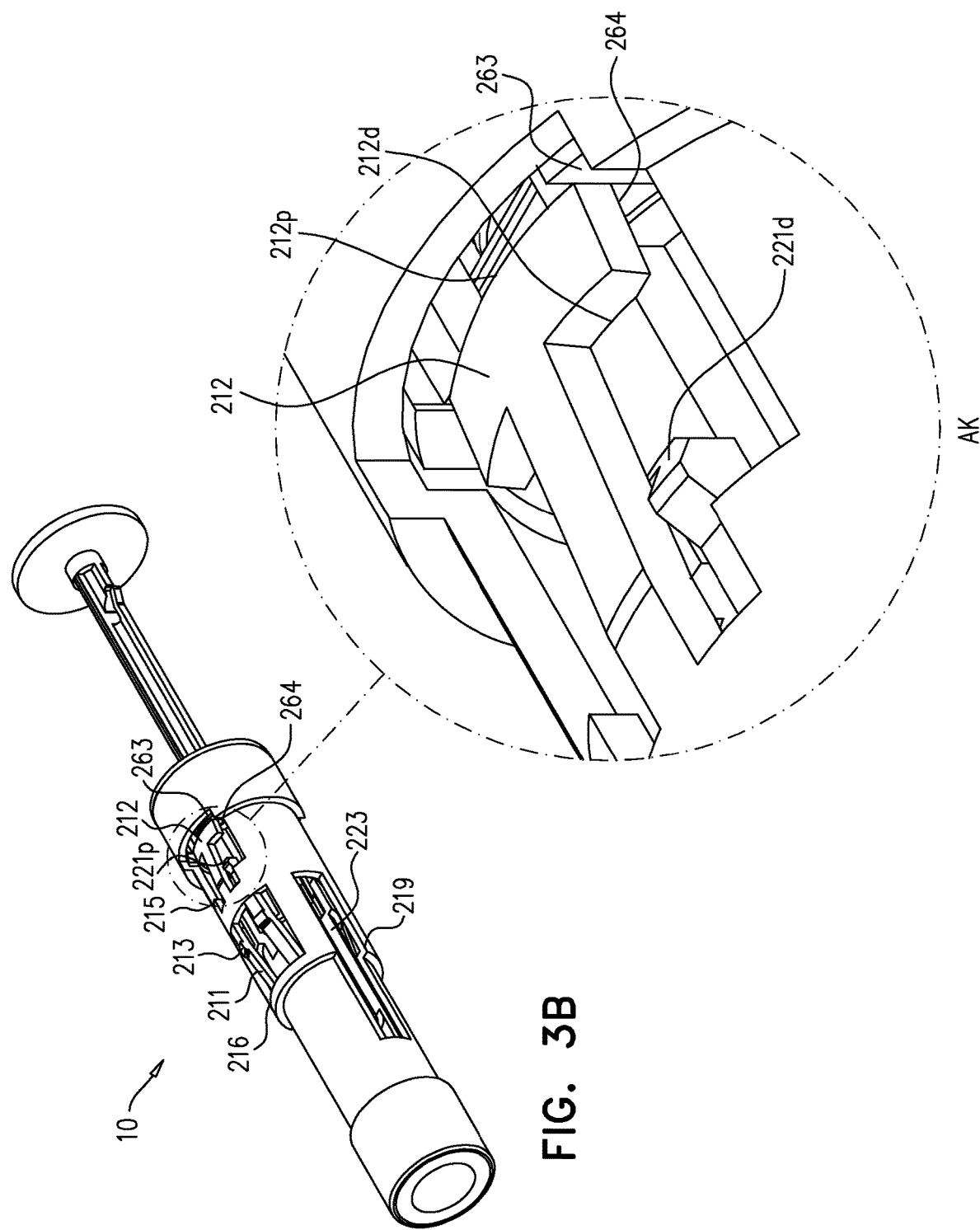

Referring to FIG. 3B, an isometric view of the device 10 is shown, after removal of the NS. Outer cover 230 has been removed from this view to allow view of inner components.

In Enlargement AK, the T-shaped locking arms 212 of the main housing 210 are pressed upon front facing surfaces 264 of the syringe-support 260, prevent prefilled syringe 100 from prematurely advancing distally before the injection process is initiated.

The Viewing window 223 of needle shield 220 and the viewing window 219 of the main housing 210 are shown, which together with a transparent/clear outer cover 230 (not shown) allow a user to view the medicament prior to injection, to ensure unfavorable changes in the drug appearance have not occurred (such as sedimentation or cloudiness) which could indicate decomposition of the drug.

Figure 4B:
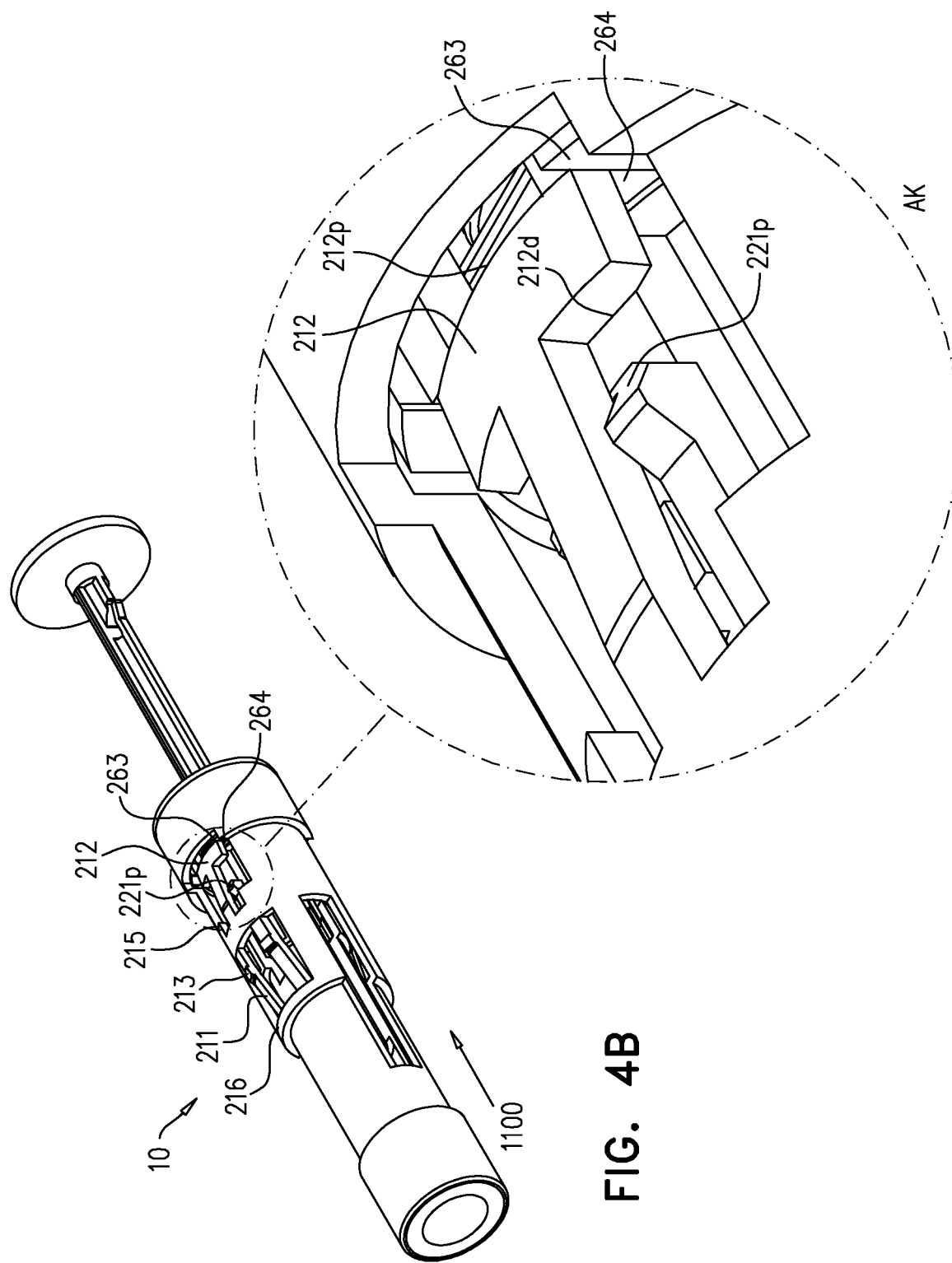

Referring now to FIGS. 4A and 4B, a user now triggers the beginning of the injection process, by pressing the distal end of the device 10 upon an exposed injection site (shown pressed only half-way).

In the left illustration of FIG. 4A, when the needle shield distal end 226 is pressed in the direction indicated by arrow 1050, against the injection site 5000, this forces the needle shield 220 to move proximally indicated by arrow 1100, thus triggering exposure of the needle tip.

Release of the needle shield 220 occurs as follows:

In FIG. 4A, Central Drawing D-D and Enlargement A-3, pressure upon the injection site compresses the needle shield spring 250, urging the needle shield 220 proximally in direction 1100. This movement then results in the proximal facing tapers 221p of the rearward facing arms 229 of the needle shield 220, contacting the inner side of the T-shaped locking arms 212 of the main housing 210. This lifts the T-shaped locking arms 212 radially outwardly towards directions 1200.

Note in Enlargement A-3 the position of proximal facing tapers 221p relative to T-shaped locking arms 212. Proximal facing tapers 221p has moved proximally towards the terminal end 212p of T-shaped locking arms. Proximal facing tapers 221p allows T-shaped locking arms 212 to slide upon the slope of proximal facing tapers 221p with minimal friction, and T-shaped locking arms are lifted outwards.

In comparison, refer back to FIG. 2A, Enlargement B-3, to see initial storage position of rib distal side 221d compared to T-shaped locking arms 212. Rib distal side 221d is considerably more distally located than in FIG. 4A.

Referring to FIG. 4B, an isometric view is shown of this stage (initial triggering), shown without outer cover 230 and without the injection site.

In Enlargement AK of FIG. 4B, note positioning of proximal facing tapers 221p relative to T-shaped locking arms 212. Proximal facing tapers 221p has moved proximally towards the T-branch of terminal end 212p. During proximal movement of the proximal facing tapers 221p they contact T-shaped locking arms 212 and lift them radially outwardly.

Referring now to FIG. 5A, needle shield 220 has moved proximally to the full extent, lifting of T-shaped locking arms 212 outwardly, releasing the syringe-support 260, to allow movement of the syringe-support 260 which will result in needle penetration. (Needle has not yet penetrated at this stage).

Note in Enlargement A-3, the T-shaped locking arms 212 are now illustrated generally parallel to the longitudinal axis of the SAN-P 10 after they have been lifted.

In Cross Sectional View E-E, the needle shield spring seat 222 of the needle shield 220 acts as hard stop against the front edge 218 of the main housing 210 preventing the needle shield 220 from moving further proximally.

Figure 5B:
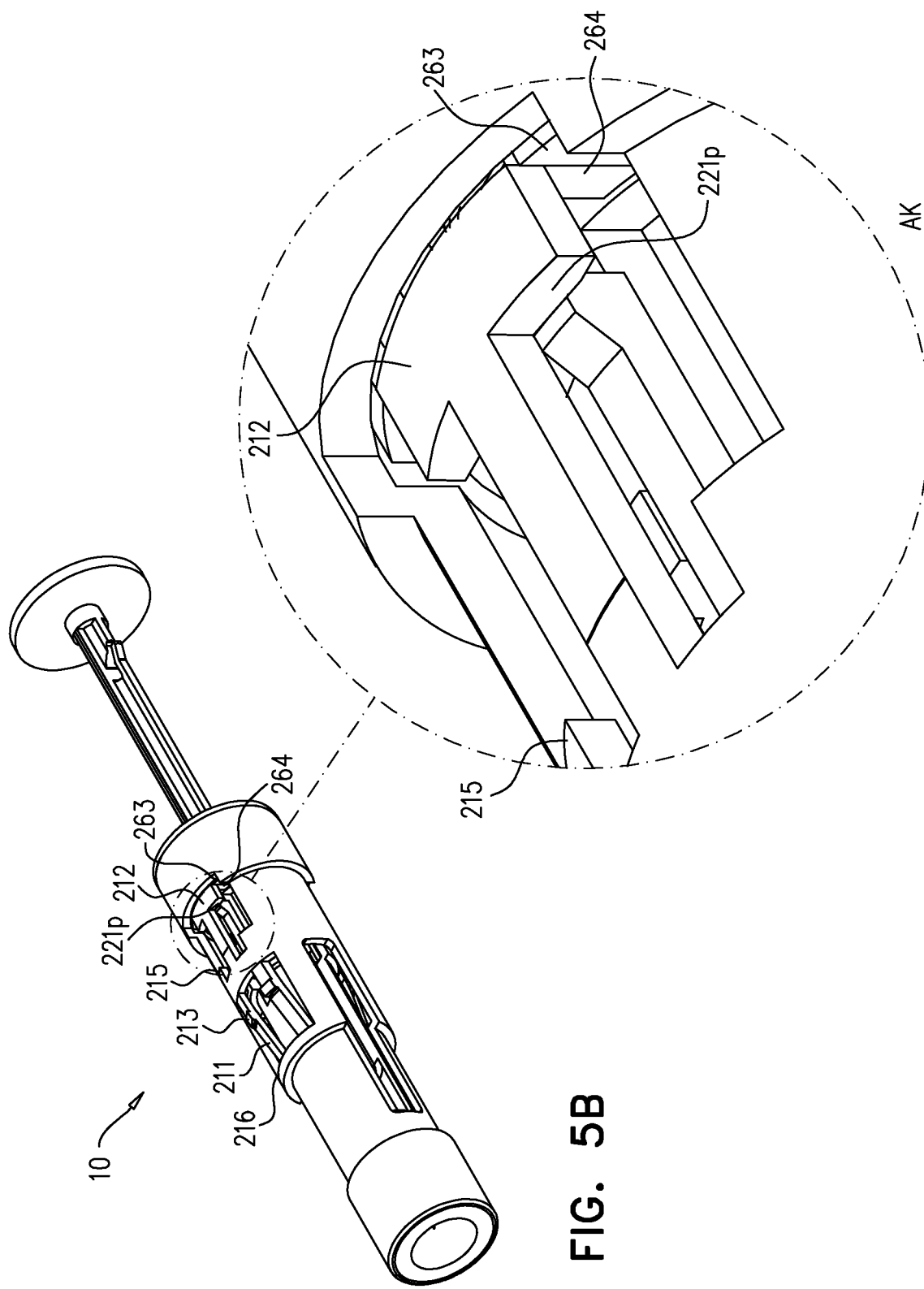

Referring to FIG. 5B, the SAN-P device 10 is shown in an isometric view; without the outer cover 230 and without the injection site 5000. Needle has not yet penetrated at this stage.

Note in Enlargement AK of FIG. 5B, the maximally proximal position of proximal facing tapers 221p of needle shield 220, relative to T-shaped locking arms 212.

Referring now to FIG. 6A, needle penetration is shown, resulting from rapid distal movement of syringe-support 260 together with the prefilled syringe 100.

The syringe-support 260 was urged towards the injection site by the syringe spring 270.

In Enlargement A-3, the syringe-support 260 progressed distally until its movement is stopped when the syringe-support edge 263 of syringe-support 260 abuts the syringe stop 215 of the main housing 210.

At this stage, the needle tip 105 of the prefilled syringe 100 has penetrated into the appropriate depth at the injection site 5000. The needle shield is located in its second position, in which the needle is at least partially exposed.

Referring to FIG. 6B, the device 10 is shown in isometric view after needle penetration, (without cover 230, and without injection site).

Figure 7:
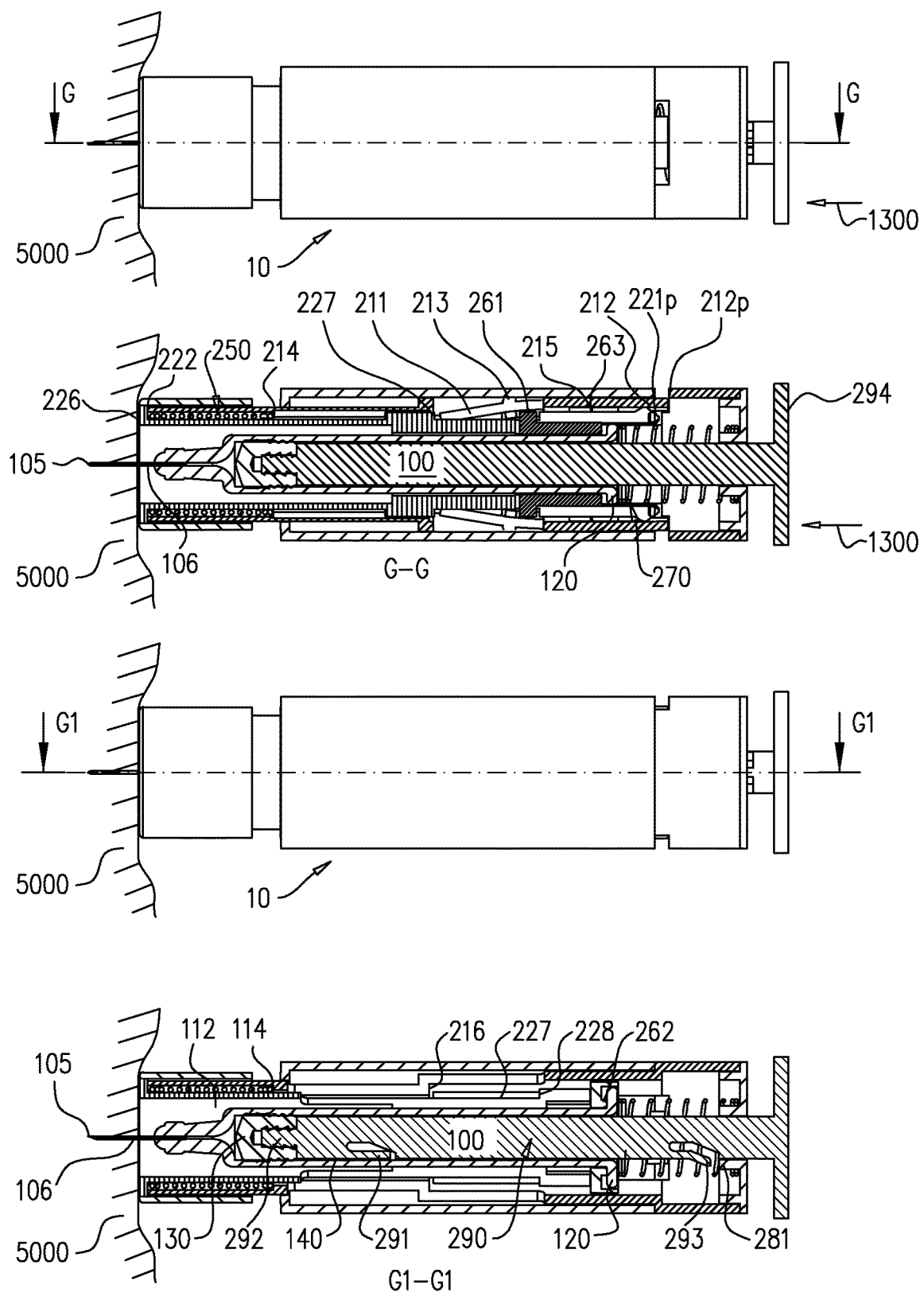

Referring to FIG. 7, after needle penetration, the user now presses the plunger to inject the medication.

The rate of injection may be manually controlled by the user, who controls the force he applies when pressing the plunger. This avoids the pain associated with too rapid injection, especially known to occur with too rapid injection of viscous materials, or of medicaments having lipid delivery vehicles.

In upper two drawings of FIG. 7, the user has pressed the plunger rod flange 294 maximally, and the plunger rod 290 has moved distally as indicated by arrow 1300. This advances the piston 130 maximally, which injects the fluid medicament via needle tip 105.

Referring to Cross-Section G1-G1 (lowest on FIG. 7), the front locking segment 291 of plunger rod 290, has flexibly bent inwardly upon its entry into the syringe barrel 140.

At the end of the injection, the piston 130 will reach the end of the syringe barrel 140 and stop, thus indicating to the user that the injection is complete.

Referring still to Cross-Section G1-G1, the rear locking segment 293 of plunger rod 290, has flexibly passed through the lock bracket 281 of the rear cap 280.

In this location, the rear locking segment 293 opposes the lock bracket 281, thus preventing a user from extending back the plunger rod 290 through the rear cap 280 in the proximal direction (which would result in drawing fluid from the injection site, back into the syringe).

Any number of locking segments 291 and 293 can be provided, or locking segments can be eliminated. Additional locking segments along the plunger rod 290 can provide additional backward stops for preventing residual fluid spill out of the syringe barrel if the piston 130 is disengaged from the syringe barrel 140.

Furthermore, to eliminate such potential spill out of residual fluid that may be toxic, a plunger rod lock can be added, and can be activated depending on the relative position of the plunger rod to the needle shield, the prefilled syringe, the housing or any other part.

Referring to FIG. 8, injection has been completed and the device is shown in its "discard" state after removal of the SAN-P device 10 from the injection site. In this state, inadvertent needle pricks are prevented during handling for discard, since the needle shield is locked in its third position in which the needle shield is fully extended, hiding the needle tip. The needle is now irreversibly concealed by the needle sheath.

Referring to Cross-Section H-H of FIG. 8, removing the SAN-P device 10 from the injection site results in the needle shield 220 automatically moving distally relative to the main housing 210, urged by the expansion of needle shield spring 250. The distal movement of the needle shield 220 is stopped/limited by rib 228 of the needle shield 220 contacting stopper 216 of main housing 210.

Referring to Cross-Section H1-H1 of FIG. 8, another section is shown illustrating the components that lock the device in its needle-shielded position, for discard.

Upon distal movement of the needle shield 220 (which occurred when the device was removed from the injection site), rib 228 of the needle shield 220, forces the lower locking arms 211 of the main housing 210 to bend outwardly, thus allowing rib 228 to pass the distal face 217 of the lower locking arms 211.

At this stage, the distal face 217 limits and prevents proximal movement of the needle shield 220, so that the needle tip 105 is covered and protected by the needle shield 220.

In this state, reuse and inadvertent needle-sticks cannot occur from a used needle.

Referring to FIGS. 9-16, another embodiment of the invention is described, having additional safety features to prevent a user from pressing the plunger and discharging the medicine before the needle has completely penetrated the injection site. An "interlock" element ensures this. Furthermore, a tri-component plunger is included that allows syringe movement for needle penetration without movement of the proximal plunger. Additionally, the tri-component plunger allows the user to start injection of the medication immediately after the needle insertion, without any "idle stroke" (floating movement) between the plunger components. Moreover, this tri-component plunger allows variable positioning of the piston relative to the SAN-P assembly, due to variable positioning of the piston in the syringe caused by drug filling tolerances. Slight movement of the piston that may occur in response to changes in ambient pressure and temperature during storage, and, due to SAN-P components assembly tolerances.

Referring to FIG. 9, an exploded view is shown of Embodiment Two, having these additional safety features. Most of the central components are similar to those described hereinabove in relation to FIGS. 1-8. Novel aspects will now be described:

Rear cap 480 comprises grooves which end at locking faces 481 (enlarged in FIG. 10D), which engage with terminal fingers 612 of anterior plunger pusher 610 (best shown in FIG. 10F), and together with interlock 500, prevent premature pressing of the plunger pusher 610.

Plunger rod 290 previously described, has been replaced with anterior plunger pusher 610, proximal plunger 620 and distal plunger 630. To ensure above mentioned functionality of the plunger assembly and relative movement of the plunger components, unique one way ratchet teeth 632 may be seen on the end of distal plunger 630; these engage with ratchet teeth 622 on the proximal plunger 620 (best shown in FIGS. 10H and 10G; engagement and ratcheting described in FIG. 14).

Interlock 500 blocks pressing of the tri-component plunger (610,620,630) prematurely (before the needle had been deployed).

Syringe-support 460 is lengthened, including connection arms 461 which interact with the interlock 500 and with the anterior plunger pusher 610 (described in relation to FIG. 11B and more specifically detailed section view B11.1-B11.1 of FIG. 11B).

Referring still to FIG. 9, other central components of the SAN-P device 20, which remain essentially unchanged from the previous Embodiment (described in FIGS. 1-8), are shown: prefilled syringe 100, (previously shown in FIG. 1G), a main housing 410, a needle shield 420, an outer cover 430, an NS remover 240, (as previously shown as 240 in FIG. 1C), a needle shield spring 450, and a syringe spring 470.

Referring now to FIGS. 10A-10H, enlargements of the central components of the invention are presented, as follows:

FIG. 10A illustrates the main housing 410. Locking arms 412 of the main housing have replaced the T-shaped locking arms 212 described in the previous embodiment (FIGS. 1-8). The generally tubular rearward portion of the main housing 410 is longer than the generally tubular rearward portion of the main housing 210.

Figure 10B:
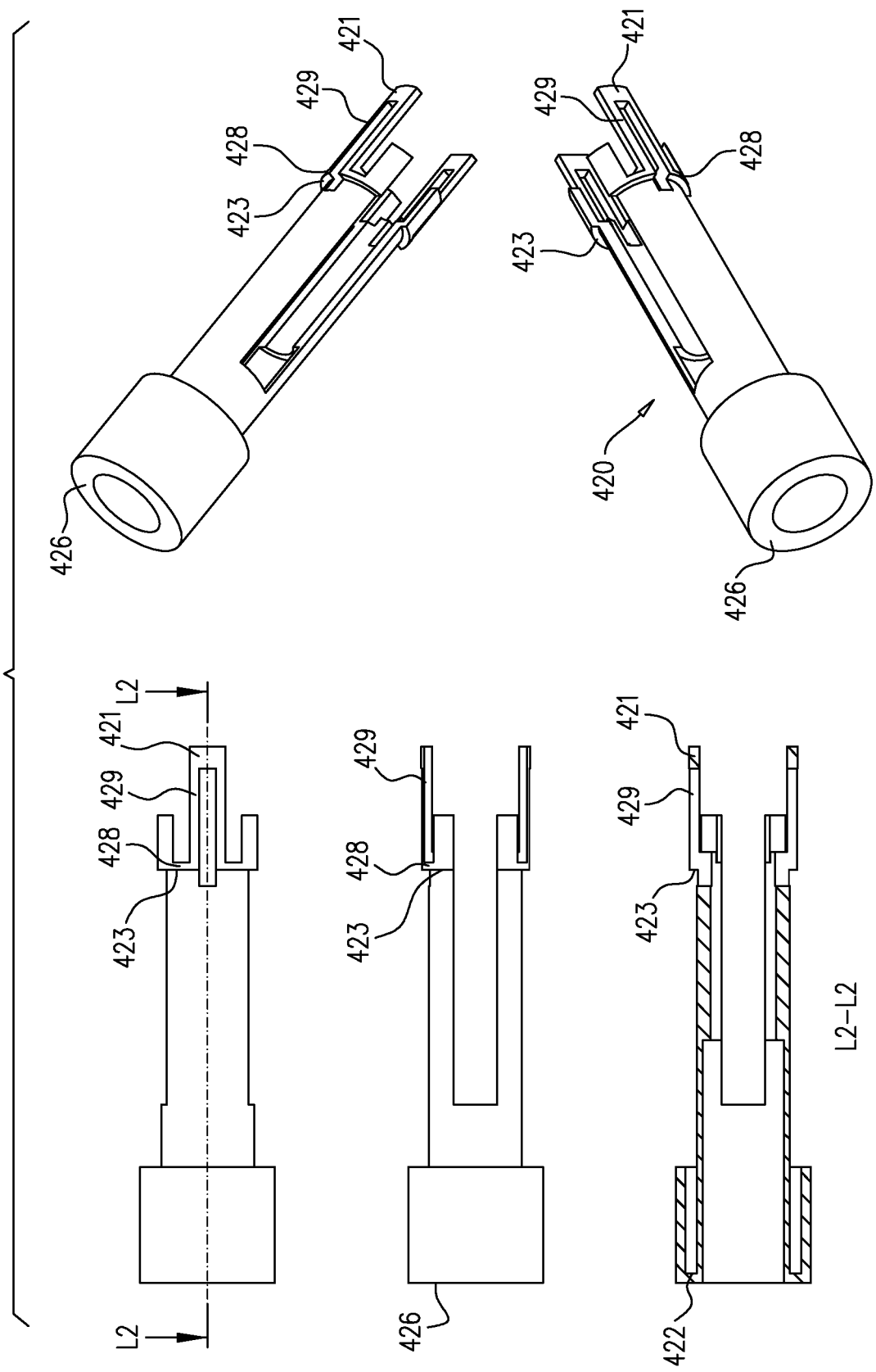

FIG. 10B illustrates the needle shield 420. Note rearward facing arms 429 including bridge 421.

Figure 10C:
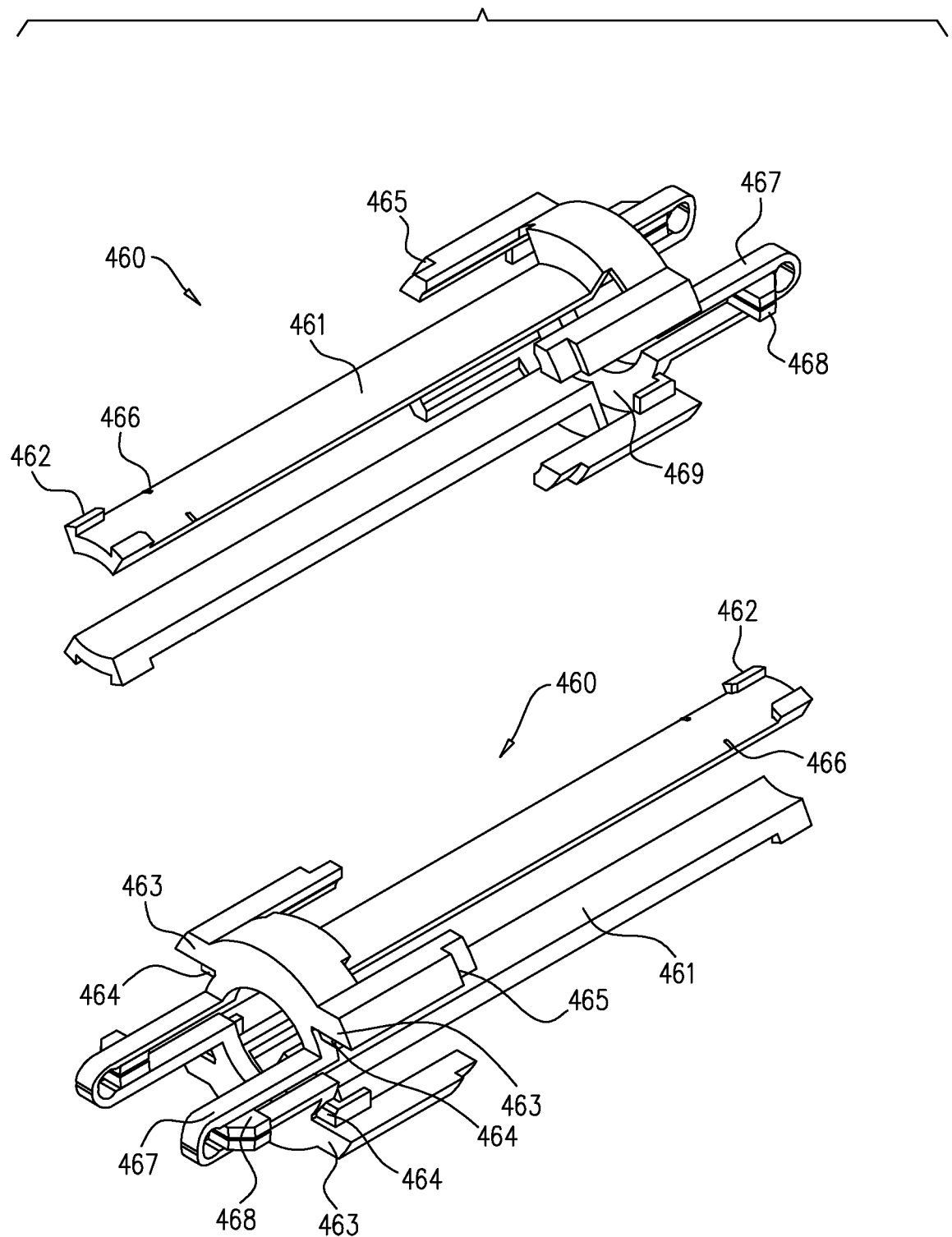

FIG. 10C illustrates the syringe-support 460. Protrusions 468 which extend from the beam 467 of the syringe-support 460, hold the distal side of bridge 421 of rearward facing arms 429 of the needle shield 420 (previously shown in FIG. 10B), preventing distal movement the needle shield 420 during storage (interaction shown in Enlargement 11a.2).

Referring still to FIG. 10C, protrusions 466, and ribs 462 are shown. The protrusions 466 support and limit distal movement of the interlock 500 until the injection procedure is triggered by a user.

Figure 10E:
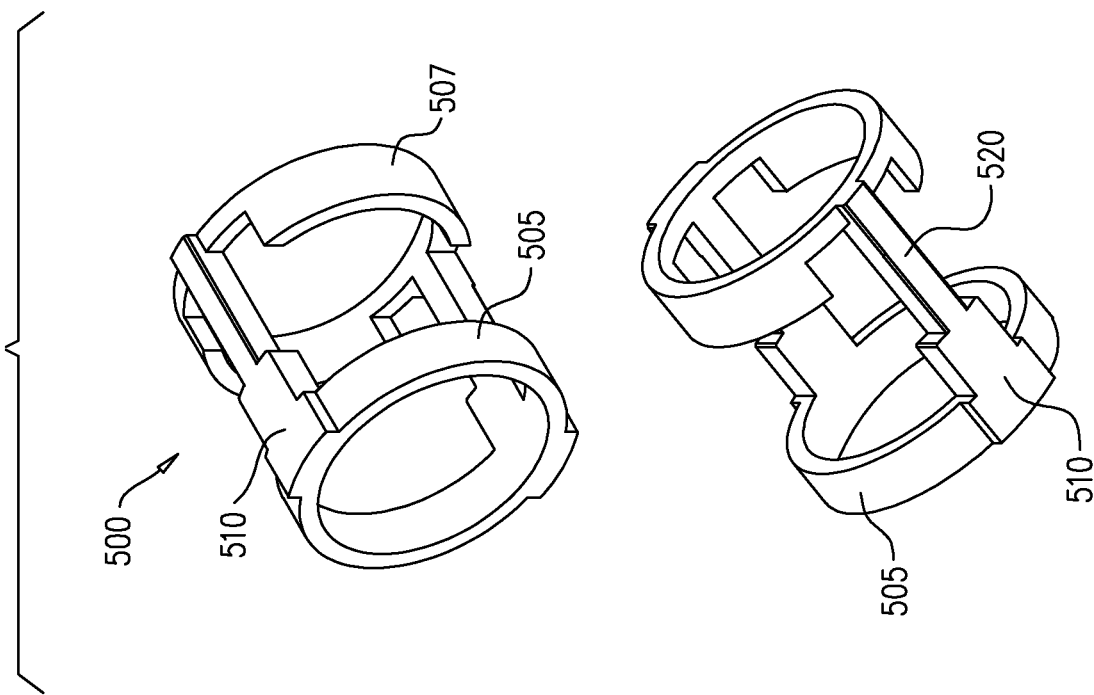
Figure 10D:
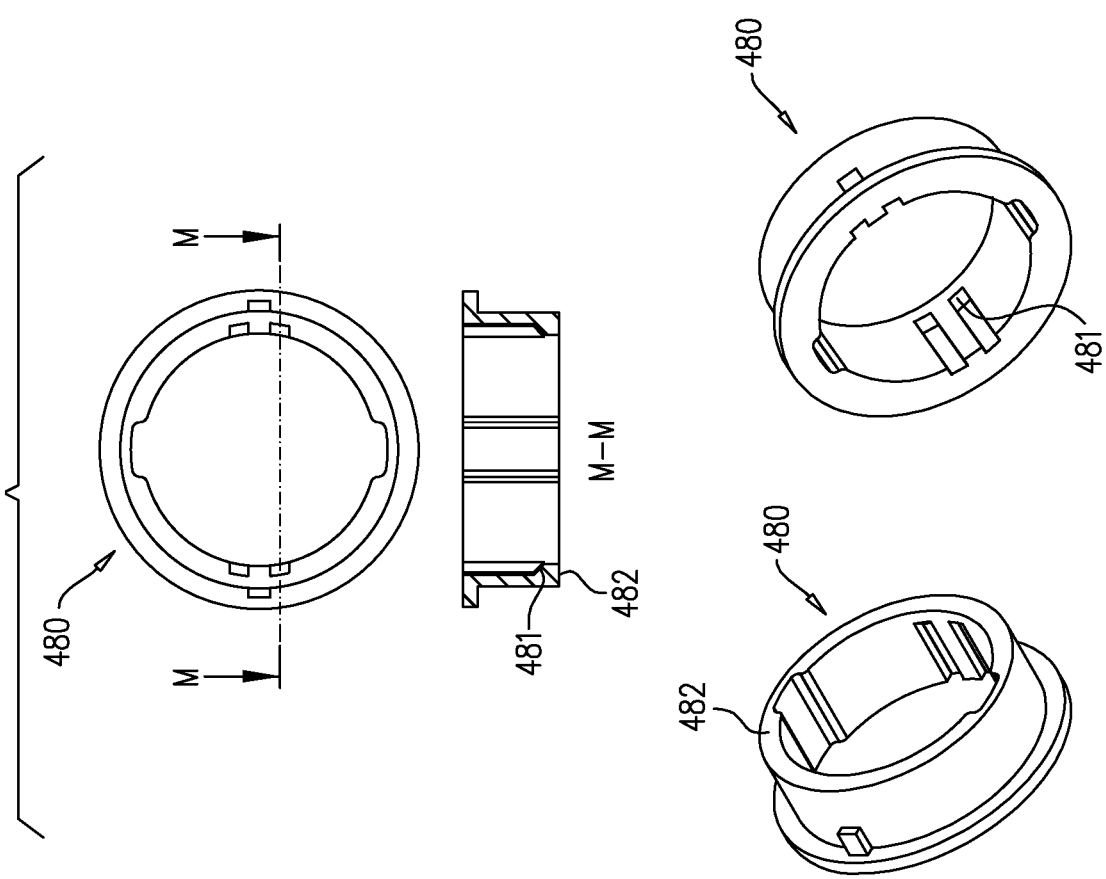

FIG. 10D illustrates the rear cap 480, which includes internal grooves ending with locking faces 481.

FIG. 10E illustrates the interlock 500, which includes an outwardly facing locking face 510, strut 520, and distal ring 505 and proximal ring 507.

Figure 10F:
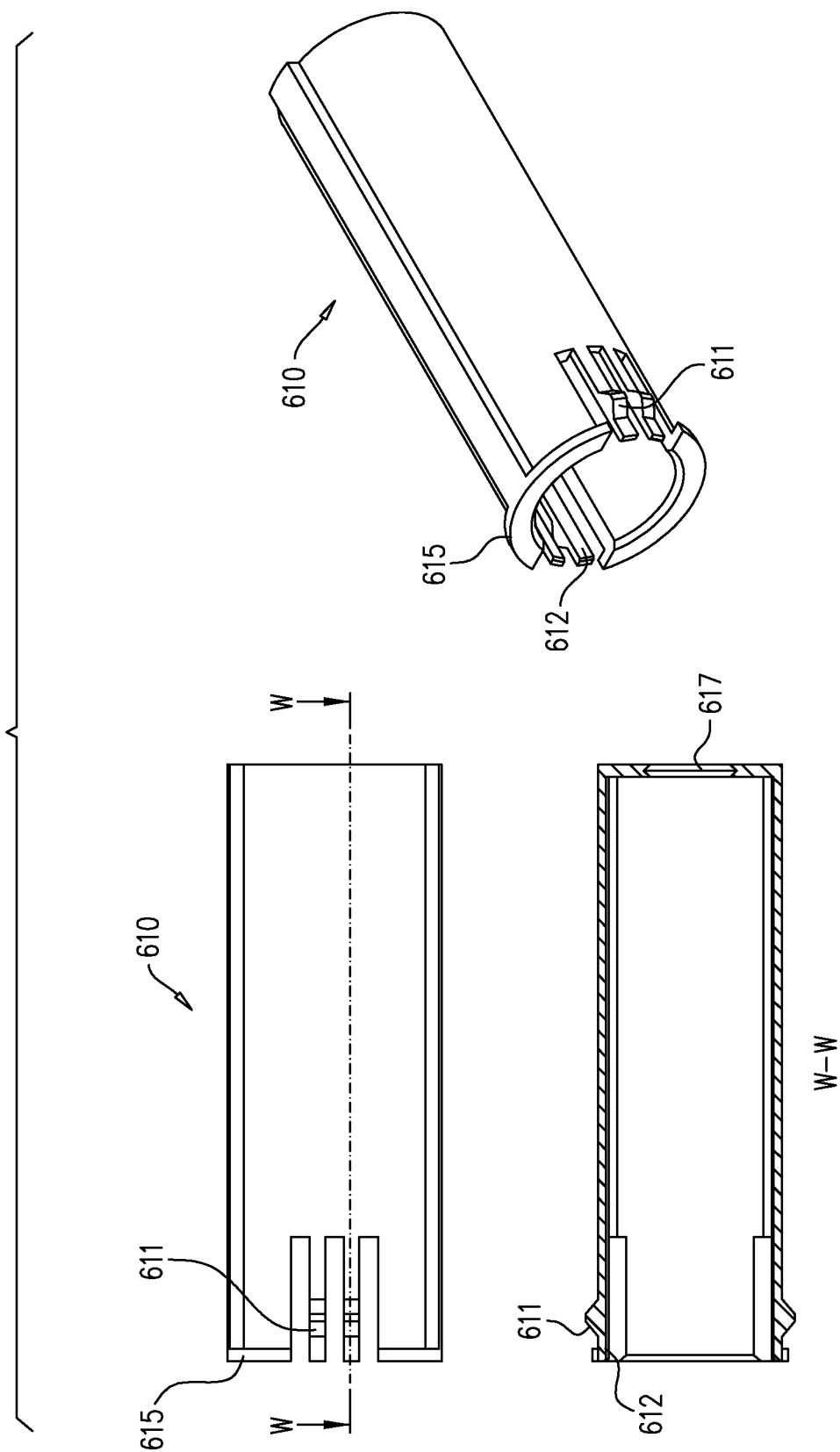

FIG. 10F illustrates the anterior plunger pusher 610, which is the most proximal component of the tri-component plunger. Terminal fingers 612 are shown, having locking face protrusions 611 extending there-from.

FIG. 10G illustrates the proximal plunger 620, the middle component of the tri-component plunger. The internal surface of flexible arms 625, defines angled ratchet teeth 622; angle is best seen in upper illustration. Ratchet teeth 622 are instrumental in guaranteeing one-way movement of the plunger (pressing of the plunger and not extension of the plunger), once they have engaged with corresponding ratchet teeth 632 of the distal plunger 630 (shown in FIG. 10H).

Note area between reference numerals 623 and 624. When ratchet teeth 632 of distal plunger (not shown) are present in this area, they are disengaged from ratchet teeth 622, allowing slight movement relative to one another, of the plunger components proximal plunger 620 and distal plunger 630. This slight movement may occur due to changes in ambient pressure and temperature during storage, which affects the amount of air present in the prefilled syringe, resulting in mild movement of the syringe piston 130. Point 623 is therefore defined as minimum air point 623, and point 624 is therefore defined as maximum air point 624 (reflecting the volume of air present at a given time within the prefilled syringe, and the relative position to which the distal plunger ratchet teeth will move according to this internal air pressure).

Ring 621 of the proximal plunger 620 snap-fits with the anterior plunger pusher 610 (via slot 617, not shown).

FIG. 10H illustrates the distal plunger 630, which is the third component of the tri-component plunger. Note outwardly facing angled ratchet teeth 632.

Figure 11A:
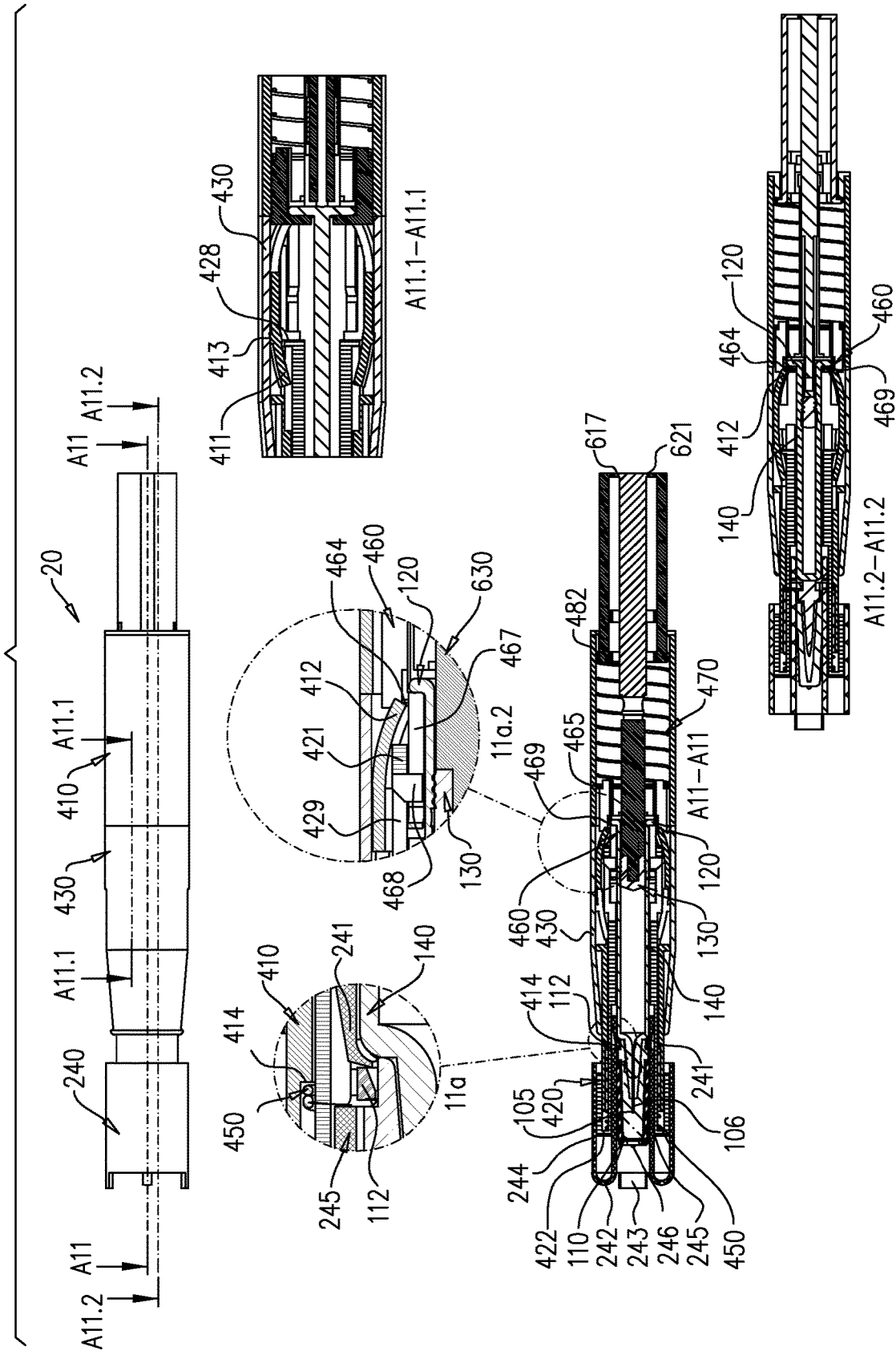

Distal Tip 633 connects to the syringe piston 130 (shown in FIG. 11A).

Referring now to FIGS. 11A and 11B, the SAN-P device 20 is shown in the storage position.

Referring now to FIG. 11A, and Enlargement 11a, the snap teeth 241 of the NS remover 240 have engaged with and grip the proximal rigid rim 112 of the NS 110 of the prefilled syringe 100.

The NS remover bumpers 243 receive potential axial load or shock when accidentally applied, as described herein above. Syringe spring 470 provides additional damping, further eliminating breakage of the syringe 100.

The syringe spring 470 is supported proximally on the distal face 482 of rear cap 480. The syringe spring 470 urges the syringe-support 460 distally by pushing on the spring seat 465 of the syringe-support 460.

In Enlargement 11a.2 (central enlargement), the locking arms 412 of the main housing 410 hold step 464 of the syringe-support 460, thus preventing the syringe-support 460 and the prefilled syringe 100 from moving distally.

In same Enlargement, the distal side of bridge 421 of rearward facing arms 429 of the needle shield 420 holds the needle shield 420 on the proximal side of protrusion 468 which extends from beam 467 of the syringe-support 460, thus bracing the needle shield 420 and preventing it from moving distally during storage.

Referring FIG. 11A, cross-sectional figure A11-A11 and enlargement 11a, the needle shield spring 450 is supported proximally on the spring seat 414 of main housing 410. The needle shield spring 450 urges the needle shield 420 distally by pushing on the needle shield spring face 422.

The outer cover 430 is mounted on the main housing 410 and fixed by any method of bonding, welding, one or more snaps, etc.

Referring to Enlargement A11.1-A11.1 (top), the discard arms 411 of the main housing 410 may be manufactured straight, or with mild arch as shown in FIG. 10A and can become deformed during assembly by engaging of the extension 413 of the discard arms 411 of the main housing 410 with the inner face of the outer cover 430 as shown in FIG. 11A. Alternatively, the discard arms 411 of the main housing 410 can be manufactured already in the shape as shown in Enlargement A11.1-A11.1 of FIG. 11A.

As best seen in sectional view A11.2-A11.2, flange 120 and the syringe barrel 140 of prefilled syringe 100 are supported axially on syringe seat 469 of syringe-support 460 and radially on the syringe-support 460.

Referring now to FIG. 11B, the storage position of the distal plunger 630 and proximal plunger 620 is shown.

In Enlargement 11b.1, though distal plunger 630 is located within arms 625 of proximal plunger 620, the ratchet teeth 632 are situated within "storage positioning range" (between points 623 and 624). Thus ratchet teeth 632 have not engaged their counterpart ratchet teeth 622 of proximal plunger 620. This allows distal plunger to move distally or proximally within the limits of the "storage positioning range" area. Axial movement of the syringe piston 130 may occur due to tolerances or change in axial position of the syringe piston 130 at this stage as described above.

The syringe piston 130 axial position in the prefilled syringe 100 may depend on tolerances in positioning during filling process of the prefilled syringe 100, and on movement of the syringe piston 130 due to changes in ambient pressure and temperature. The syringe piston 130 axial position within the SAN-P device 20 depends also on assembly tolerances of the prefilled syringe 100 within the SAN-P device 20.

Referring to central cross-section B11-B11, the distal tip 633 of the distal plunger 630 is connected by any method of bonding, welding, threading, one or more snaps, etc. to the syringe piston 130.

Anterior plunger pusher 610 and proximal plunger 620 are fixedly connected by snap-fit formed by slot 617 of plunger pusher 610 and ring 621 of proximal plunger 620. This connection can be formed in any way such as gluing, other way of snap-fit, ultrasonic welding or even forming the plunger pusher 610 and proximal plunger 620 as one unitary part.

In Enlargement B11.1-B11.1, the locking face protrusions 611 of anterior plunger pusher 610 are engaged within the grooves of locking faces 481 of rear cap 480 thus preventing the distal movement of the plunger pusher 610.

Protrusions 466 extending from of the lengthened connection arms 461 of the syringe-support 460 prevent the interlock 500 from moving distally.

The distal face of ribs 462 of the connection arms 461 of the syringe-support 460 and the distal ring 505 of the interlock 500 are positioned with an axial gap between them (see "GAP" in enlargement B11.1-B11.1). The outwardly facing locking face 510 of the interlock 500 therefore prevents locking face protrusions 611 of the plunger pusher 610 to bend inwardly, thus preventing the anterior plunger pusher 610 from axially moving distally due to premature pressing of the plunger pusher 610.

In Enlargement B11.2-B11.2, the rim 615 of anterior plunger pusher 610 is limited from moving in the proximal direction by the distal face 482 of rear cap 480. Thus any attempt by the user to pull the plunger pusher 610 proximally and disengage the anterior plunger pusher 610 is prevented.

Referring to FIG. 12, the user has removed the NS remover 240 along with the attached NS 110, by pulling in direction 1000. No additional changes have occurred in the positioning of other components of the device 20.

Figure 13:
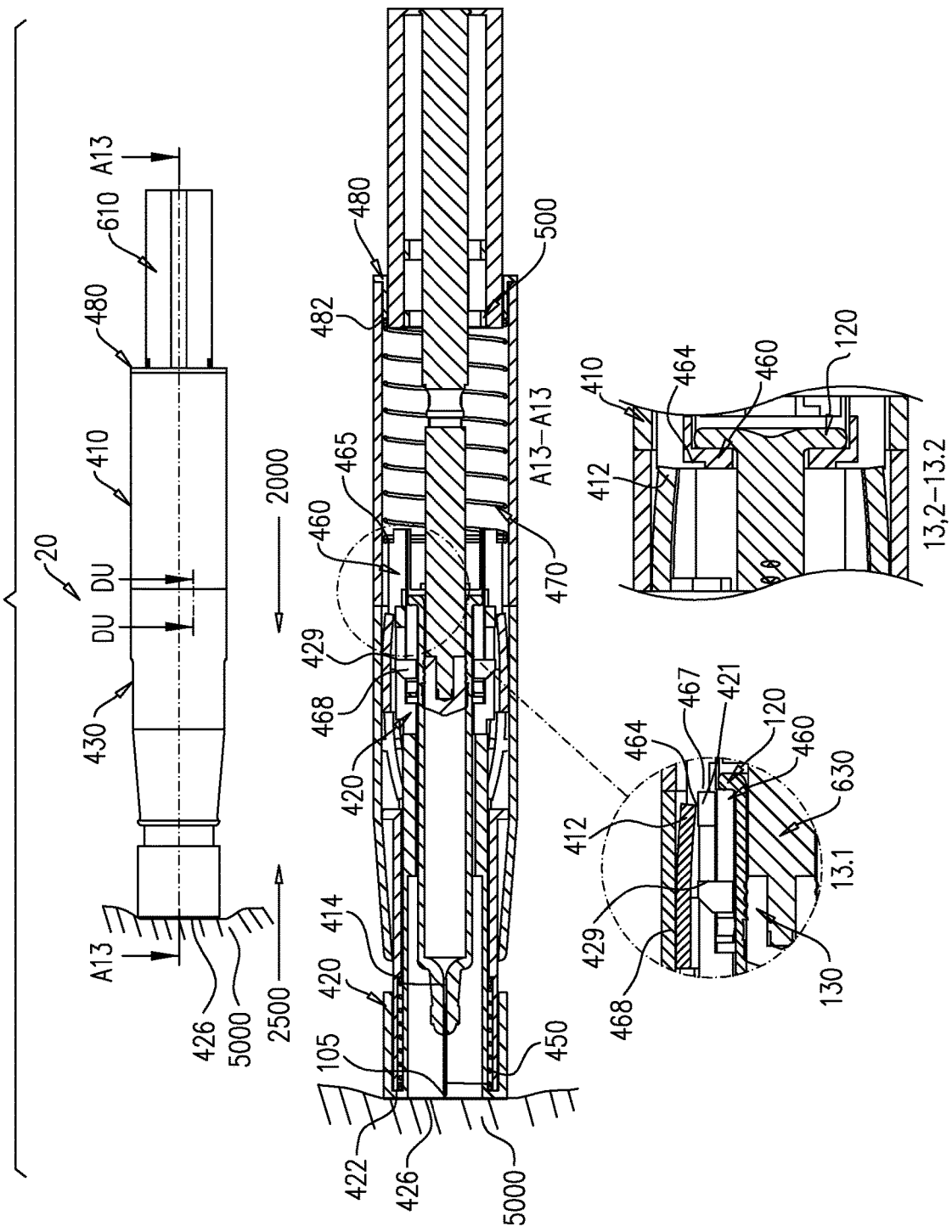

Referring now to FIG. 13, a user now triggers the beginning of the injection process, by pressing the distal end of the SAN-P device 20 upon an exposed injection site 5000, in the distal direction 2000. The needle shield distal end 426 is forced to move proximally in direction 2500 relative to the main housing 410. This figure shows the device immediately prior to movement of the prefilled syringe 100 and the syringe-support 460 distally.

In Enlargement 13.1, bridge 421 of rearward facing arms 429 of the needle shield 420, has moved proximally, thus forcing the locking arms 412 of the main housing 410 to lift radially outwardly.

In cross-sectional Enlargement 13.2-13.2, when locking arms 412 bend outwardly, they release the step 464 of the syringe-support 460, allowing syringe-support 460 to move distally together with prefilled syringe 100 due to force applied by the syringe spring 470 (shown in cross-sectional view A13-A13, where it is shown enlarged compared to upper view from which the cross-section is taken). This results in needle penetration into the injection site, as described in relation to FIG. 14.

Anterior plunger pusher 610 extends from the proximal end. Should a user grasp it forcefully and continuously during use, this will not prevent the desired movement of the syringe-support 460 and needle penetration. This is an advantage of the tri-component plunger (anterior plunger pusher 610, proximal plunger 620 and distal plunger 630).

Figure 14:
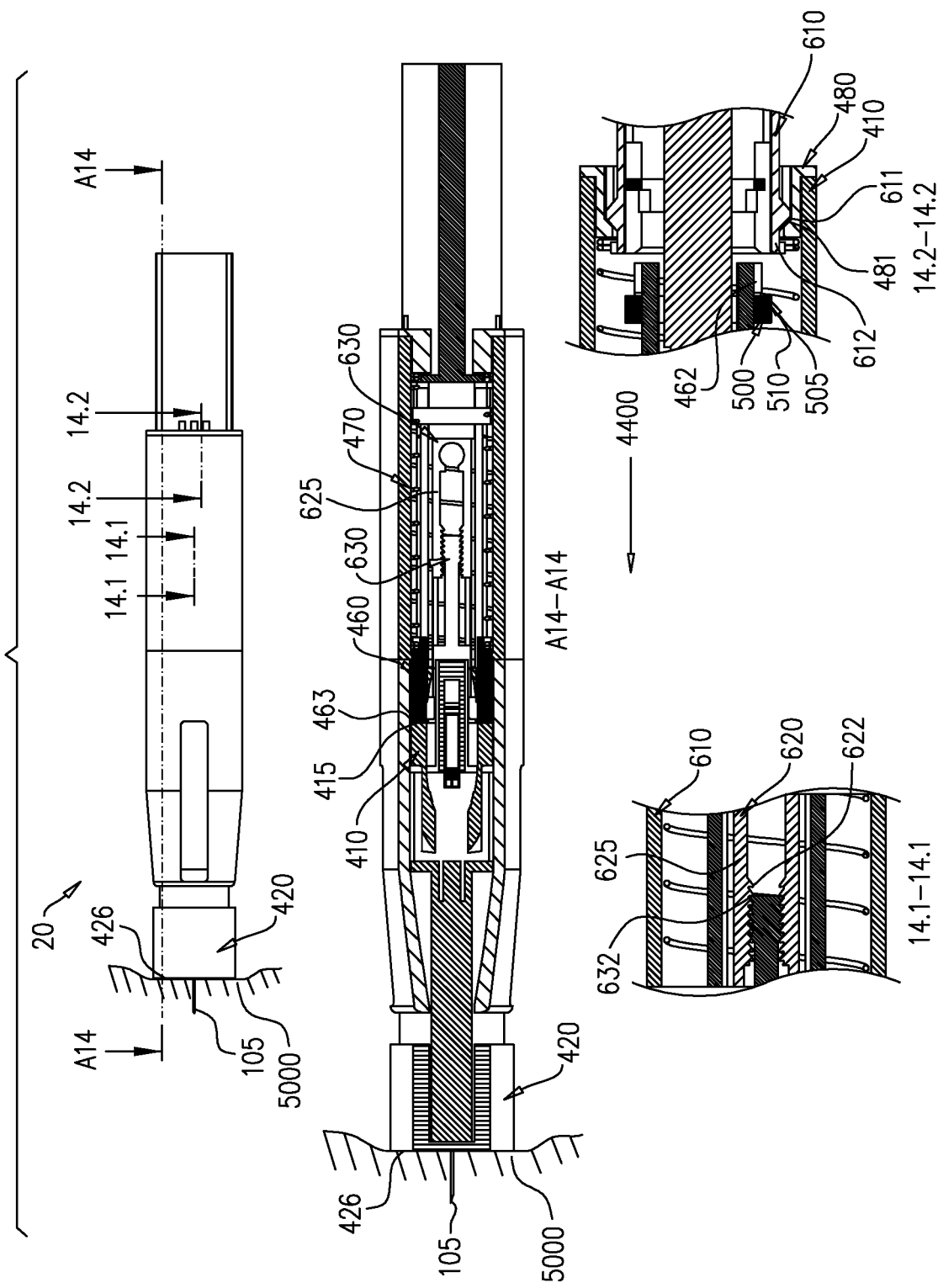

Referring to FIG. 14, needle tip 105 has fully penetrated into the injection site 5000. Note cross-sectional view A14-A14 is shown enlarged compared to upper view from which the cross-section is taken.

The syringe-support 460 has been urged by the syringe spring 470 to fully advance distally until the syringe-support edge 463 of the syringe-support 460 is stopped, by abutting upon the syringe stop 415 of the main housing 410.

In this position, the needle tip 105 of the prefilled syringe 100 has penetrated to the appropriate depth into the injection site 5000.

The distal plunger 630, which is connected to the syringe piston 130, has moved along with the prefilled syringe 100.

Referring to Enlarged Partial Section 14.1-14.1, this distal movement results in engagement of ratchet teeth 632 of the distal plunger 630, with the counterpart ratchet teeth 622 of the proximal plunger 620. This engagement is achieved by outwardly deflecting the flexible arms 625 of proximal plunger 620 on which the proximal plunger ratchet teeth 622 are formed. The axial position of the engagement between the distal plunger ratchet teeth 632 and the proximal plunger ratchet teeth 622 depends, inter-alia, on the initial axial position of the syringe piston 130.

In Enlarged Partial Section 14.2-14.2, the interlock 500 has moved distally and no longer prevents a user from pressing the plunger and discharging the medication:

The interlock 500 has been pushed distally in direction 4400 by the distal face of ribs 462 of the connection arms 461 of the syringe-support 460.

Distal movement of the interlock 500 has removed the interlock's locking face 510 from its previous position and is no longer opposing terminal fingers 612 of the anterior plunger pusher 610 to bend inwardly and disengage the internal grooved locking faces 481 of the rear cap 480. Anterior plunger pusher 610 may then be pressed by a user.

Figure 15:
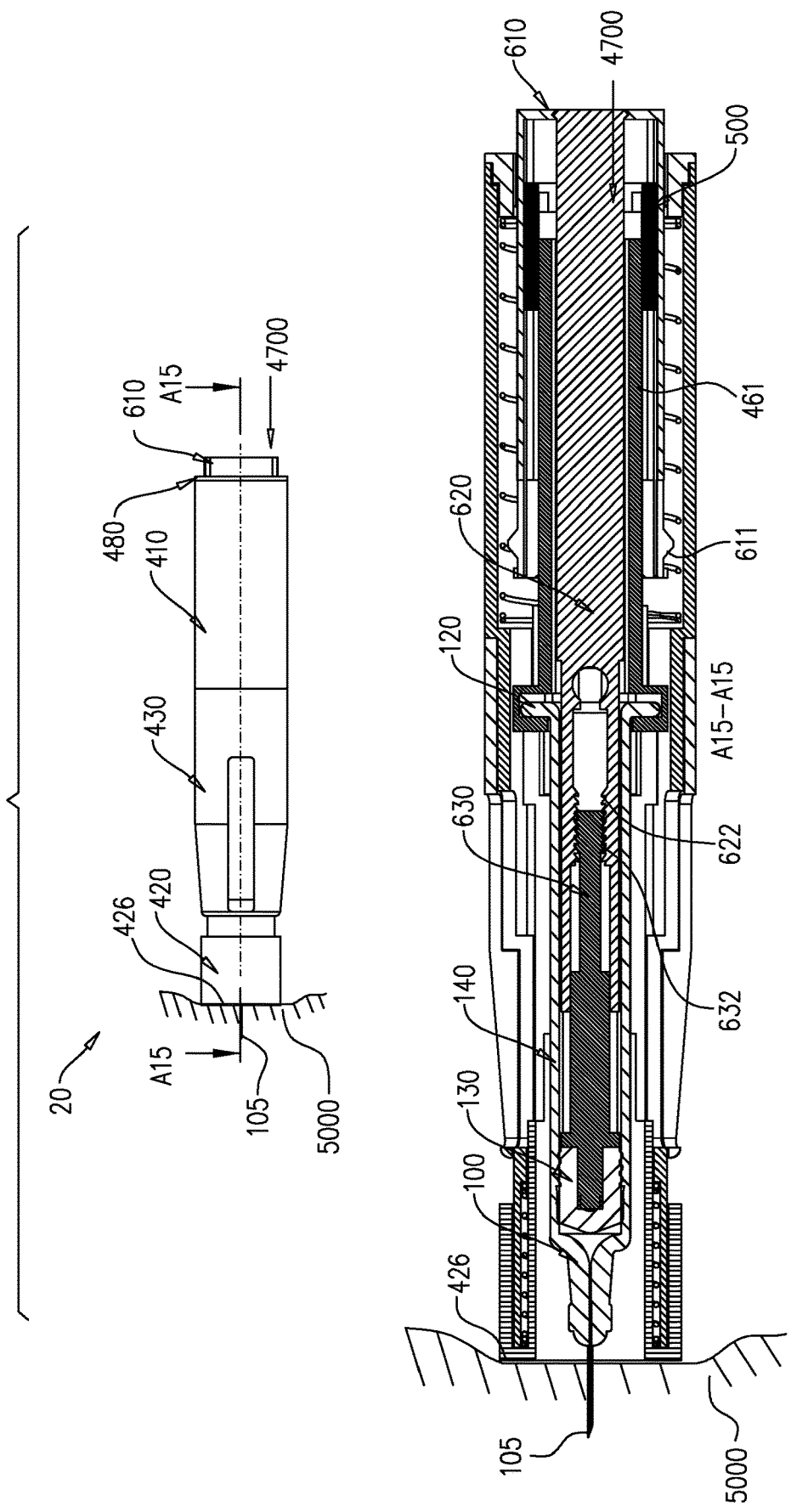

Referring to FIG. 15, medication has been injected by a user, who has pressed the anterior plunger pusher 610, at the user's preferred injection rate. Note cross-sectional view A15-A15 is shown enlarged compared to upper view from which the cross-section is taken.

When the anterior plunger pusher 610 is pressed in the distal direction 4700, it urges all three of the tri-component plunger components to move distally (proximal plunger 620, distal plunger 630, and anterior plunger pusher 610). Distal movement only occurs, due to the engagement of the ratchet teeth 622 of proximal plunger 620 and ratchet teeth 632 of distal plunger 630. The syringe piston 130 of the prefilled syringe 100 is thus moved distally to inject the fluid via the needle tip 105.

Injection ends when the syringe piston 130 has reached the end of the syringe barrel 140 and stops, indicating that the injection is complete.

Referring to FIG. 16, the device 20 is shown in the discard position. In this state, inadvertent needle pricks are prevented during handling for discard, since the needle shield is locked in its fully extended state, hiding the needle tip. Note cross-sectional view A16-A16 is shown enlarged compared to upper view from which the cross-section is taken.

After removing the SAN-P device 20 from the injection site 5000, the needle shield 420 is urged by needle shield spring 450 to move distally relative to the main housing 410, to its maximally extended state.

Referring to Enlargement 16.1 (center), the needle shield 420 is then locked in this maximally extended position, as follows: Rib 428 of the needle shield 420, has forced the needle shield locking arms 411 to bend outwardly thus allowing the rib 428 to pass the locking arms 411 of the main housing 410, and reach the stop position shown in enlargement 16.1. In this stop position, rib 428 is blocked by locking arm 411 from moving proximally.

Referring to Enlarged Partial Section B16-B16, distal axial movement of needle shield 420 is stopped by the distal facing edge 423 of the needle shield 420 which reaches the needle shield stop 416 of the main housing 410.

In this state, reuse and inadvertent needle-sticks cannot occur from a used needle.

Referring now to FIGS. 17-24, a third embodiment of the device is described, having an NS remover of another design. The terminal external end of the NS remover is attached to the main housing, and if the device is dropped, transfers forces to a stopper on the main housing, to prevent breakage of the syringe, in another manner than described in other embodiments. NS remover is comprised of an external part which attaches to the main housing, and an internal part which grasps the NS.

Referring to FIG. 17, an exploded view is shown of Embodiment Three of the device 30, including (left to right): NS remover external part 340, NS remover internal part 343, needle shield 320, needle shield spring 350, main housing 310, syringe spring 370, prefilled syringe 100, syringe-support 360, rear cap 380, and plunger rod 390.

Sticker 330 is stuck upon on the main housing 310. The sticker 330 can be made of transparent material, opaque, or partially opaque, and may have a viewing window for viewing the appearance of the medication. The SAN-P assembly 30 can be also produced without sticker 330 or with another external component preferably made of plastic, alternatively to sticker 330.

Figure 18A:
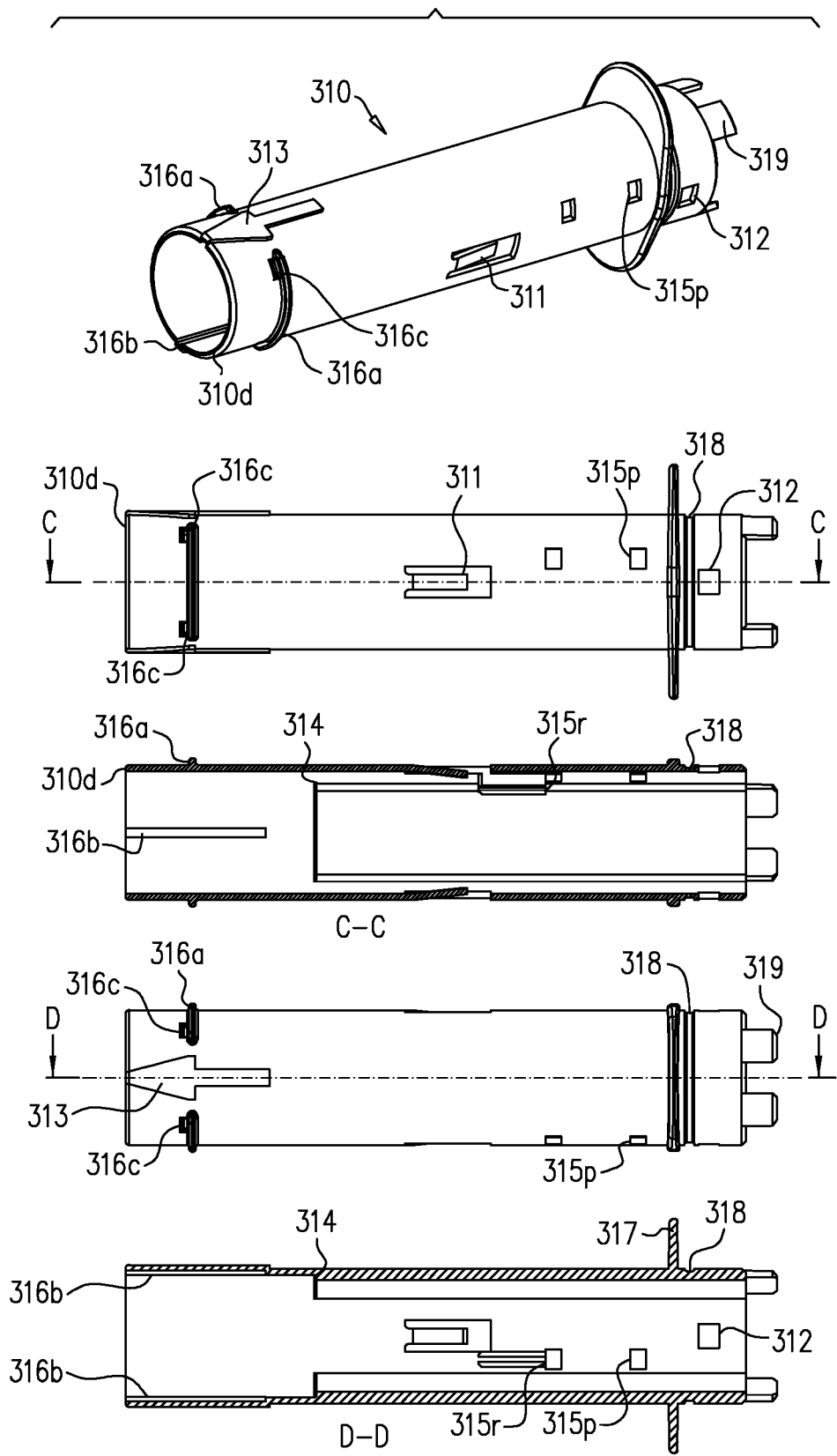

Referring now to FIGS. 18A-18F, enlargements of the central components of the invention are presented, as follows:

FIG. 18A illustrates the main housing 310. Main housing 310 is formed with cutouts 312 which engage protrusions 321$d$ of the needle shield 320 to lock the needle shield 320 in its extended position at discard orientation.

Stop window 315$p$ (best shown in perspective view at top) engages the syringe-support 360 and prevents its movement during storage.

Stopper 316$a$ are circumferential ribs which absorbs impact forces transferred to it by the external part 340 of the NS remover, should the device 30 be dropped accidentally.

Snaps 311 are used to hold the needle shield 320 during the assembly process of the SAN-P 30, but have no role during the operation of the device.

Figure 18B:
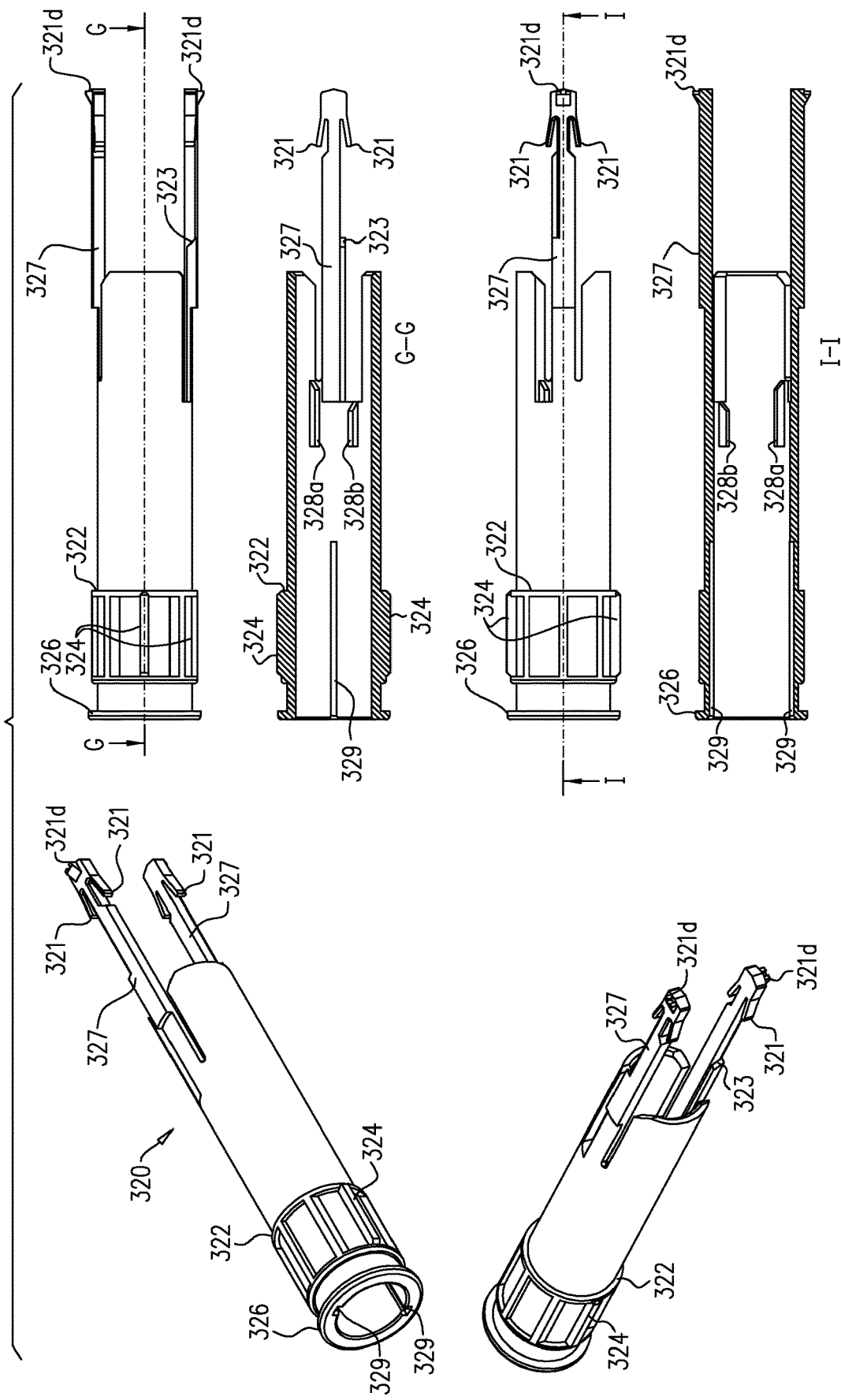

In perspective view at top and cross-section views C-C and D-D, several internal slots 316$b$ receive guiding ribs 324 of the needle shield 320 (shown in FIG. 18B).

In perspective view at top, side view (second from bottom), and top view (second from top), several external slots 316$c$ are formed forwardly to ribs 316$a$.

As best seen in cross-section views C-C and D-D, stopping ribs 315$r$ will interact with the syringe-support 360 and ends its distal movement thus stopping needle penetration.

FIG. 18B illustrates needle shield 320 having arms 327 terminating in fingers 321 and its protrusions 321$d$.

Ring 326 is the terminal distal end of the device after removal of the NS remover, and will contact the injection site.

Activation slopes 323 will interact with counterpart activation slopes 361 of the syringe-support 360, to release and allow movement of syringe-support 360.

A pair of external longitudinal ribs 324 are formed on the needle shield 320, interacting with slots 316$b$ of the main housing 310 to guide the needle shield 320 axial movement.

As best seen in cross-section views G-G and I-I, two pairs of longitudinally ribs 328$a$ and 328$b$ extend along the axis of the needle shield 320 guide and maintain the barrel 140 of the prefilled syringe 100 centered within the lumen of the device 30.

FIG. 18C illustrates external part 340 of the NS remover, and internal part 343 of the NS remover. Snap teeth 341 are shown, which grips the NS to allow removal of the NS along with NS remover parts 340, 343.

Longitudinal guiding ribs 347 of the internal part 343 of the NS remover are received by slots 329 of the needle shield 320.

As can be seen in section View M-M damping and secure clamping of external and internal NS remover parts 340 and 343 respectively, to one another, is ensured by the presence of flexible teeth 348$e$ on external part 340 and ratchet teeth 348$i$ on internal part 343. Ratchet teeth 348$i$ are best shown in view N-N. Flexible teeth 348$e$ engaging with ratchet teeth 348$i$ may be seen on section-view 18$c$.2 and section-view N-N on the middle bottom.

Variations may occur during assembly of the prefilled syringe 100 components. This may result in large axial tolerance in the axial position of the NS 110, relative to the prefilled syringe barrel 140 and flange 120. In addition, various tolerances occur in the SAN-P 30 parts and during assembly of the SAN-P. Therefore, the NS distal rigid rim 112 may be located at various distances relative to the NS remover stopper 316$a$ of the main housing 310.

This is overcome in the 3rd and the 4th embodiments described herein (in FIGS. 17-32) by using a two-part NS remover, having an internal part 343 and an external part 340 which are engaged through ratchet teeth 348$i$ of the NS remover internal part 343 and flexible teeth 348$e$ of the NS remover external part 340. The ratchet mechanism enables engagement of the two parts during assembly at the required axial position, while having them lock for removal of the NS 110. The ratchet mechanism can be alternatively produced with the ratchet teeth on the external part 340 and flexible teeth on the internal part 343. Alternatively, the ratchet mechanism may be replaced by any other type of connection, e.g., by heat welding, gluing, and other types of connections preferably done after assembly.

Figure 18D:
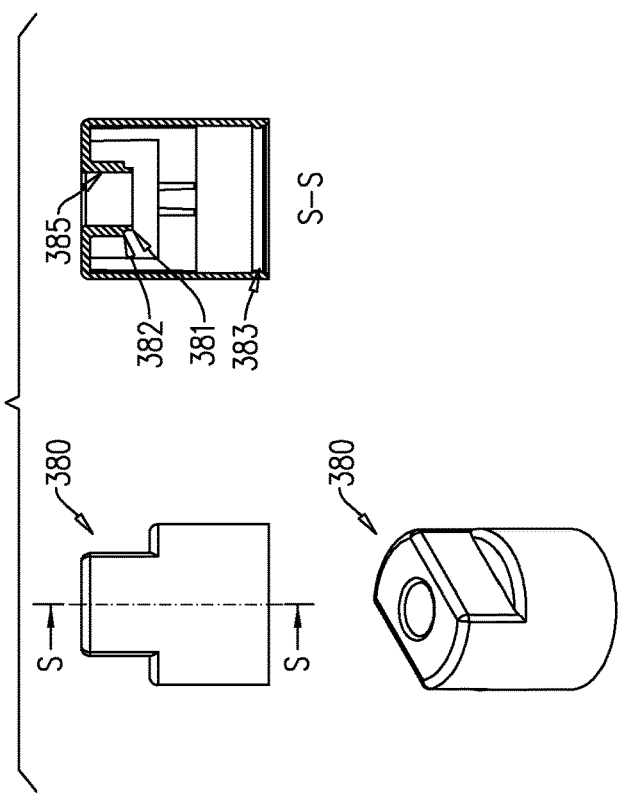

FIG. 18D illustrates the syringe-support 360. In this embodiment, syringe-support 360 includes a syringe flange seat 368 slot and syringe supporting rim 367, which are open at one side to accept an inserted prefilled syringe 100 and its flange 120.

In isometric view at left, syringe spring forward seat 369 is apparent, which holds syringe spring 370. Compressed syringe spring 370 urges the syringe-support 360 distally.

Syringe-support 360 includes locking arms 365. During storage, locking arms 365 enter and engage stop window 315$p$ of the main housing 310 to prevent movement of the syringe-support 360.

Activation slopes 361 are formed at the terminal end of locking arms 365. When an injection is initiated by a user, activation slopes 361 slide against activation slopes 323 of the needle shield 320, to bend locking arms 365 inward, and release them from their locking position by removing the locking arms from stop window 315$p$ of main housing 310.

Shoulders 364 engage with fingers 321 of the needle shield 320 during storage, to prevent distal movement of needle shield 320.

Figure 18E:
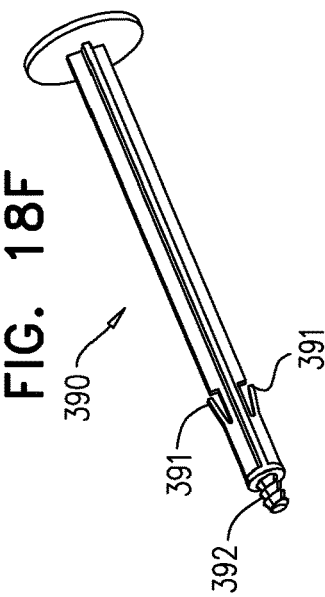

In FIG. 18E, rear cap 380 is shown, having inner guiding sleeve 385 which supports plunger rod 390 and guides plunger rod 390 axially when plunger rod is pressed by a user.

Syringe spring seat 382 support the proximal end of the syringe spring 370. Note forward facing edge 381, which prevents a user from pulling (hyper-extending) the plunger rod 390 instead of pressing it, by abutting against a front locking segments 391 of the plunger rod 390.

Figure 19A:
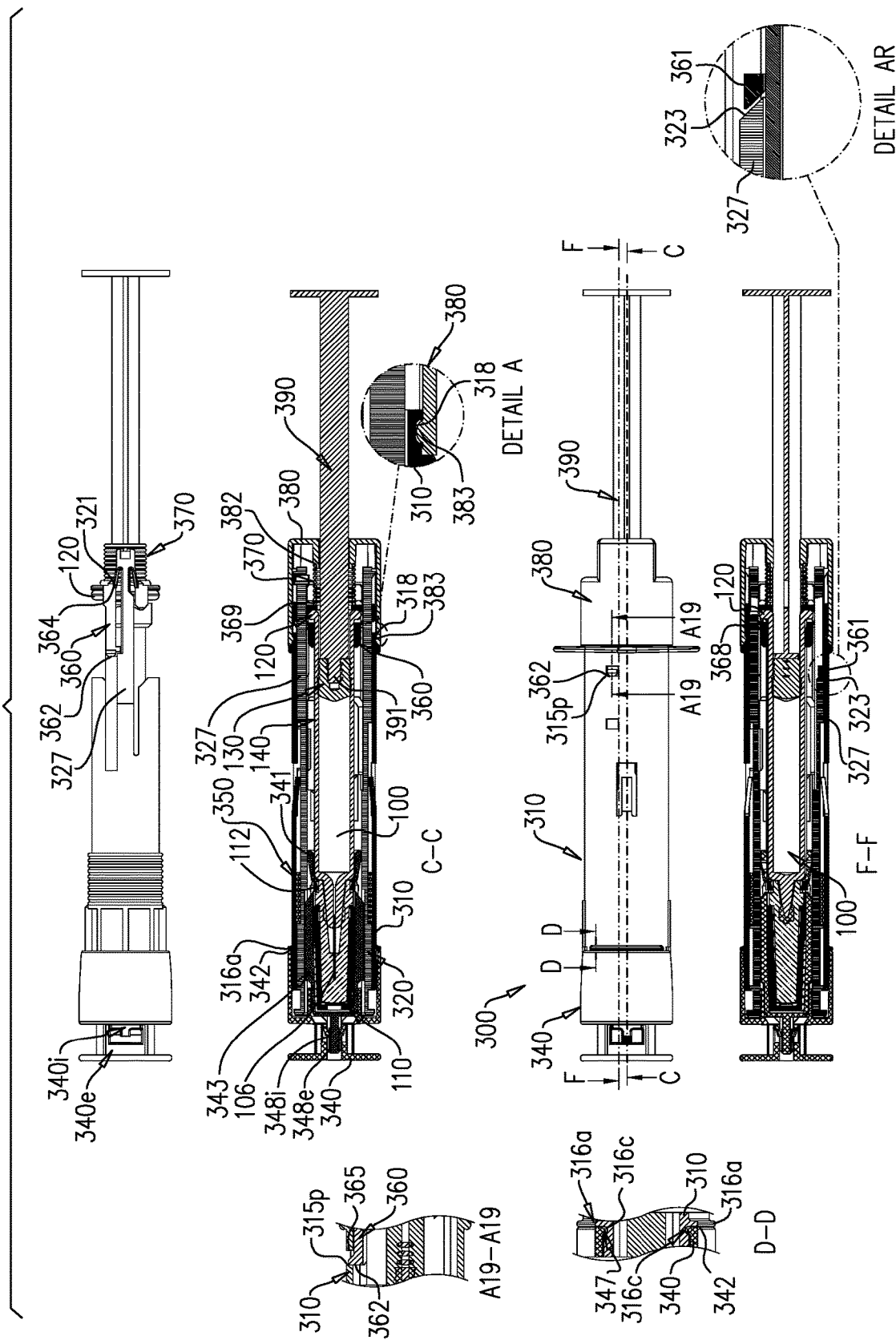

Connection ring 383 engages rear cap 380 to main housing 310 via slot 318 (shown in FIG. 18A, and Detail A of FIG. 19A).

Figure 18F:
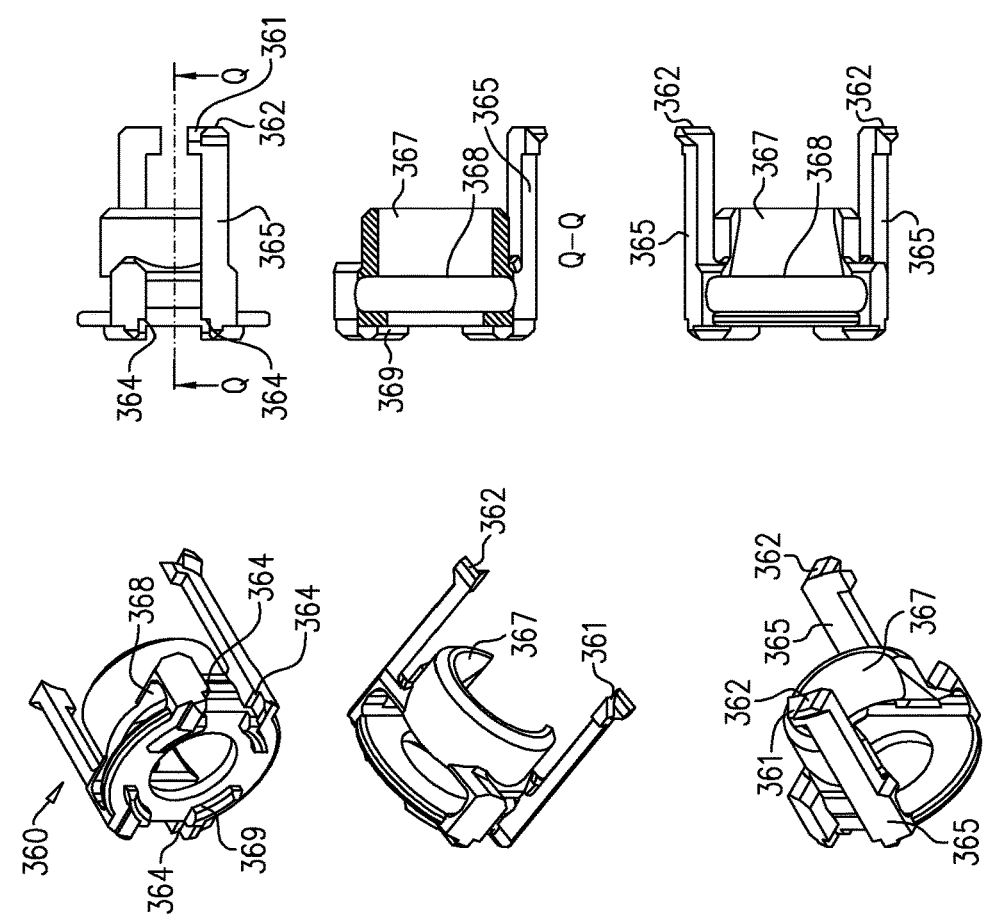

In FIG. 18F, plunger rod 390 is illustrated with flexible front locking segments 391, and forward facing tip 392 that engages the piston 120 (not shown).

Figure 19B:
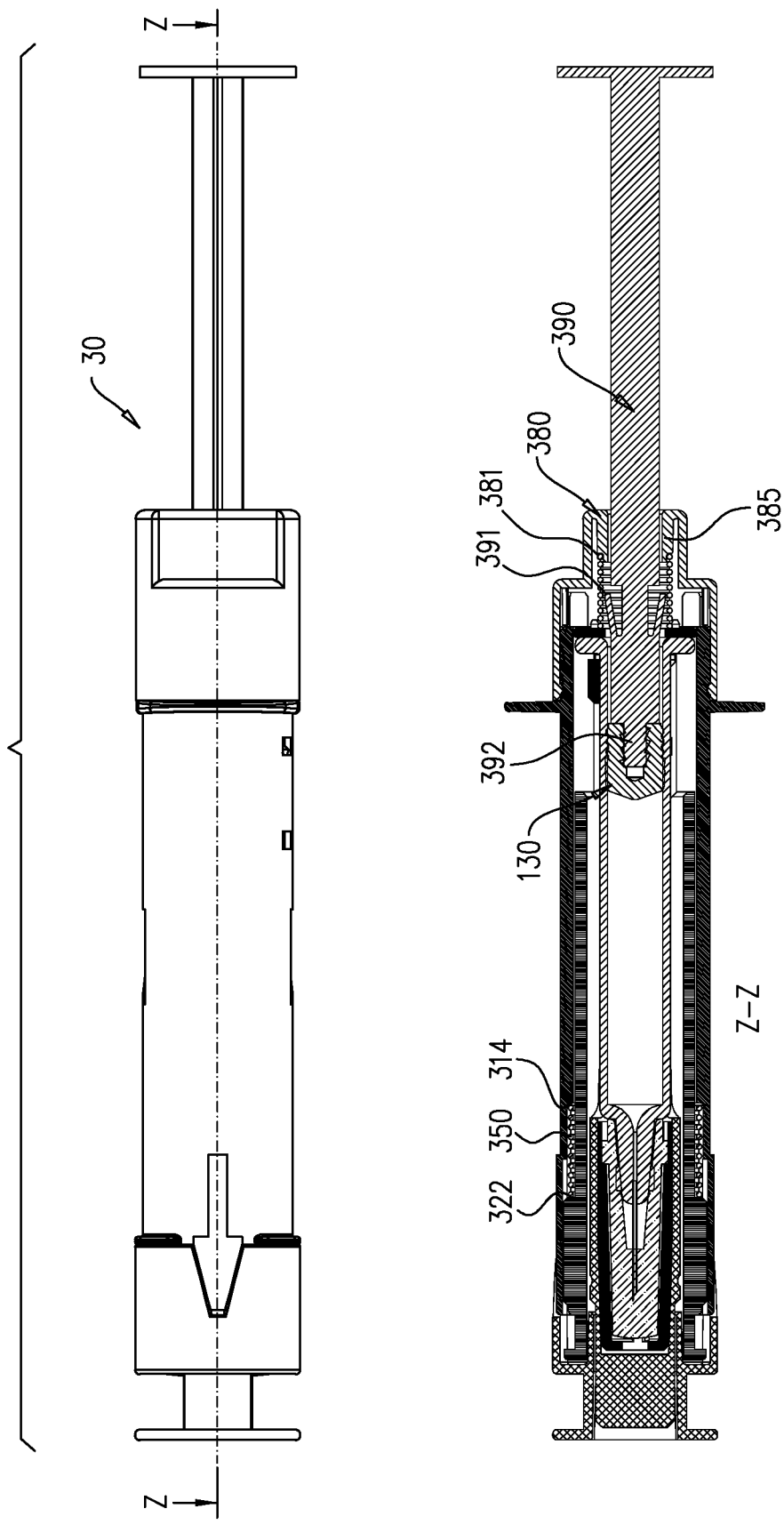

Referring to FIGS. 19A and 19B, the device 30 is shown in its storage stage. To allow viewing of internal elements, the following components have been removed from the top view of FIG. 19A: rear cap 380, sticker 330, and main housing 310. For simplicity and clarification, the sticker 330 has been removed from all other views, cross-sections and enlargements of FIGS. 19A and 19B.

The prefilled syringe 100 is assembled into the syringe-support 360 and is held axially in both distal and proximal directions by engagement of the syringe flange 120 within the syringe flange seat 368 slot of the syringe-support 360 as best seen in sectional view F-F.

Referring to Sectional View C-C, the syringe spring 370 is supported proximally on the rearward syringe spring seat 382 of rear cap 380. The compressed syringe spring 370 urges the syringe-support 360 distally by pushing on the syringe spring forward seat 369 of the syringe-support 360.

Referring to Enlargement A19-A19 (left), the forward stop face 362 of the syringe-support 360 engages the stop window 315p of main housing 310 preventing syringe-support 360 from moving distally.

Referring still to Sectional View C-C, when the device is accidentally dropped, and an impact force is applied to the distal end of the device, namely to NS remover external part 340, the rearward facing edge 342 of external part 340 will contact and transfer the impact force to the stopper 316a of the main housing 310 thus limiting the force transmitted to the prefilled syringe 100. This feature reduces the chance of breakage of the syringe barrel 140 and/or it's flange 120, which are often produced from glass.

Referring to the left-most view, the fingers 321 of needle shield arm 327 hold the needle shield 320 on the shoulders 364 of the syringe-support 360, thus preventing the needle shield 320 from moving distally.

Referring to Enlargement "Detail A", the rear cap 380 is engaged to the main housing 310 via connection ring 383 of the rear cap 380 which has entered slot 318 of the main housing 310. This engagement can be of any form, such as a screw, a snap-fit, gluing, welding or any other suitable form. Alternatively, the main housing 310 and rear cap 380 can be a single unitary part or can be separated into two or more parts in other locations.

Referring to Sectional Enlargement D-D (lower left), the external part 340 of the NS remover snaps onto the main housing 310, as follows: NS remover external part 340 has four internal protrusions 347 which engage into four circumferentially located slots 316c, which are formed adjacent to and distally of the stopper 316a of the main housing 310. Protrusions 347 retain NS remover external part 340 and prevent its movement distally during storage. Such Protrusions 347 and slots 316c can be of any number, formed as flexible snap-fits, etc. Additionally, they can be formed such that the protrusions are formed in the main housing 310 and the slots are formed in the NS remover external part 340.

Alternatively, the NS remover external part 340 may be retained to the main housing 310 using a sticker that has to be removed or torn before removing the NS. The sticker can be evidence that the syringe has not been tampered with. Furthermore, the NS remover external part 340 can be welded/glued to the main housing 310 in a relatively weak welding, breakable by the user.

Referring to Cross-Section View F-F and "Detail B" at bottom, activation slope 361 is apparent upon the terminal end of locking arms 365 of the syringe-support 360. This slope 361 lies opposite counterpart and proximally to activation slope 323 of the needle shield 320.

Referring to FIG. 19B. To allow viewing of internal elements, the sticker 330 has been removed from FIG. 19B at the top. Referring to cross-section Z-Z, the plunger rod 390 is engaged with the piston 130 at its forward facing tip 392. This engagement can be of any form, such as a screw as shown, as a snap-fit, or any other suitable form.

Plunger rod locking segments 391 prevent the piston 130 from being pulled out from the prefilled syringe 100, as such action will thrust the front locking segment tab 391 toward forward facing edge 381 of rear cap 380, stopping pulling (hyper-extension) of the plunger rod 390. Plunger rod 390 is guided axially in inner guiding sleeve 385 of rear cap 380.

Needle shield spring 350 is supported proximally on the shield spring rearward seat 314 of main housing 310. The needle shield spring 350 urges the needle shield 320 distally by pushing on the shield spring forward seat 322 of the needle shield 320.

The NS remover internal part 343 is engaged to and grips the NS 110 which conceals the needle 106 and the needle tip 105 of the prefilled syringe 100.

Referring to FIG. 20, the two-part NS remover (340, 343) has been removed by the user, along with the NS 110. No changes have occurred in the position of any other part the SAN-P device 30. For simplicity and clarification, the sticker 330 has been removed from all views, cross-sections and enlargements of FIG. 20.

The NS 110 has been removed by pulling the NS remover external part 340 distally in direction 1000. NS remover internal part 343 is pulled away together with NS remover external part 340 by engagement of flexible teeth 348e of the NS remover external part 340 with ratchet teeth 348i of the NS remover internal part 343. NS remover snap teeth 341 of NS remover internal part 343 grab the NS distal rigid rim 112 of NS 110.

In order to protect the needle 106 from damage, during removing the NS remover assembly 340 and the NS 110, the NS remover internal part 343 is guided axially on the needle shield 320 thus preventing any bending load on the needle 106. The needle 106 remains hidden throughout this stage. It can be understood that there can be one or more NS remover snap teeth 341. NS remover snap teeth 341 of NS remover internal part 343 keep the NS 110 within the NS remover assembly, thus preventing a potential choking hazard.

Referring to FIG. 21, (third view from top), a user initiates the injection process by pressing the SAN-P device 30 against an injection site 5000 in the distal direction 1050. The terminal ring 326 of the needle shield 320 presses against the injection site, and is forced to move proximally in direction 1100. To allow viewing of internal elements, the following components have been removed from the top view of FIG. 21: rear cap 380, sticker 330, and main housing 310. For simplicity and clarification, the sticker 330 has been removed from all other views, cross-sections and enlargements of FIG. 21.

In FIG. 21 Section J-J (second view from top), ring 326 of the needle shield 320 stops on the distal edge 310d of the main housing 310.

In sectional view L-L and "Detail C" (bottom), and in enlarged section AB-AB on the left, during proximal movement of needle shield 320, activation slope 323 of needle shield 320 slides against activation slope 361 of the syringe-support 360 and bends locking arms 365 inwardly. Note position of slope 361 relative to slope 323, as compared to their previous relative positions in FIG. 19A (bottom image and "Detail B").

Figure 22:
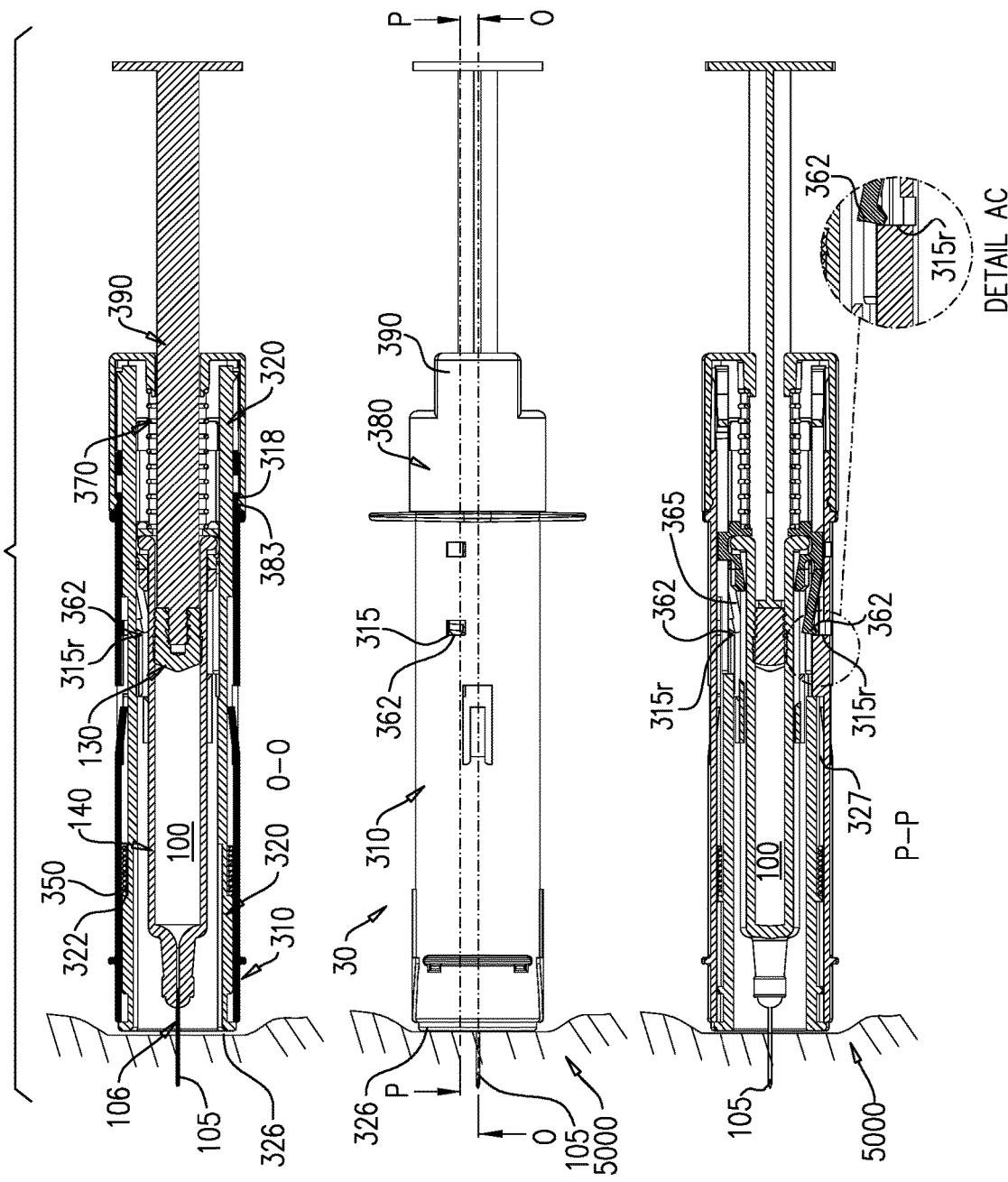

As shown in Enlargement AB-AB (left), this inward bending of locking arms 365 of the syringe-support 360 disengages the forward stop face 362 from within the stop window 315p of the main housing 310 and allows the syringe-support 360 to move distally with the prefilled syringe 100, urged by syringe spring 370 as shown in FIG. 22 (FIG. 21 shows the syringe-support 360 immediately prior to distal movement).

Referring to FIG. 22, complete needle penetration has occurred. For simplicity and clarification, the sticker 330 has been removed from all other views, cross-sections and enlargements of FIG. 22. In bottom view and Enlargement "Detail AC", urged by extension of the compressed syringe spring 370, the syringe-support 360 has moved distally until the forward stop face 362 of the syringe-support 360 stops on the stopping ribs 315r of the main housing 310.

In this position, the needle tip 105 of the prefilled syringe 100 has penetrated to the appropriate depth into the injection site 5000, as shown in bottom view and the plunger rod 390 has moved distally together with the piston 130 of the prefilled syringe 100.

Figure 23:
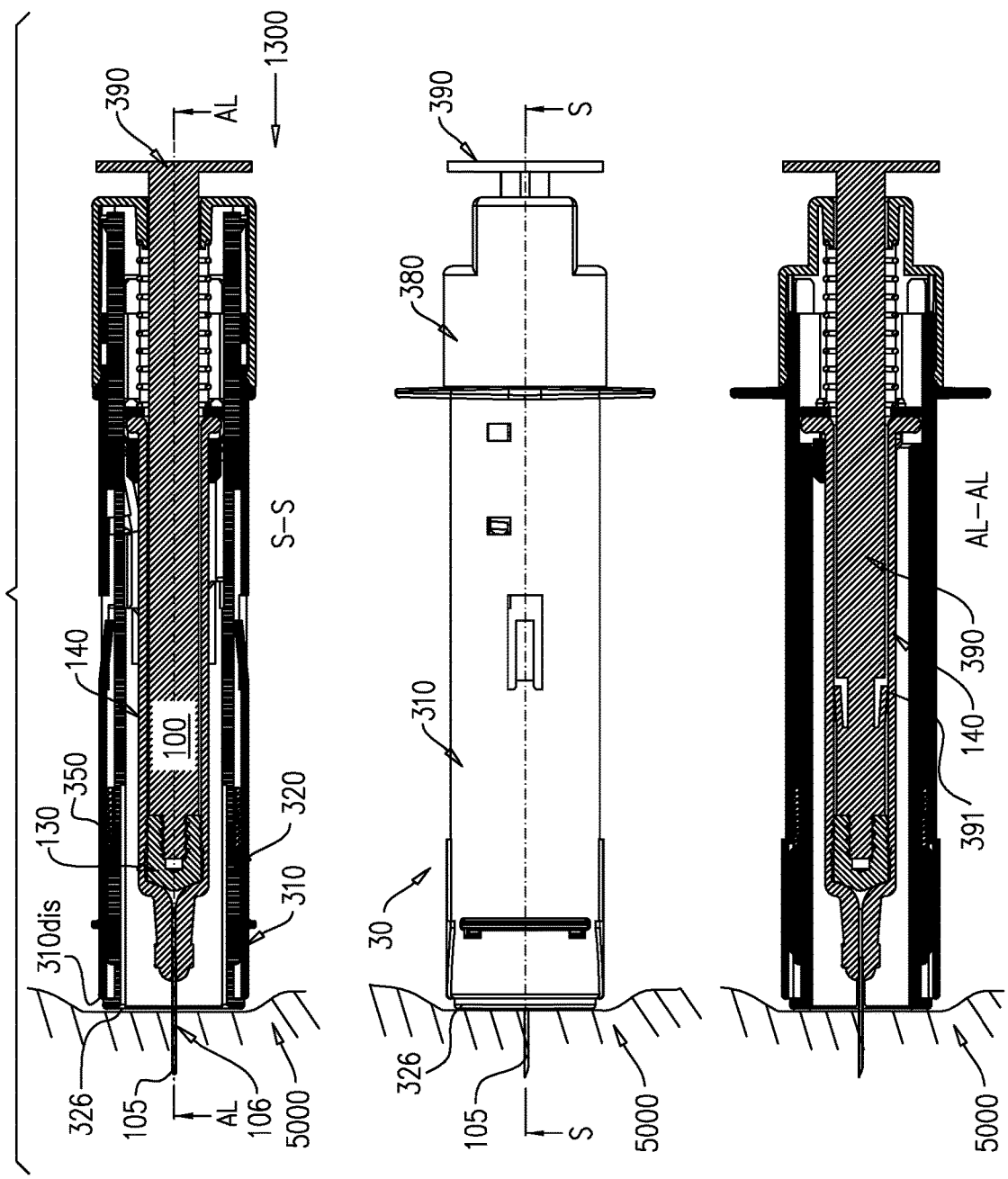

Referring to FIG. 23, a user may now press the plunger rod 390 in direction 1300, thereby advancing piston 130 to inject the fluid via the needle tip 105. For simplicity and clarification, the sticker 330 has been removed from all other views, cross-sections and enlargements of FIG. 23.

The front locking segment 391 of the plunger rod 390 flexibly bends inwardly while entering into the syringe barrel 140.

At the end of injection, the piston 130 reaches the front end of the syringe barrel 140 and stops, indicating to the user that the injection is complete.

Figure 24:
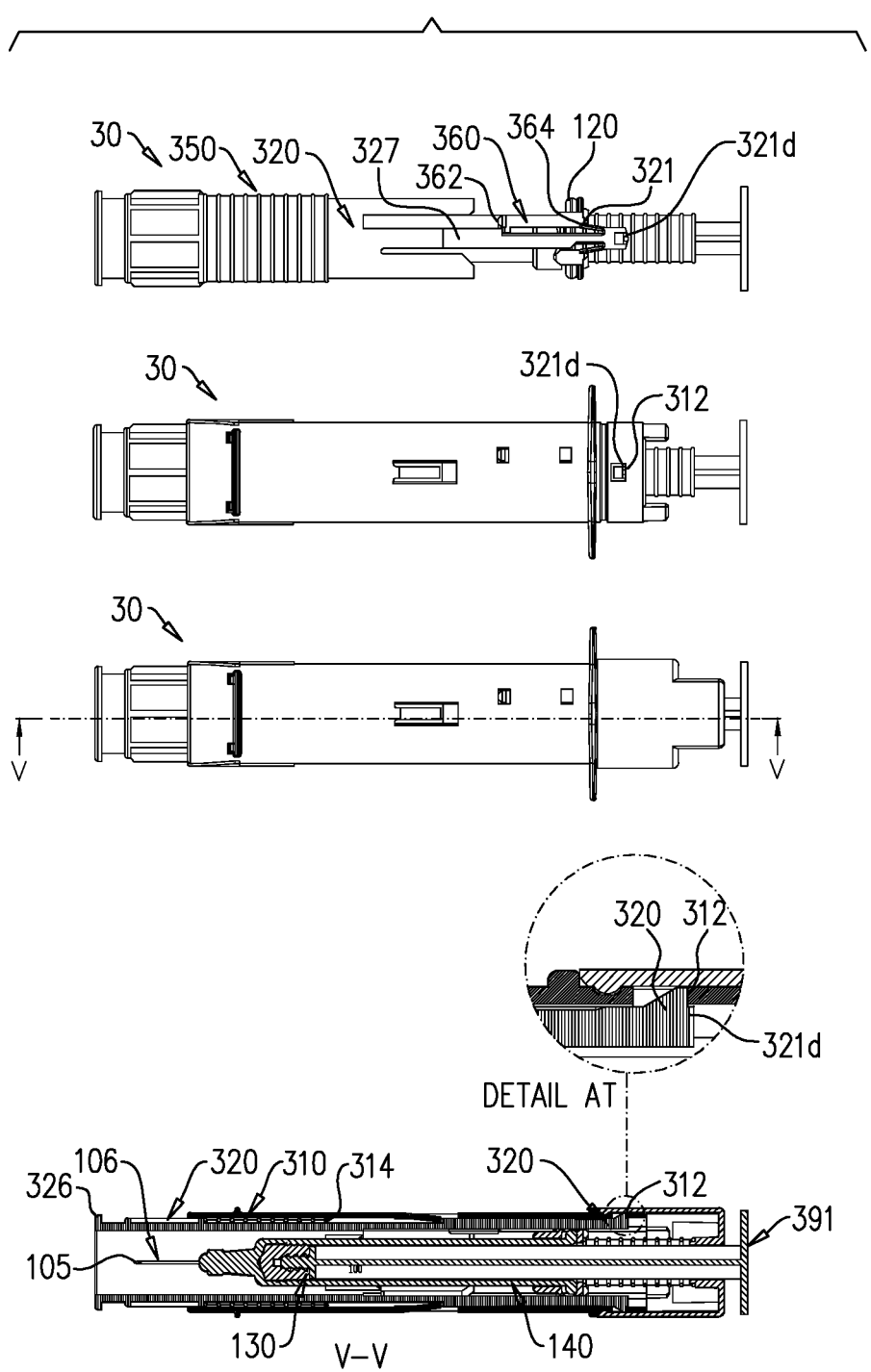

Referring to FIG. 24, the device is shown in the "discard" stage, namely automatic needle shielding occurs after a user removes the SAN-P device 30 from the injection site 5000. In the top view, rear cap 380, main housing 310 and sticker 330 have been removed to view internal components. For simplicity and clarification, the sticker 330 has been removed from all other views, cross-sections and enlargements of FIG. 24.

When the user removes the SAN-P assembly 30 proximally away from the injection site 5000, the needle shield 320 is urged by the needle shield spring 350, to move distally relative to the main housing 310.

As shown in upper-most illustration, distal movement of the needle shield 320 is stopped when the fingers 321 of the needle shield 320 stop upon shoulders 364 of the syringe-support 360.

As shown in lowest illustration and "Detail D", the needle shield 320 is in its most distal position, hiding the needle tip 105.

The needle shield 320 is locked in this position towards proximal movement by the following mechanism: the proximal face of outward- and rearward-facing protrusions 321d (shown in FIG. 18B) of the needle shield 320 engage with cutout 312 of the main housing 310 (shown in second view from top), thus preventing the needle shield 320 from moving proximally, protecting the needle from being exposed.

In this state, reuse and inadvertent needle-sticks cannot occur from a used needle.

FIG. 25-32 illustrate a fourth Embodiment of the device, comprising an alternative interlock design, which prevents a user from pressing the plunger before complete needle penetration has occurred. This prevents premature discharge of the contents. Further, in this embodiment, an additional safety measure is included, so that once the device is removed from the injection site, a plunger one-way ratchet system prevents additional movement of the plunger. This eliminates discharge of leftover medication droplets which could contaminate the environment with hazardous medication.

Figure 25:
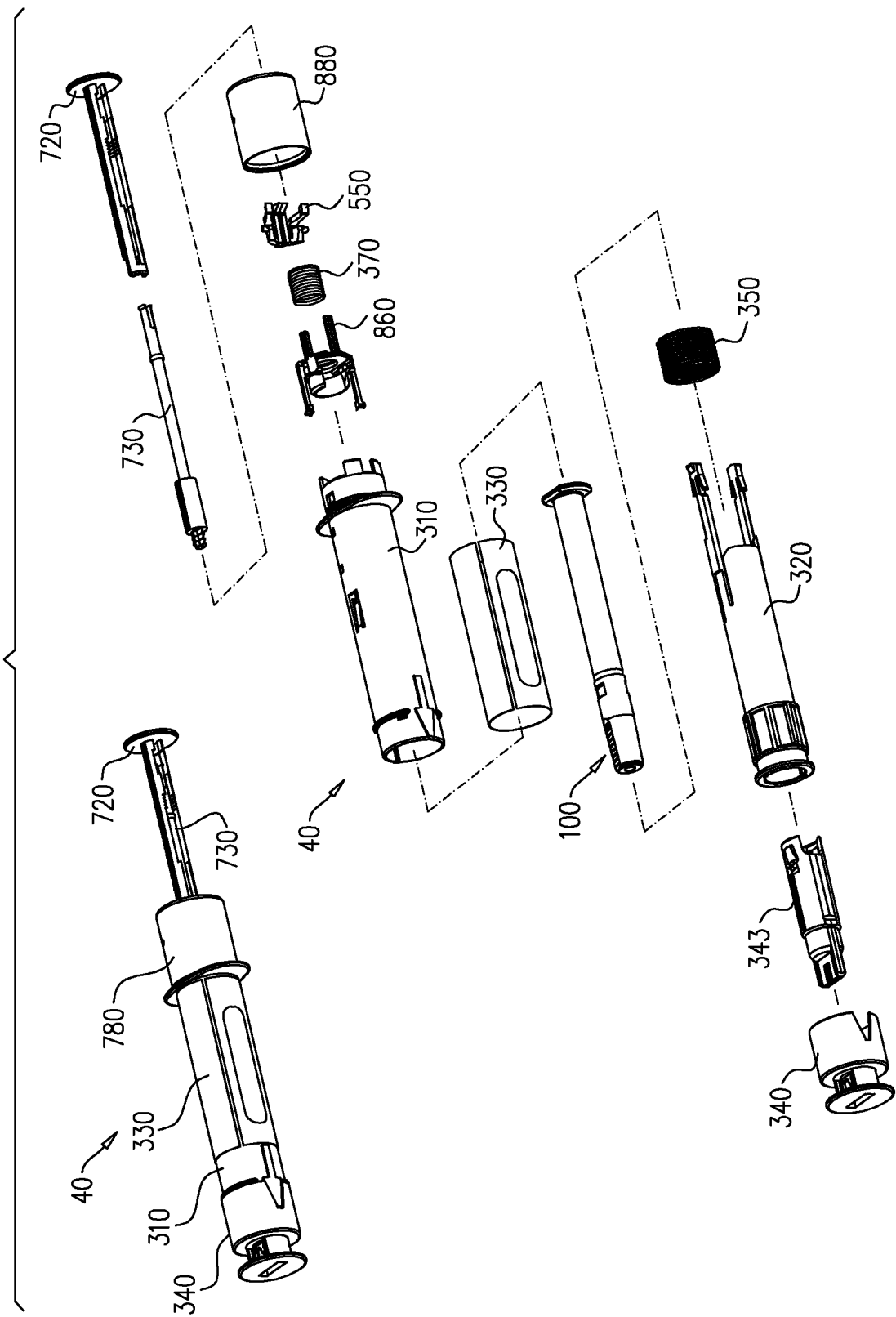

Referring now to FIG. 25, an exploded view of the central components of Embodiment 4 are shown, including (left to right): NS Remover External Part 340, NS Remover Internal Part 343, Needle Shield 320, Needle Shield Spring 350, Prefilled Syringe 100, Sticker 330, Main Housing 310, Syringe-support 860, Syringe Spring 370, Interlock 550, Rear Cap 880, and two-component plunger comprising distal plunger 730, and proximal plunger 720 having plunger flange for pressing the plunger.

Figure 26A:
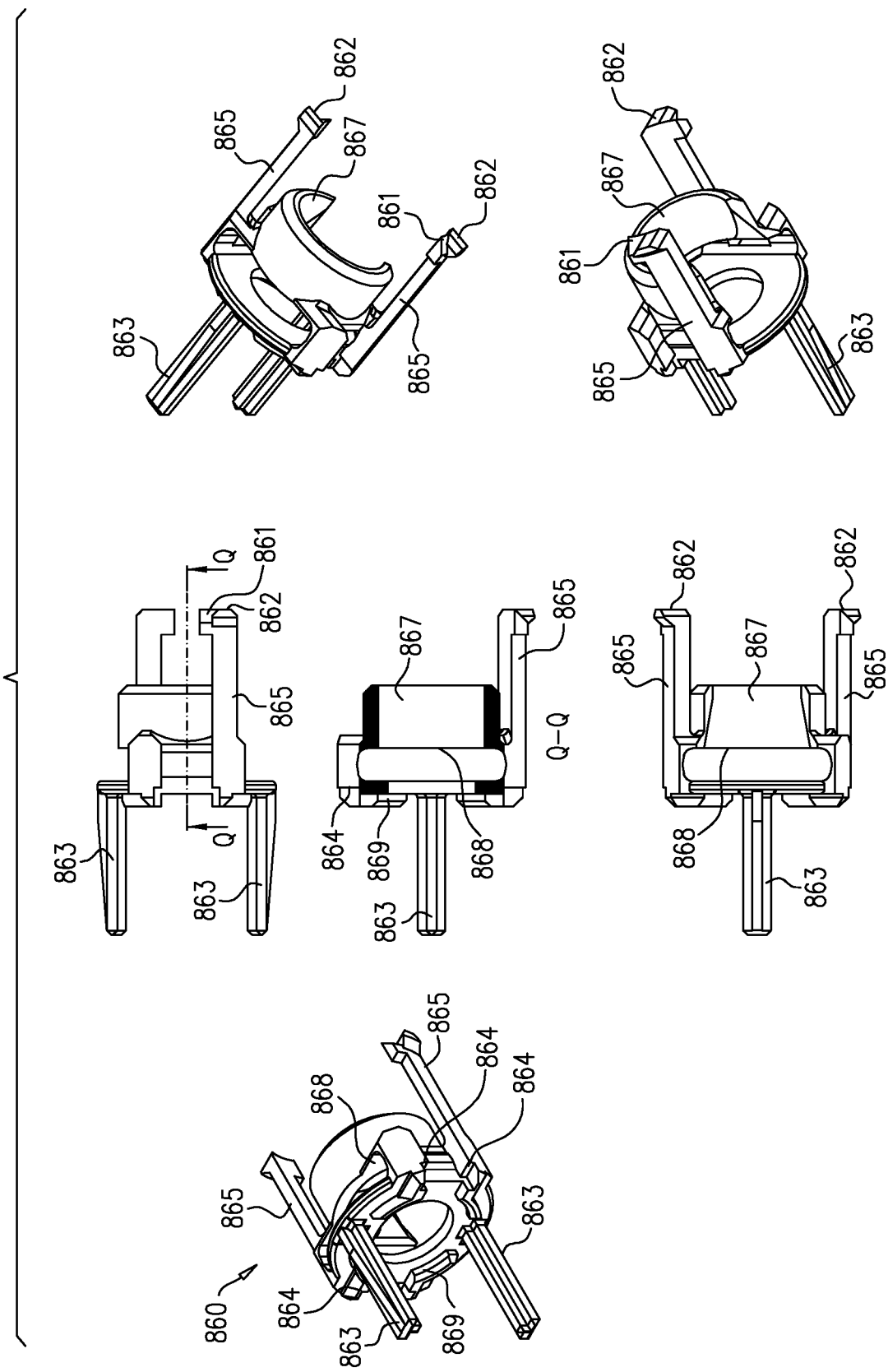

Referring to FIGS. 26A-26D, enlargements of the central components of the invention are presented, as follows:

Referring to FIG. 26A, syringe-support 860 is shown. As shown in isometric views at far right, syringe-support is generally similar to that of Embodiment 3, described in relation to FIG. 18D, including syringe flange seat 868 slot and syringe supporting rim, which are open at one side to accept an inserted syringe 100 and its flange 120. Also included are locking arms 865 with activation slope 861, which release the syringe-support from their locking position in the stop window 315p of the main housing 310, when an injection is triggered by a user.

However, syringe-support 860 has novel lengthened release fingers 863 are shown in FIG. 26A (isometric view far right), which interact with an alternatively designed interlock 550.

Referring to FIG. 26B, rear cap 380 is shown enlarged. Rear cap 380 is interchangeably denoted by either one of reference numerals 380 and 880.

Figure 26C:
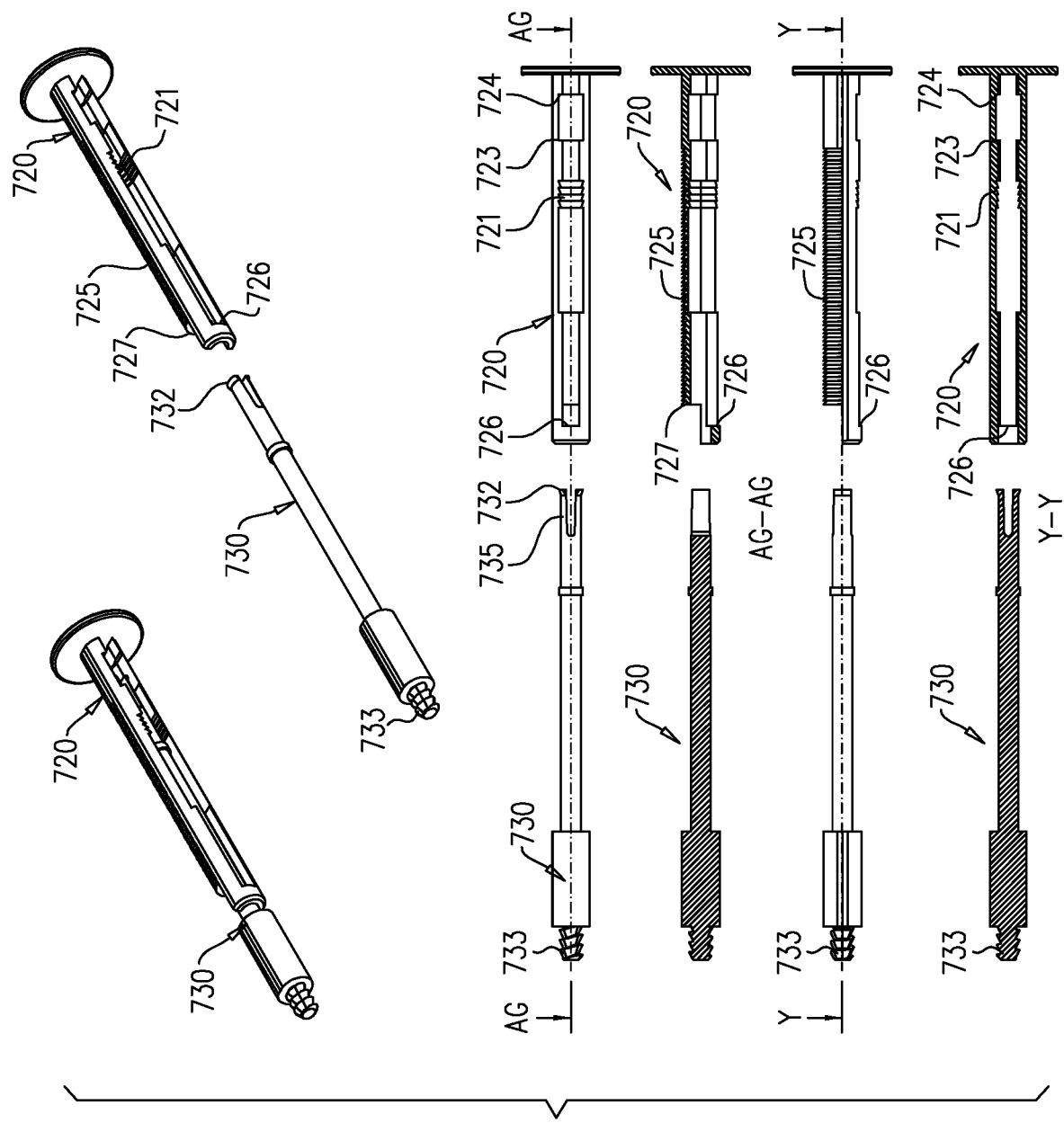
Figure 26D:
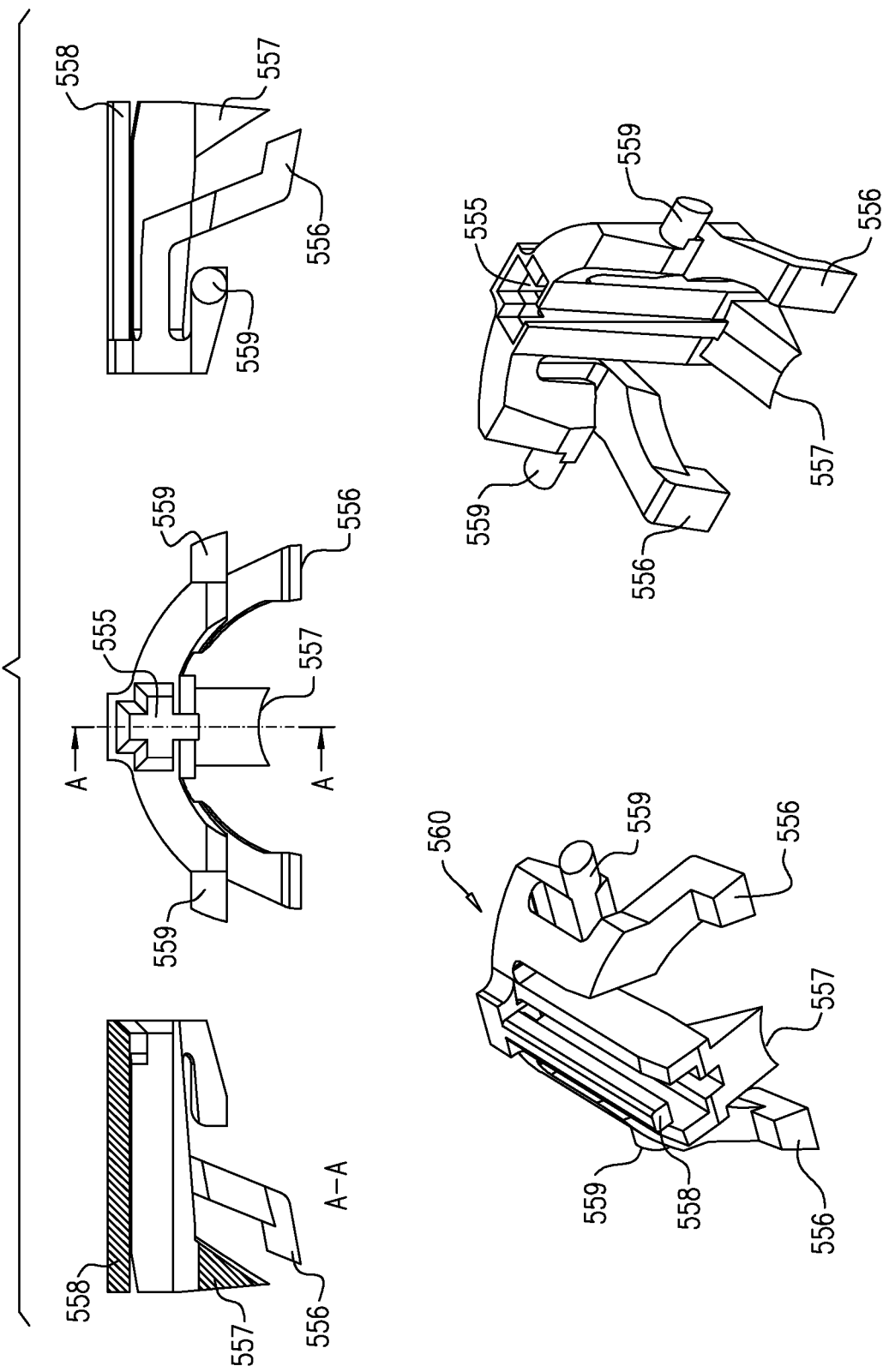

Rear cap 880 includes through-holes 887a and parallel through-hole 887b which accept and support pivot hinge 559 of interlock 550 (pivot shown in FIG. 26D). Through-holes 887a and 887b support interlock 550 to allow pivoting motion of interlock 550 upon the interlock pivot axis formed by pivot hinge 559. The pivoting motion either locks or releases the interlock from its hold on the proximal plunger 720.

Syringe spring rearward seat 882 is shown in section S-S (middle view).

Plunger Engagement Fingers 884 of the Rear Cap 880 are shown in Section AF-AF. The engagement fingers 884 prevent proximal movement of the Proximal Plunger 720 (extension of plunger instead of pressing of the plunger). The engagement fingers 884 lean distally against the Locking Faces 726 of Proximal Plunger 720, as shown in FIG. 27B, central illustration (Section B27.1-B27.1).

Ribs 888 of Rear Cap 880 oppose the flexible Load Beam 558 of the Interlock 550, and during release of the interlock 550 (described in relation to FIG. 30), load beam 558 of the interlock 550 is brought into pressure against ribs 888, generating tension or preload to re-lock the proximal plunger 720 by the interlock 550 when the needle shield 320 has moved distally to discard position.

Referring now to FIG. 26C, dual component plunger is shown, including the Proximal Plunger 720 and the Distal Plunger 730.

A certain amount of movement of the plunger components 720 and 730 with respect to one another, is allowed during storage, to allow for tolerances in positioning during the filling process of the Prefilled Syringe 100 and changes in air pressure (as described hereinabove in relation to FIG. 11B). Movement may occur between Minimal Air Point 723 up to the Maximal Air Point 724 of the Proximal Plunger 720 (best shown in cross-section Y-Y).

Novel locking teeth 725 are included on the proximal plunger 720, into which an Interlock locking Tooth 557 enters to lock the proximal plunger 720 from being prematurely pressed by a user.

Referring to lower-most sectional view Y-Y, to allow a user to timely press the plunger, proximal plunger 720 interacts with and moves distal plunger 730, via internal Ratchet Teeth 721 of Proximal Plunger 720, which engage with paired terminal Ratchet Teeth 732 of the distal plunger 730. This engagement is achieved by deflecting inwardly the Flexible Fingers 735 of the distal Plunger 730 on which the paired Ratchet Teeth 732 are formed.

In Section AG-AG (third from bottom), Locking Faces 726 of the Proximal Plunger 720 are shown, that engage the Plunger Engagement Fingers 884 of the Rear Cap 880 to prevent proximal movement of the Proximal Plunger 720 (extension of the lounger instead of pressing of the plunger).

Referring to FIG. 26D, lower isometric views, Interlock 550 of an alternative design is shown having a solitary terminal locking tooth 557 which enters locking teeth 725 of the proximal plunger 720 to prevent pressing of the plunger 720 by a user, prior to needle penetration, and during discard.

Interlock 550 includes a pair of Pivot Hinges 559 extending outwardly there-from. Pivot Hinges 559 enter and are supported by through-holes 887a and 887b of the rear cap 880. The Interlock 550 is urged by movement of the paired bracing legs 556, and by tension applied to Flexible Loading Beam 558, to pivot upon the axis provided by pivot hinges 559. This either releases or locks the proximal plunger 720 by interlock 550, by inserting or removing the solitary terminal locking tooth 557 from within the proximal plunger 720 locking teeth 725.

Referring to isometric view at top right, a cross-shaped Guiding Hole 555, is designed to mate with lengthened release fingers 863 of the Syringe-support 860. Thus, via this interaction, the syringe-support 860 prevents solitary terminal locking tooth 557 from exiting the proximal plunger 720 locking teeth 725, until the syringe-support 860 has advanced towards the injection site and removed lengthened release fingers 863 from guiding hole 555 of the interlock 550. The user will not succeed in pressing the proximal plunger 720 until the syringe-support 860 has advanced the needle to a complete penetrating position.

Figure 27A:
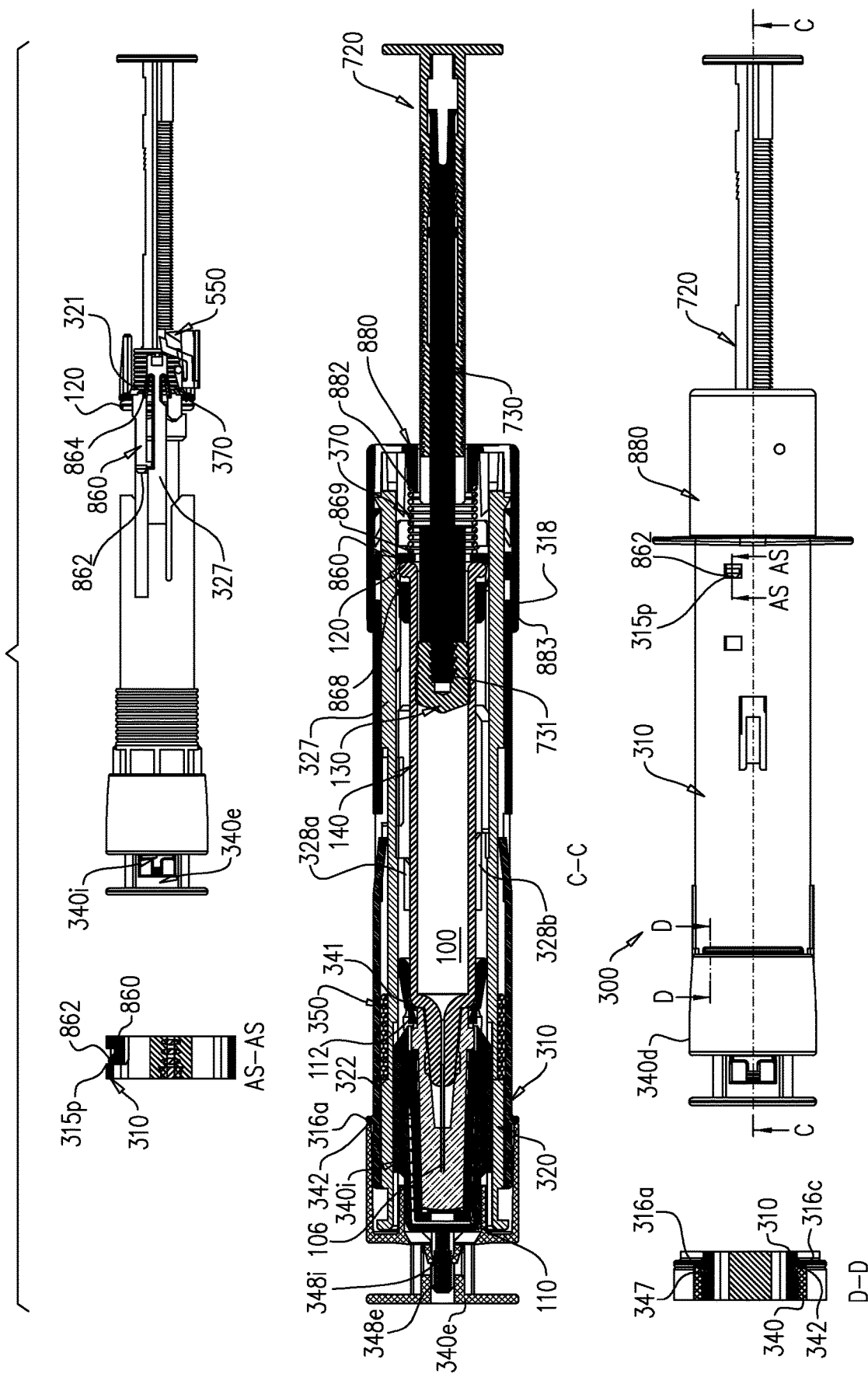
Figure 27B:
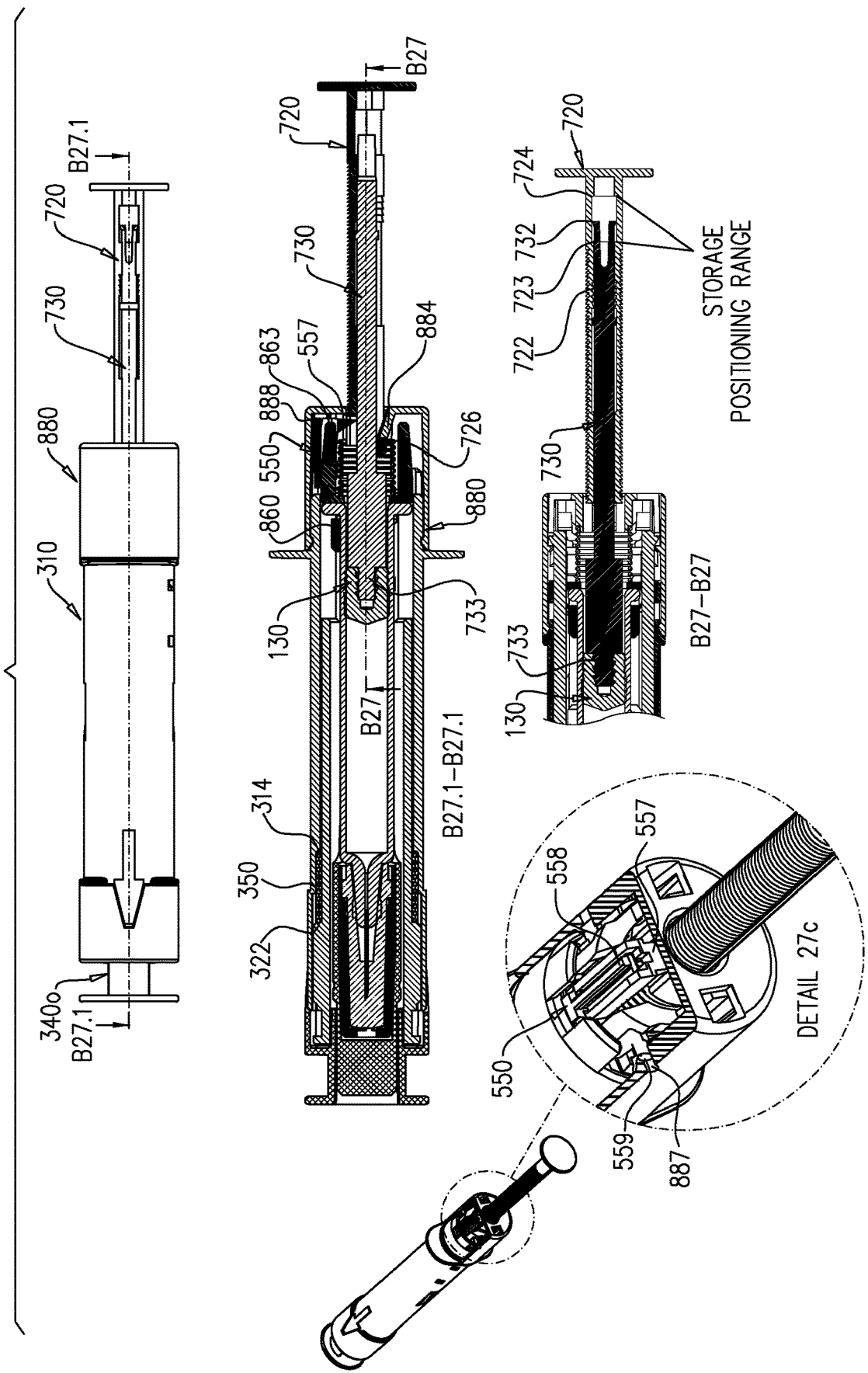

Referring now to FIG. 27A, central components are shown of the fourth embodiment of the device, after assembly and in the storage position. The following components have been removed, for viewing of internal components: the rear cap 880, the viewing window sticker 330 and the main housing 310. For simplicity and clarification, the sticker 330 has been removed from all other views, cross-sections and enlargements of FIG. 27A. Additionally, views and cross-sections were enlarged in different scales for increased clarification.

The Prefilled Syringe 100 is assembled into the Syringe-support 860 and is held axially in both distal and proximal directions by the Syringe Flange 120 engaging within the Groove 868 of the Syringe-support 860.

The Prefilled Syringe 100 is axially supported by and is allowed to slide upon two pairs of longitudinally Ribs 328a and 328b which are formed internally within the Needle Shield 320.

The Syringe Spring 370 is supported proximally on the Syringe Spring Backward Seat 882 of the Rear Cap 880. The Syringe Spring 370 urges the Syringe-support 860 distally by pushing on the Syringe Spring Forward Seat 869 of the Syringe-support 860.

The Forward Stop Face 862 of Syringe-support 860 engages in the Stop Window 315p of the Main Housing 310, thus preventing the Syringe-support 860 from moving distally.

Snap Fingers 321 of the Needle Shield Arms 327 of the Needle Shield 320 hold the Needle Shield 320 on the Shoulder 864 of the Syringe-support 860, thus preventing the Needle Shield 320 from moving distally.

The Rear Cap 880 is engaged to the Main Housing 310 by Connection Ring 883 of the Rear Cap 880 on Slot 318 of the Main Housing 310. This engagement can be of any form, such as a screw, a snap-fit, gluing, welding or any other suitable form. Alternatively, the Main Housing 310 and Rear Cap 880 can be a unitary part or separated into two or more parts in other locations.

Referring to FIG. 27B, for simplicity and clarification, the sticker 330 has been removed from all views, cross-sections and enlargements. Additionally, views and cross-sections were enlarged in different scales for increased clarification.

As shown in section B27-B27, during storage, the distal plunger 730 has not yet engaged the proximal plunger 720, and these components are allowed to move somewhat relative to one another, to allow for the tolerances or change in axial position of the Syringe Piston 130 at this stage. The paired terminal Ratchet Teeth 732 of the Distal Plunger 730, are not engaged in the counter-part internal Ratchet Teeth 721 of the Proximal Plunger 720. A storage positioning range of the Distal Plunger 730 is defined by points Min Air 723 up to the Max Air 724 of the Proximal Plunger 720, allowing for the positioning tolerances as explained hereinabove.

Plunger Engagement Fingers 884 of Rear Cap 880 lean distally against Locking Faces 726 of Proximal Plunger 720 thus preventing the proximal movement of the Proximal Plunger 720.

The Distal Tip 733 of the Distal Plunger 730 is connected by any method of bonding, welding, threading, one or more snaps, etc. to the Syringe Piston 130.

The Needle Shield Spring 350 is supported proximally on the Shield Spring Backward Seat 314 of the Main Housing 310. The Needle Shield Spring 350 urges the Needle Shield 320 distally by pushing on the Shield Spring Forward Seat 322 of the Needle Shield 320.

NS Remover Internal Part 343 is engaged to the NS 110 which conceals the Needle 106 and the Needle Tip 105 of the Prefilled Syringe 100.

Because the NS 110 axial position results in large axial tolerance, the NS Distal Rigid Rim 112 position may vary relative to the NS Remover stopper 316a of the Main Housing 310. Therefore a two-part NS remover is described, having an Internal Part 343 and an External Part 340 which are engaged through Ratchet Teeth 348i of the NS Remover Internal Part 343 and Flexible Teeth 348e of the NS Remover External Part 340. The ratchet mechanism enables engagement of the two parts during assembly at the required axial position, while having them lock for removal of the NS 110.

In case of shock applied through accidental drop on the distal end of the NS Remover 340, the NS Remover External Part 340 of the NS remover assembly 340 will come in contact with the NS remover stopper 316a of the main housing 310 thus limiting the force transmitted via NS Remover 340 to the prefilled syringe 100. This feature reduces chances for breakage of the Syringe Barrel 140 and/or it's Flange 120, which may be produced from glass.

Referring back to FIG. 27A, enlarged section D-D at bottom left, NS Remover External Part 340 has four internal Protrusions 347 which engage into four circumferentially located Slots 316c, which are formed adjacent to and distally of the Stopper 316a of the Main Housing 310. Protrusions 347 retain NS Remover External Part 340 and prevent its movement distally during storage. Such Protrusions 347 and Slots 316c can be of any number, formed as flexible snap-fits, etc. Additionally, they can be formed such that the protrusions are formed in the Main Housing 310 and the slots are formed in the NS Remover External Part.

Alternatively, the NS Remover External Part 340 may be fit to the Main Housing 310 using a sticker that has to be removed or torn before removing the NS. The sticker can be evidence that the syringe has not been tampered with. Furthermore, the NS Remover External Part 340 can be welded/glued to the Main Housing 310 in a relatively weak welding, breakable by the user.

Sticker 330 is attached on the Main Housing 310. The Sticker 330 can be made of transparent material, opaque, or partially opaque. The SAN-P device 40 can be also produced without a Sticker 330, or with another external component preferably made of plastic, alternatively to sticker 330.

Referring to FIG. 27B, Detailed Enlargement cut-away "Detail 27c", the Interlock 550 is engaged inside the Rear Cap 880 by engagement of Pivot Hinges 559 in Holes 887a and 887b of Rear Cap 880 such that Locking Tooth 557 of Interlock 550 is facing inwardly and proximally.

Figure 27C:
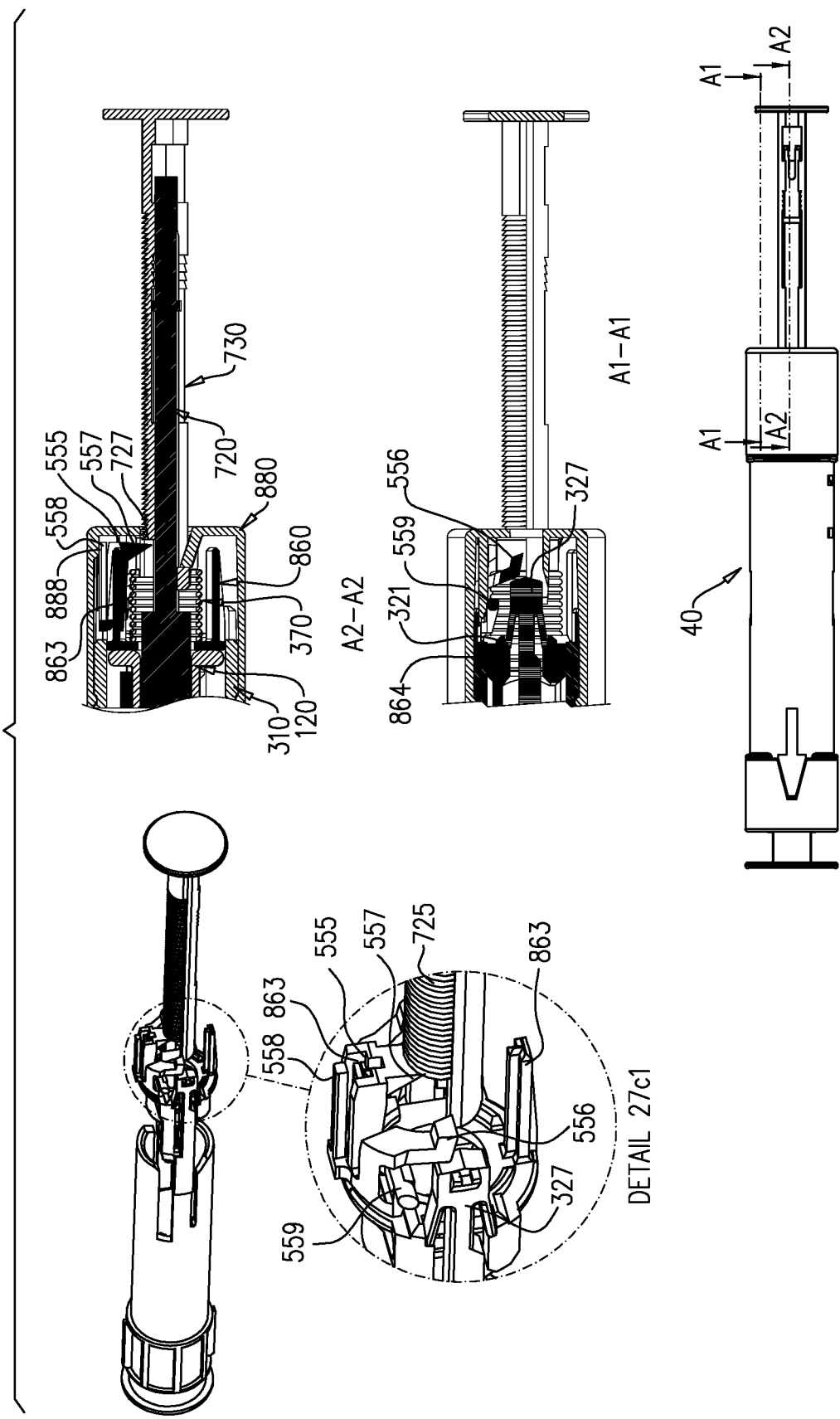

Referring to FIG. 27C, for simplicity and viewing of internal components isometric side-view is shown without the following components: the two-part NS Remover (340, 343), the rear cap 880, the viewing window sticker 330 and the main housing 310. For simplicity and clarification the sticker 330 has been removed from the bottom view, and cross-sections A1-A1 and A2-A2 are shown enlarged.

As seen in "Detail 27c1", the Flexible Beam 558 of the Interlock 550 is positioned such that it is unloaded, lying in its natural position facing outwardly towards internally facing Ribs 888 of Rear Cap 880.

One of lengthened release fingers 863 of the Syringe-support 860 is located within guiding hole 555 of the interlock 550. The other finger 863 is not functional and is only shown for simplifying the production process by allowing assembly of the syringe-support 860 in two orientations.

Paired bracing legs 556 of the Interlock 550 (which are outwardly and inwardly facing), are positioned such that they are unloaded, lying in their natural position.

Referring to 27C, Section A2-A2, the Proximal Plunger 720 is blocked from moving distally by engagement of the Interlock's Locking Tooth 557, within the Forward Facing Edge 727 (indicated in FIG. 29B Section B2-B2) of the proximal plunger locking teeth 725. This feature reduces the risk of user error (premature plunger press and premature discharge of fluid) as this prevents unintended spill-out of medication through the needle before the needle has penetrated the injection site. Such premature fluid or medication spill-out may cause an under-dose of medication, or skin irritation.

Referring to FIG. 27C, isometric side-view "Detail 27c1", the lengthened release finger 863 of the Syringe-support 860, ensures the Locking Tooth 557 of the Interlock 550 won't move outwardly away from the Proximal Plunger 720 as long as the lengthened release finger 863 is positioned within the Guiding Hole 555 of the interlock 550.

Figure 28:
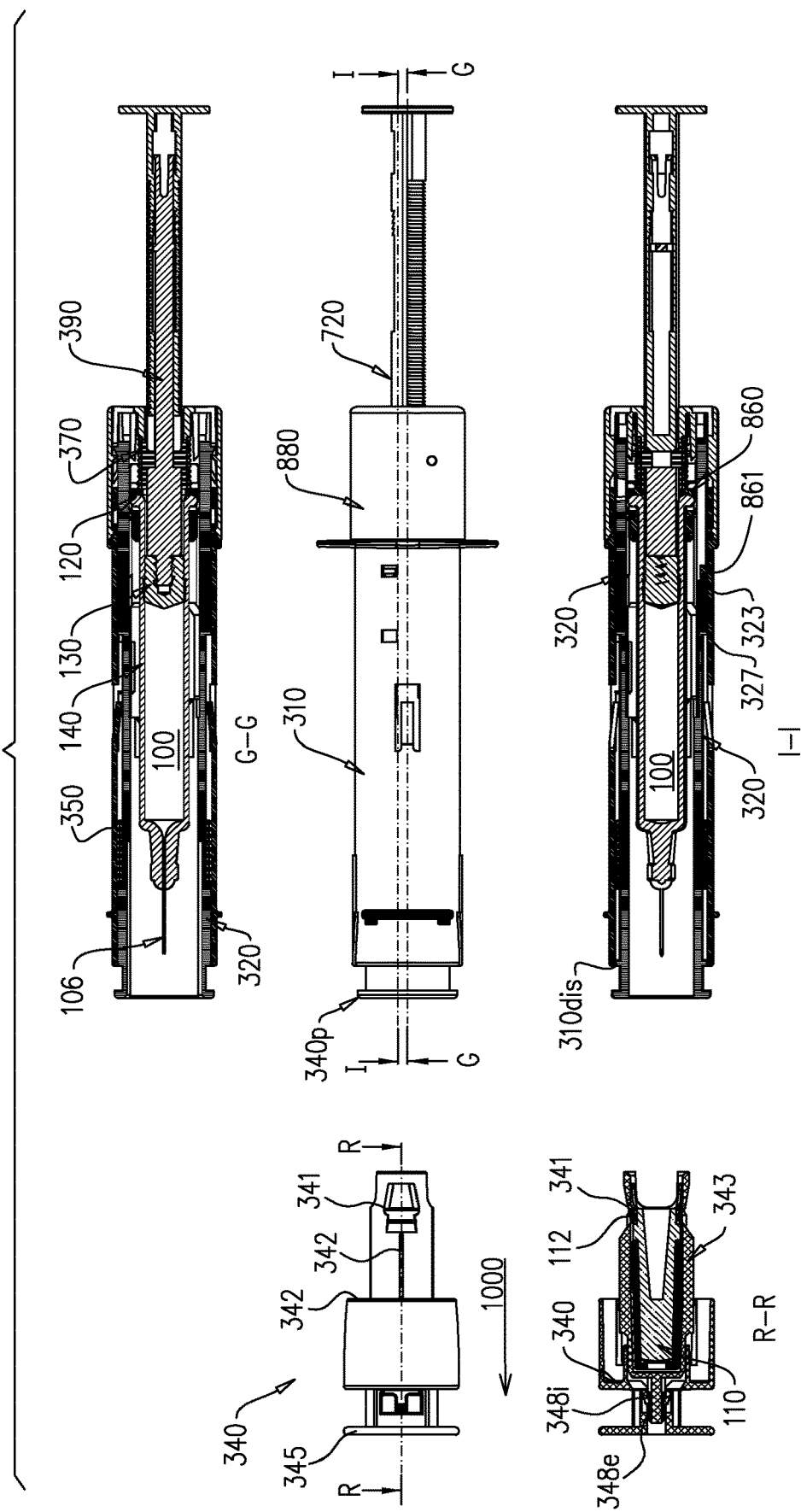

Referring now to FIG. 28, for simplicity and clarification the sticker 330 has been removed from the side view (shown in the middle), and the cross-sections G-G and I-I. In FIG. 28 the two-part NS Remover (340, 343) has been removed by the user, along with the NS 110. No changes have occurred in the position of any other part the SAN-P device 30.

The NS 110 has been removed by pulling the NS Remover External Part 340 distally in direction 1000. NS Remover Internal Part 343 is pulled away together with NS Remover External Part 340 by engagement of Flexible Teeth 348e of the NS Remover External Part 340 with Ratchet Teeth 348i of the NS Remover Internal Part 343. NS Remover Snap Teeth 341 of NS Remover Internal Part 343 grab the NS Distal Rigid Rim 112 of NS 110.

In order to protect the Needle 106 from damage, during removing the NS Remover assembly 340 and the NS 110, the NS Remover assembly 340 is guided axially on the Needle Shield 320 thus preventing any bending load on the Needle 106. The Needle 106 remains hidden throughout this stage. It can be understood that there can be one or more NS Remover Snap Teeth 341. NS Remover Snap Teeth 341 of NS Remover Internal Part 343 keep the NS 110 within the NS Remover assembly, thus preventing a potential choking hazard. It can be understood that there can be one or more NS Remover Snap Teeth 341.

Figure 29A:
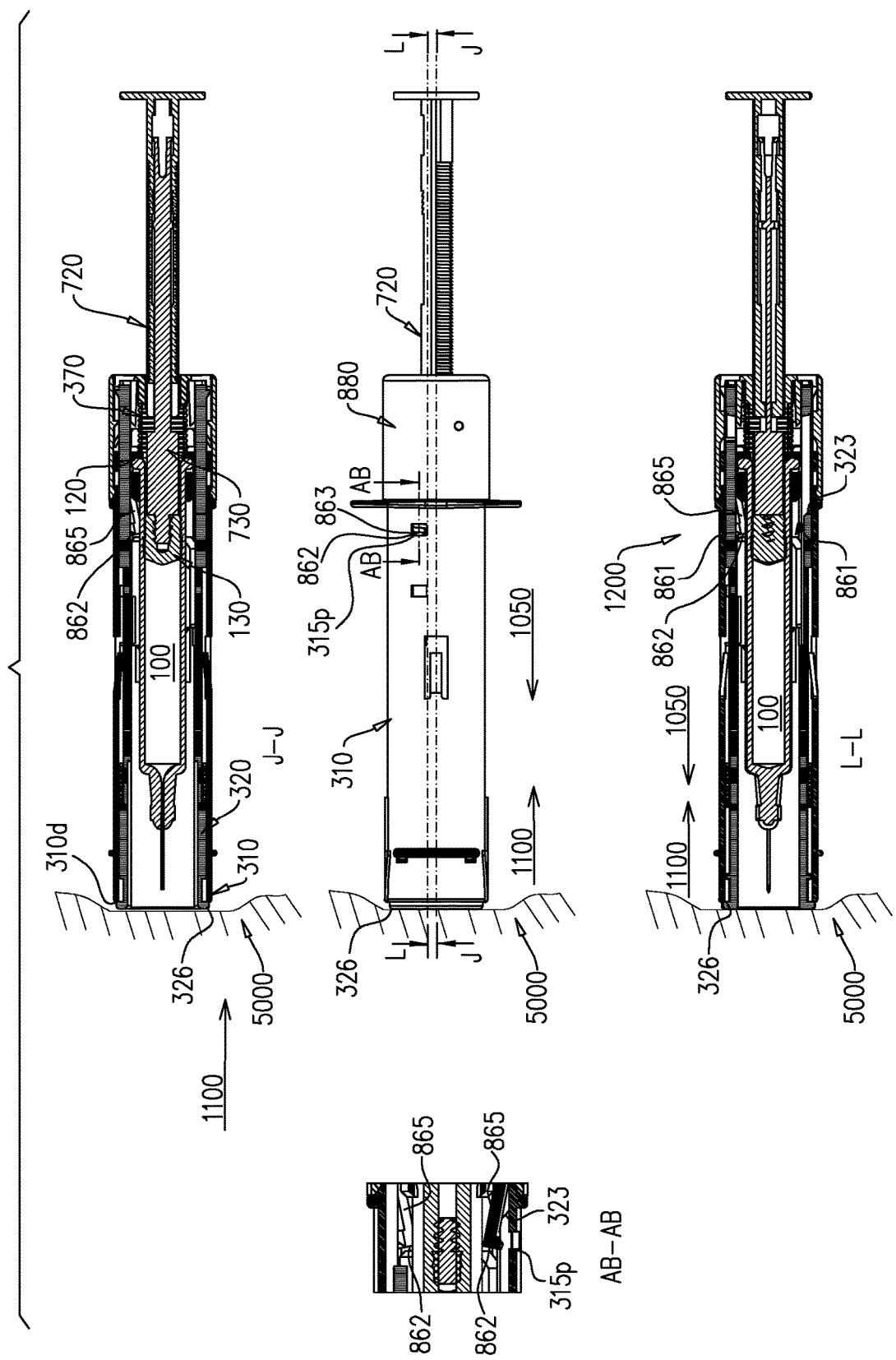

Referring to FIG. 29A, for simplicity and clarification the sticker 330 has been removed from the side view (shown in the middle), and all the cross-sections. In FIG. 29A a user initiates the injection process by pressing the SAN-P device 40 against an Injection Site 5000 in the distal direction 1050. The terminal Ring 326 of the Needle Shield 320 is forced to move proximally in direction 1100.

In top-most view, the Ring 326 of the Needle Shield 320 stops on the Distal Edge 310d of the Main Housing 310.

In sectional view L-L, similarly to Embodiment 3, during proximal movement of Needle Shield 320, Activation Slope 323 of Needle Shield 320 slides against Activation Slope 861 of the Syringe-support 860 and bends the Locking Arm 865 inwardly. Note position of slope 861 relative to slope 323, as compared to their previous relative positions in FIG. 28 (right most image).

In Enlargement AB-AB, this inward bending of Locking Arm 865 of the Syringe-support 360 disengages the Forward Stop Face 862 from within the Stop Window 315p of the Main Housing 310 and allows the Syringe-support 860 to move distally with the Prefilled Syringe 100, urged by syringe spring 370.

Figure 29B:
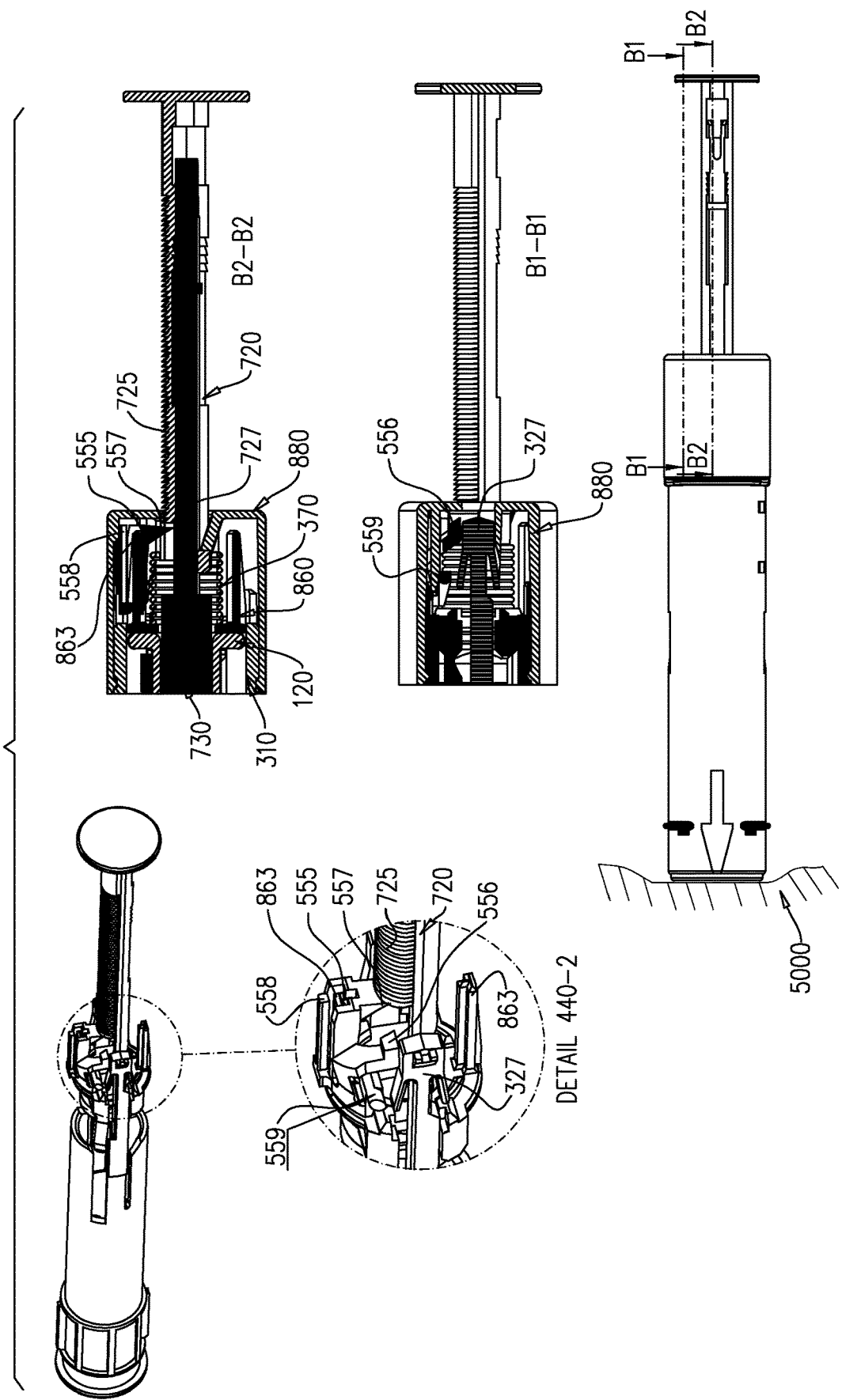

Referring to FIG. 29B, for viewing of internal components isometric side-view is shown without the following components: the rear cap 880, the viewing window sticker 330 and the main housing 310. For simplicity and clarification the sticker 330 has been removed from the bottom view, and cross-sections B1-B1 and B2-B2 are shown enlarged. In sectional view B1-B1, during proximal movement of Needle Shield 320, the Needle Shield Arms 327 of the Needle Shield 320 move proximally and engage the Legs 556 of the Interlock 550 and force them to bend outwardly.

In 29B, Section B2-B2, bending the Legs 556 of Interlock 550 creates a load or torque relative to the Pivot Hinges 559 of Interlock 550 urging the Locking Tooth 557 of Interlock 550 to move radially outwardly. However, radial movement of the Locking Tooth 557 of Interlock 550 is blocked by the lengthened release finger 863 of the Syringe-support 860; thus locking tooth 557 is still blocking the distal movement of the Proximal Plunger 720. Any attempt to press the Proximal Plunger 720 distally and inject the drug, is thus prevented at this stage.

Figure 30A:
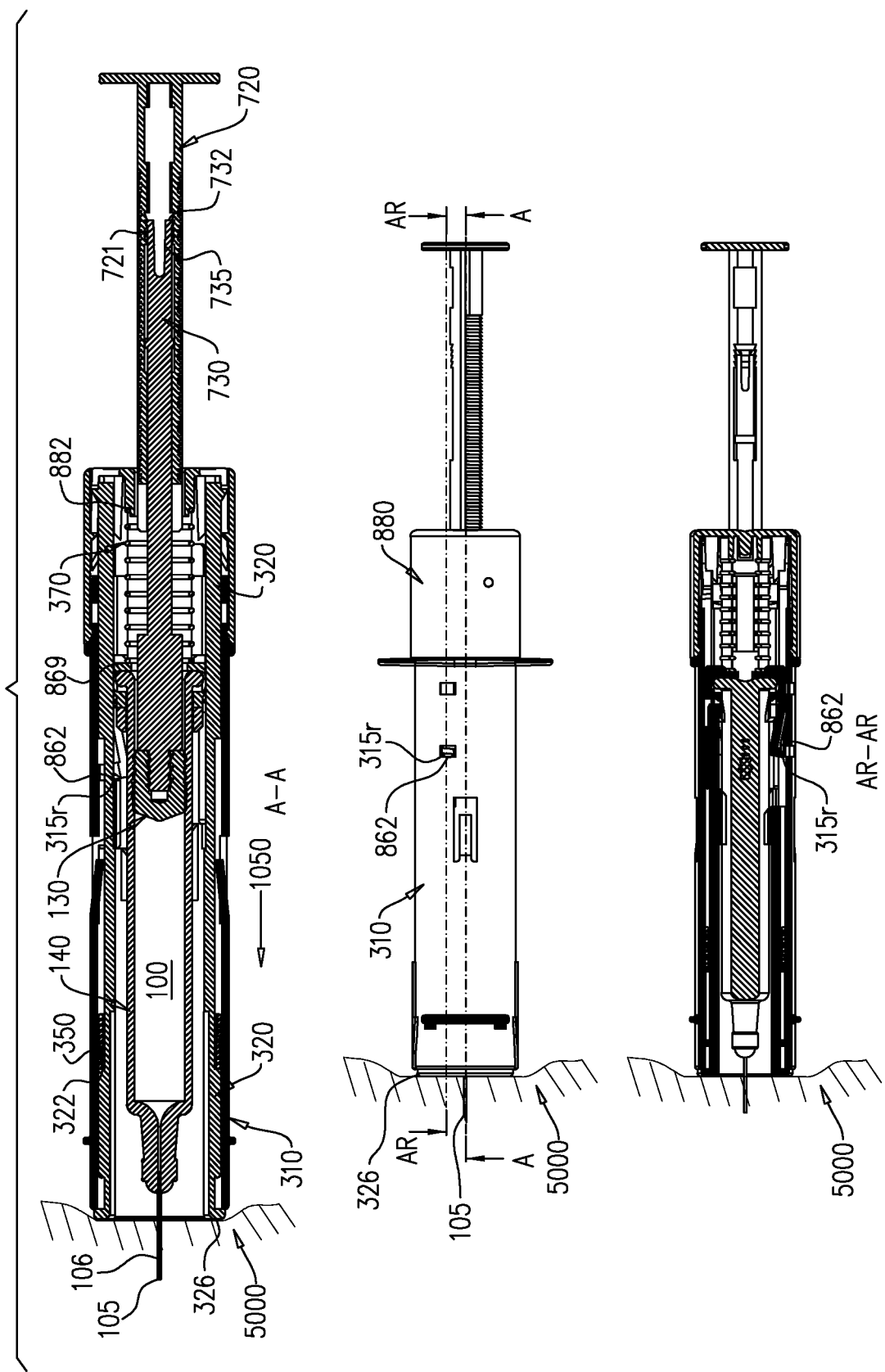

Referring to FIG. 30A, for simplicity and clarification the sticker 330 has been removed from the center view, and cross-sections 30A-30A is shown enlarged. In FIG. 30A complete needle penetration has occurred. In view 30A-30A, urged by extension of the compressed Syringe Spring 370, the Syringe-support 860 was urged together with Prefilled Syringe 100 by the Syringe Spring 370 and moved distally until Forward Stop Face 862 of Syringe-support 860 stops on Stopping Ribs 315r of Main Housing 310 (also shown in center illustration and similarly in Embodiment 3).

The Needle Tip 105 of the Prefilled Syringe 100 has penetrated to the appropriate depth into the injection site 5000.

In FIG. 30A, cross-section A-A, the Distal Plunger 730 which is connected to the Syringe Piston 130, has moved, along with the Prefilled Syringe 100. The Distal plunger 730 has engaged with the proximal plunger 720, as follows: The paired terminal Ratchet Teeth 732 of the distal plunger 730 have moved distally and engaged with the internal Ratchet Teeth 721 of the Proximal Plunger 720. This engagement is achieved by deflecting inwardly the Flexible Fingers 735 of the distal Plunger 730 on which the paired Ratchet Teeth 732 are formed.

The specific tooth engaged, from among the internal Ratchet Teeth 721 of the Proximal Plunger 720, depends on the initial axial position of the Syringe Piston 130 and various assembly tolerances.

Referring to FIG. 30B, for viewing of internal components isometric side-view is shown without the following components: the rear cap 880, the viewing window sticker 330 and the main housing 310. For simplicity and clarification the sticker 330 has been removed from the bottom view, and cross-sections C1-C1 and C2-C2 are shown enlarged. In FIG. 30B section C2-C2, the lengthened release finger 863 of the Syringe-support 860 has moved distally and is no longer located within the guiding hole 555 of the Interlock 550. Therefore, the locking Tooth 557 of the Interlock 550 is allowed to move radially outwardly away from the Forward Facing Edge 727 of the Ratchet Teeth 725 of the Proximal Plunger 720. The Proximal Plunger 720 may then move distally when pressed by a user, to perform an injection.

Referring to isometric view (Detail G), movement of the Tooth 557 of Interlock 550 radially outwardly, is due to the urging torque created by the bending motion of the paired bracing Legs 556 of the Interlock 550, executed by the Needle Shield Arms 327 of the Needle Shield 320 as detailed above.

Due to rotation of the Interlock 550 with respect to the Pivot Hinges 559, the paired bracing Legs 556 of Interlock 550 have become nearly unloaded, and the Load Beam 558 of the Interlock 550 is banded against the Ribs 888 of the Rear Cap 880 and become loaded urging the Locking Tooth 557 of the Interlock 550 to move back inwardly.

The Load Beam 558 banding force is lighter than the force required to band Legs 556.

The Proximal Plunger 720 may then move distally when pressed by a user, to perform an injection as described herein-below.

Figure 31:
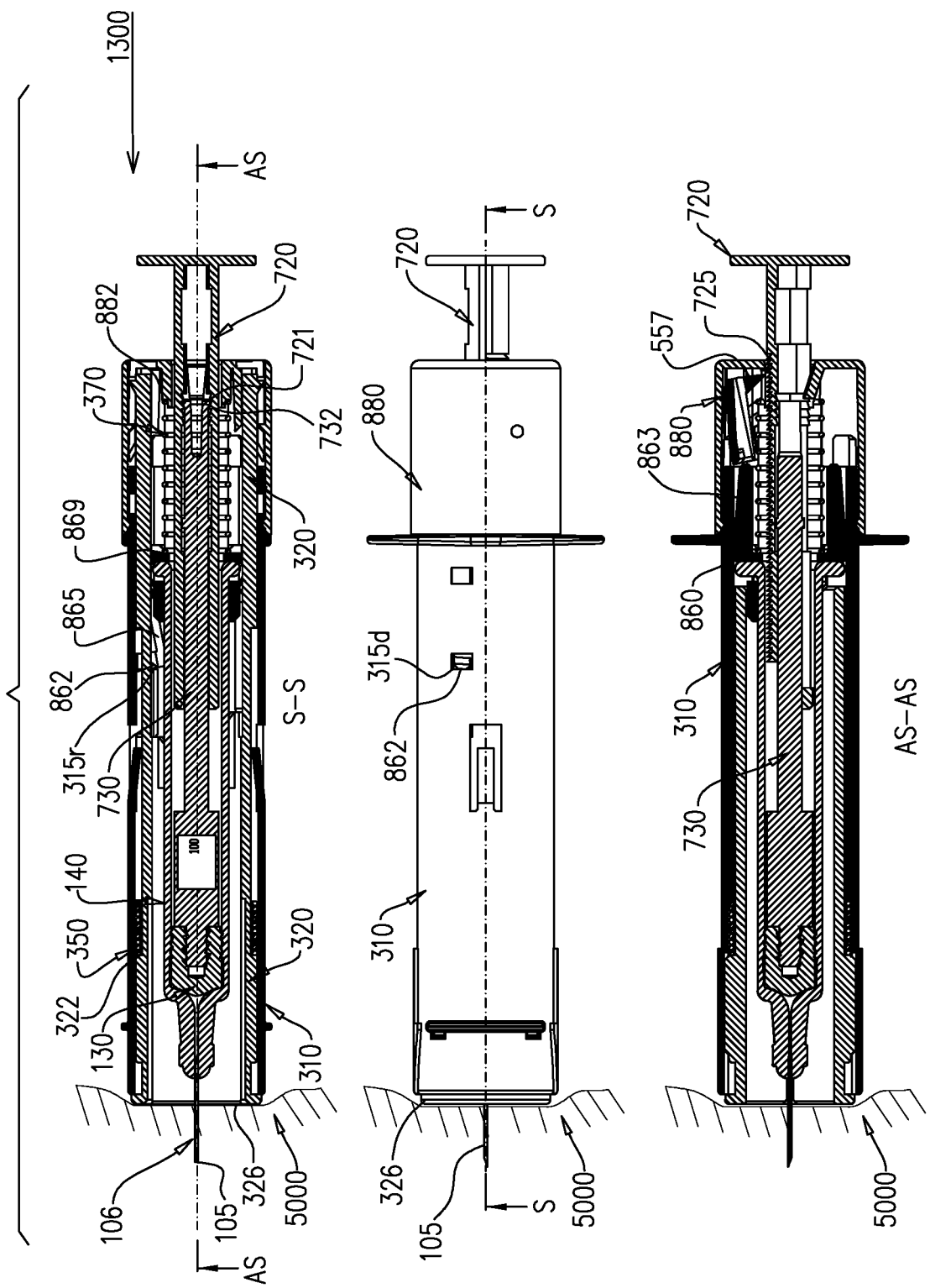

Referring now to FIG. 31, for simplicity and clarification the sticker 330 has been removed from the center view, and cross-sections S-S and AS-AS. In cross-section S-S, "delivery" stage, a user may now press the Proximal Plunger 720 in the distal direction 1300. The engagement between the internal Ratchet Tooth 721 of the Proximal Plunger 720, with the terminal Ratchet Teeth 732 of the distal plunger 730, forces the Distal Plunger 730 to move distally, together with the Piston 130, therefore injecting the fluid via the Needle Tip 105.

At the end of injection, the Piston 130 reaches the front end of the Syringe Barrel 140 and stops, indicating to the user that the injection is complete.

Figure 32A:
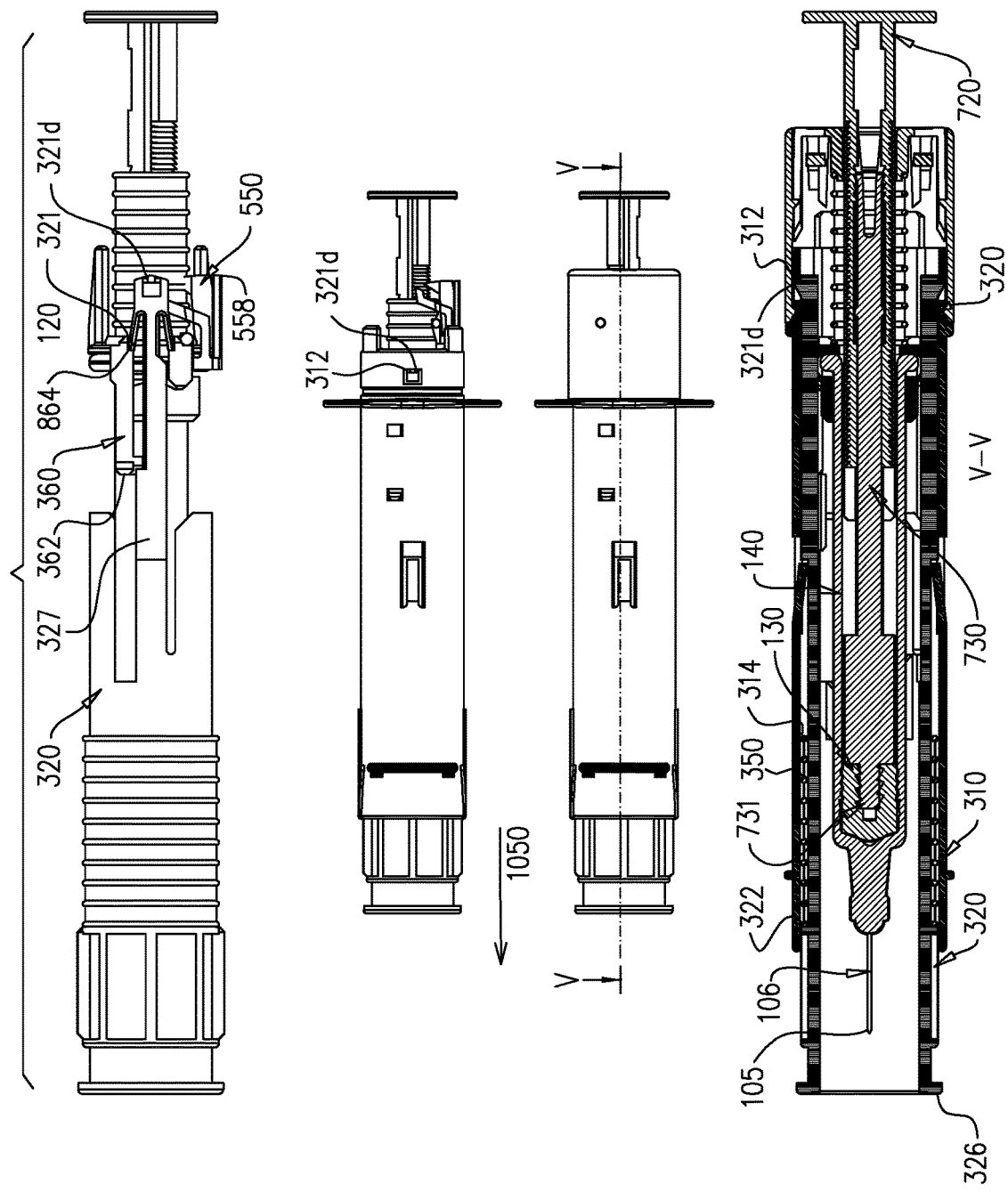
Figure 32B:
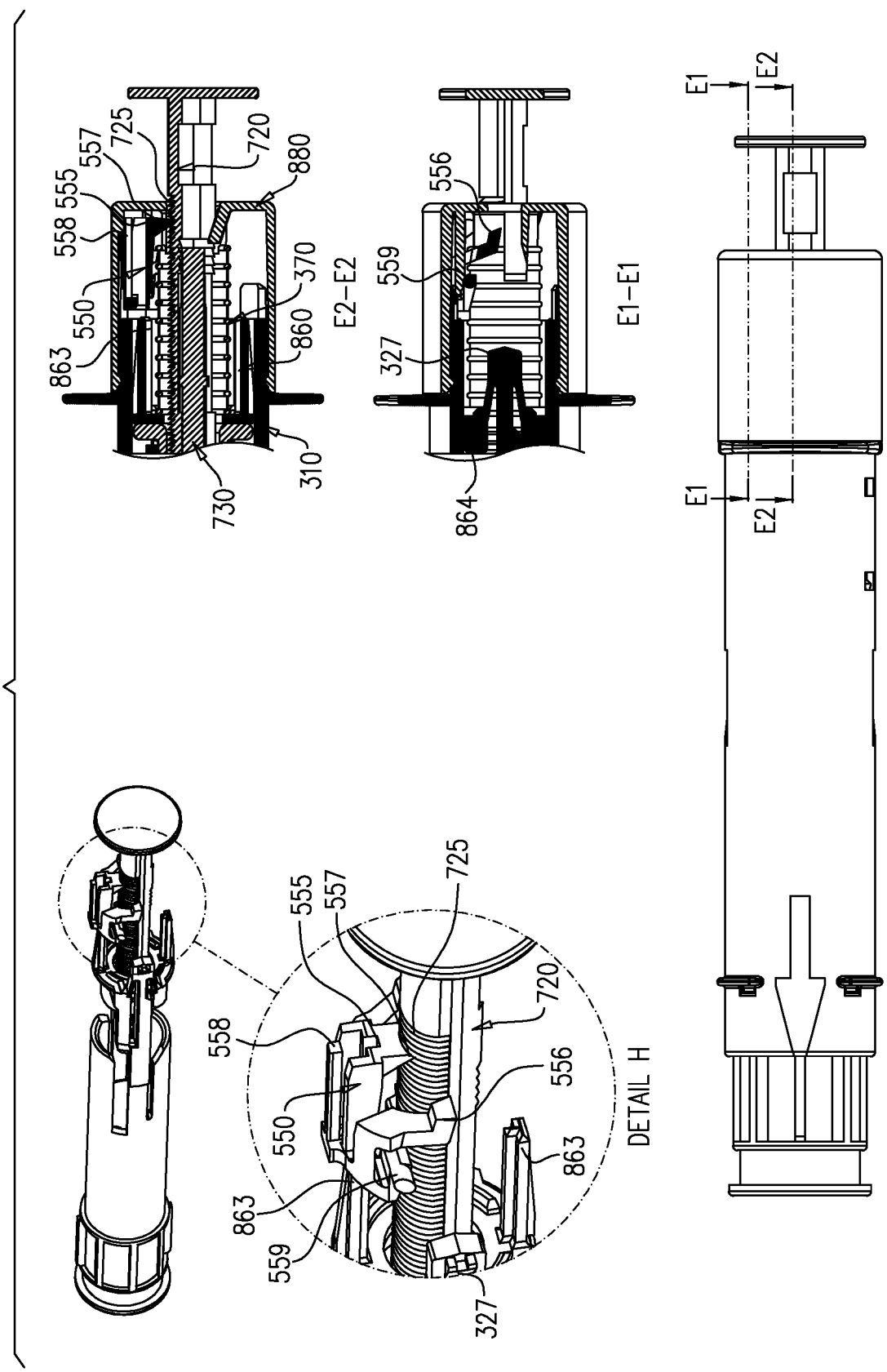

Referring to FIGS. 32A and 32B, the device is shown in the "discard" stage, namely automatic needle shielding occurs after a user removes the SAN-P device 40 from the injection site 5000. In the top view of FIG. 32A, rear cap, main housing and sticker have been removed to view internal components. In the second view from the top, rear cap and sticker have been removed to view internal components. The sticker has been removed for simplicity in the second view from bottom and enlarged section V-V at the bottom.

As shown in upper-most illustration (shown enlarged), distal movement of the needle shield 320 is arrested when the Snap Fingers 321 of the Needle Shield 320 stop upon Shoulder 864 of the Syringe-support 860.

At this stage, the Needle Tip 105 is safely concealed by the Needle Shield 320 and cannot be re-exposed.

The needle shield is locked in this position by the following mechanism: the proximal face of outward- and rearward-facing Protrusions 321d of the Needle Shield 320 engage with cutout 312 of the main housing 310 (shown in second view from top). In this state, reuse and inadvertent needle-sticks cannot occur from a used needle.

Referring to FIG. 32B, for viewing of internal components isometric side-view is shown without the following components: the rear cap 880, the viewing window sticker 330 and the main housing 310. For simplicity and clarification the sticker 330 has been removed from the bottom view. In FIG. 32B section E1-E1 the interlock position is shown in the "discard" stage. The needle Shield Arms 327 of the Needle Shield 320, have moved distally to the "discard position", the paired bracing Legs 556 of the Interlock 550 are no longer urged by the Needle Shield Arms 327 outwardly. The bracing legs 556 return inwardly, with Locking Tooth 557 of the Interlock 550 by the force applied by the load of Beam 558 of the Interlock 550.

As shown in isometric view (Detail H), the Locking Tooth 557 engages with one of the Proximal Plunger 720 Locking Teeth 725; this locks the Proximal Plunger 720 from further movement distally. The plunger can no longer be pressed by a user, thus discharge of any remaining medication is prevented, to avoid biohazardous spills.

It can be understood, that while here the locking movement was shown in the distal direction, the locking can be similarly designed to lock towards movement in the opposite direction, i.e., the proximal direction by designing the Locking Tooth 557 and Locking Teeth 725 of the Proximal Plunger 720 in the opposite direction.

Figure 33A:
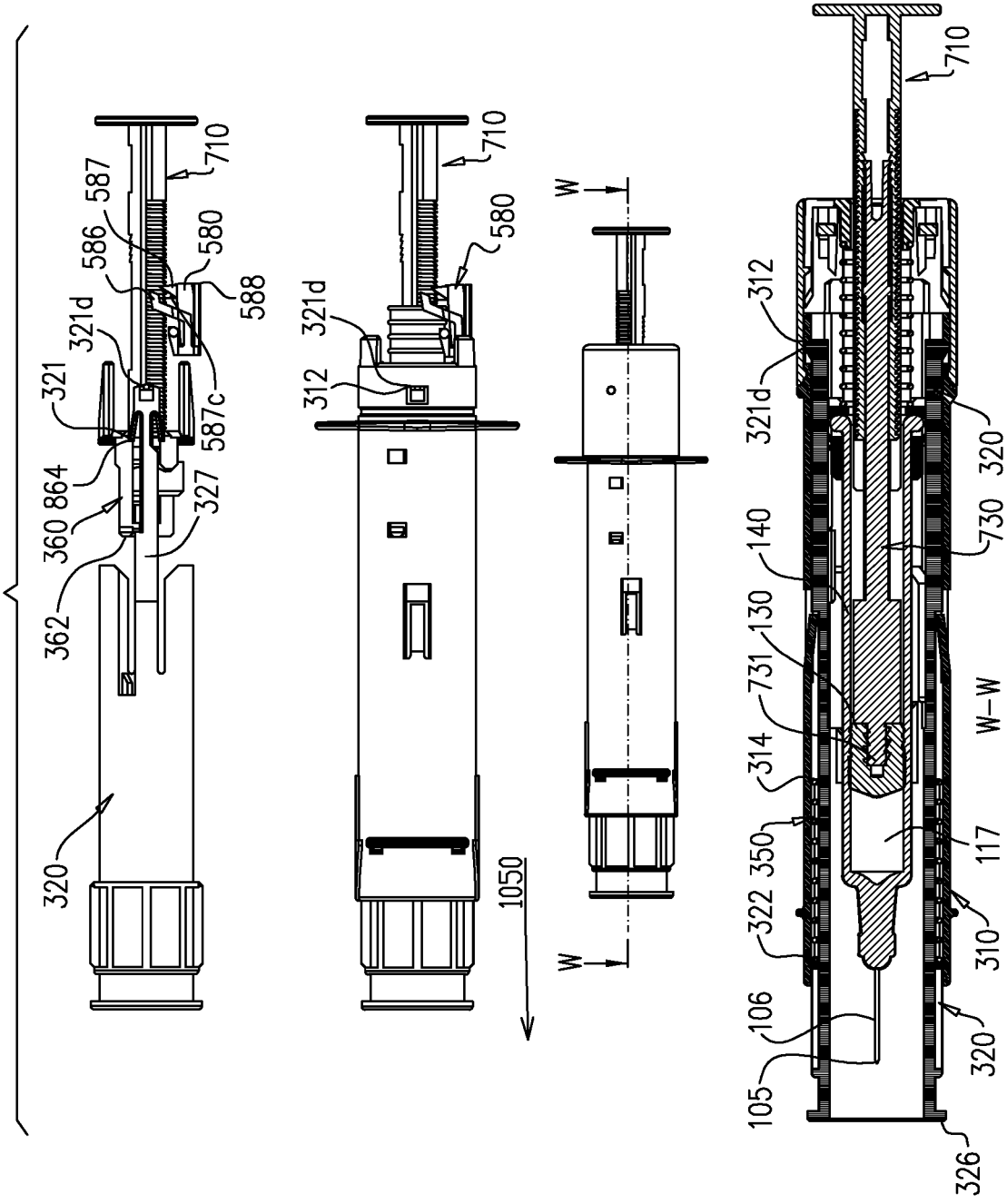
Figure 33B:
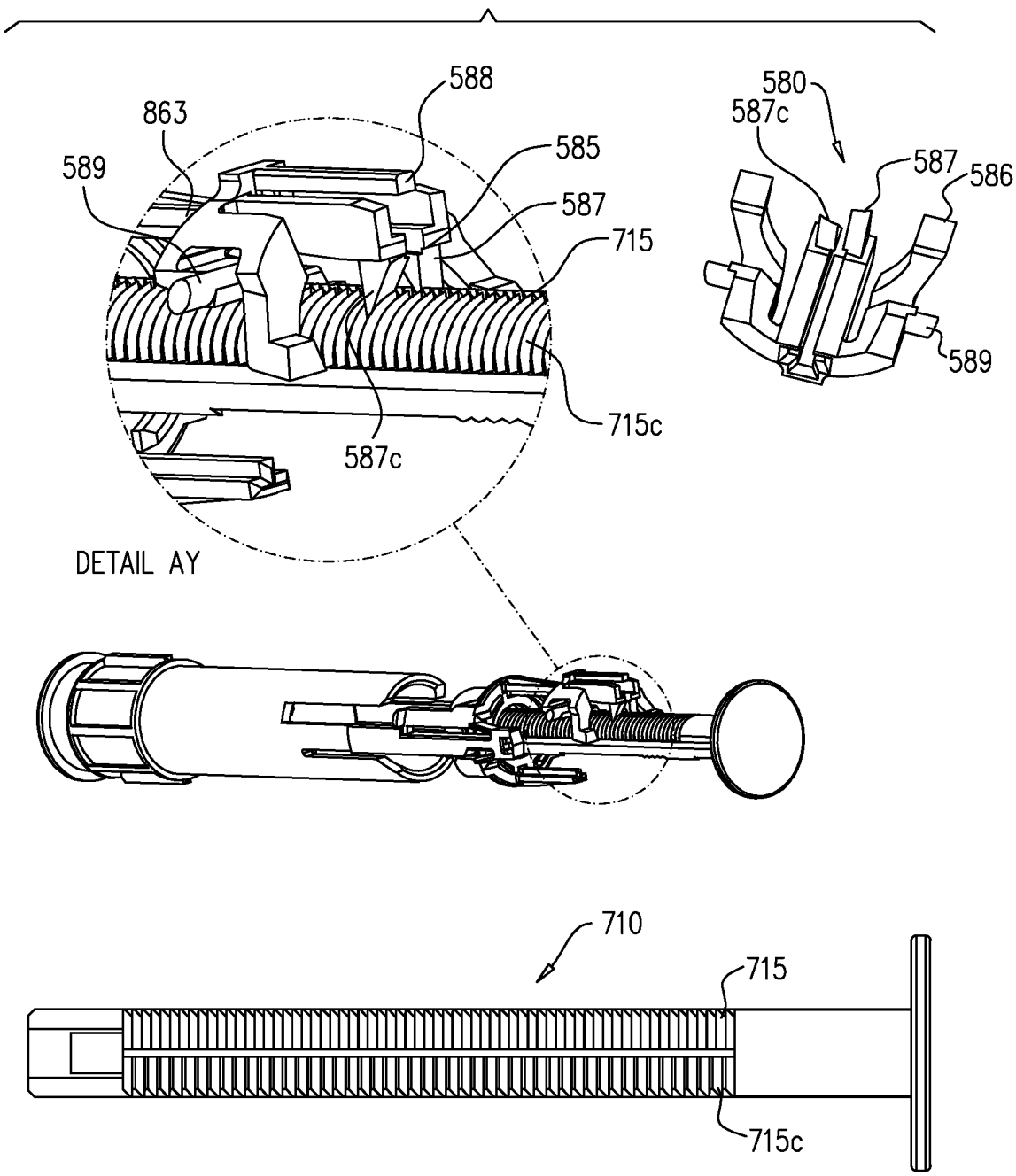

Referring now to FIG. 33A-33C, another embodiment of the invention is described, in which the proximal plunger is locked in both axial directions, prior to needle penetration, and in the "discard" state. In FIG. 33A, for viewing of internal components top view is shown without the following components: the rear cap 880, the viewing window sticker 330 and the main housing 310. For simplicity and clarification the sticker 330 has been removed from the both views in the center, and enlarged cross-section W-W.

Referring to FIG. 33B, for viewing of internal components isometric view in the center is shown without the following components: the rear cap 880, the viewing window sticker 330 and the main housing 310. In the upper isometric enlargement, the interlock's terminal locking tooth is split into two terminal locking teeth 587 and 587c, with each tooth angled in a different direction. See enlargement of interlock at top right, where angles of teeth 587 and 587c are shown.

These two interlock teeth 587 and 587c, enter and engage appropriate proximal plunger external locking teeth 715 and 715c, which are also angled in opposite directions relative to one another.

This engagement locks and prevents movement of the Proximal Plunger 710 in both axial directions, so that the plunger cannot be pressed (prior to advancement of the syringe-support to a needle penetration position) and the plunger also cannot be extended.

In addition, as seen in FIG. 33C (for simplicity and clarification the sticker 330 has been removed from the view in the center, and both enlarged cross-sections AZ-AZ and AU-AU), the SAN-P device 40 is shown after its removal from the injection site 5000 before the injection was complete, either accidentally, or, for instance, when the user is required to inject a dose which is smaller than the amount prefilled in the Prefilled Syringe 100. Thus, residual fluid 117 remains in the Prefilled Syringe 100.

In this situation, as in the case where the full dose was injected (shown in previous figures), the Needle Shield 320 moves distally relative to the Main Housing 310 urged by the Needle Shield Spring 350. The Needle Tip 105 of the Prefilled Syringe 100 is safely concealed by the Needle Shield 320. The Needle Shield 320 is locked from axial movement in both directions, as described in relation to FIGS. 32A and 32B above.

As Needle Shield Arms 327 of the Needle Shield 320 move distally to the "discard position", the bracing Legs 586 of the Interlock 580 are no longer urged by the Needle Shield Arms 327 outwardly and return inwardly with Locking Teeth 587 and 587c of the Interlock 580 by the load of Beam 588 of the Interlock 580. The Locking Teeth 587 and 587c engage the Locking Teeth 715 of the Proximal Plunger 710 and lock the Proximal Plunger 710 from further movement both distally and proximally.

Locking the Proximal Plunger 710 in both directions may be important as some types of drugs are toxic and may cause skin irritation or local reactions if accidentally expelled onto the skin.

In summary, the safe auto-needle device (SAN-P) of the invention, provides a user with an inexpensive injection device, which allows a user to control the rate of injection to alleviate pain, and has various safety features: premature discharge of the medication, and discharge of remaining medicinal drops are prevented by the presence of an interlock, extension of the plunger instead of pressing it is prevented by inclusion of locking segments upon the plunger, breaking and bending of the needle is prevented by inclusion of an NS remover providing damping, automatic needle shielding is provided by the needle sheath which is locked for discard.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A safe auto-needle device for injection, comprising:
 a) a main housing;
 b) a syringe-support for receiving a proximal end of a disposable prefilled syringe;
  said disposable prefilled syringe comprises: a piston; a proximal end including a flange; and a distal end terminating in a needle; said needle covered by a needle sheath (NS);
 c) a drive mechanism for advancing said syringe-support distally towards an injection site;
 d) a generally tubular needle shield concentric to said main housing; said needle shield moveable from a first position wherein said needle is covered, to a second position in which said needle is at least partially exposed, to a third fully extended position in which said needle is irreversibly concealed;
  said generally tubular needle shield comprising a distal end for contacting an injection site, and a proximal end;
 e) a spring urging distal movement of said needle shield; and said needle shield comprising a spring seat;
 f) a needle sheath (NS) remover, designed to mate with and irreversibly grip said needle sheath (NS), for removal of said needle sheath prior to injection;
 g) a locking mechanism for preventing premature advancement of said needle;
  wherein said locking mechanism is constructed such that depressing upon said distal end of said generally tubular needle shield, results in release of said locking mechanism; and said tubular needle shield cannot be depressed prior to removal of said needle sheath (NS), wherein said locking mechanism comprises T-shaped locking arms of said main housing, opposing and pressing on said syringe-support; and release of said locking mechanism comprises lifting of said T-shaped locking arms radially outwards, by proximal movement of said needle shield;
 h) a plunger rod for engaging said piston of said prefilled syringe, wherein the speed of depressing of said plunger is manually controllable by a user;
 wherein in use of said device, said NS remover is grasped and removed; said distal end of said needle shield is brought into contact with and pressed upon an injection site, resulting in release of said locking mechanism, and in drive of said syringe-support and said associated syringe, distally until needle penetration; and upon depressing of said plunger, a medicament may be injected.

2. A safe auto-needle device for injection, comprising:
 a. a main housing;
 b. a syringe-support for receiving a proximal end of a disposable prefilled syringe;
  said disposable prefilled syringe comprises: a piston; a proximal end including a flange; and a distal end terminating in a needle; said needle covered by a needle sheath (NS);

c. a drive mechanism for advancing said syringe-support distally towards an injection site;
d. a generally tubular needle shield concentric to said main housing; said needle shield moveable from a first position wherein said needle is covered, to a second position in which said needle is at least partially exposed, to a third fully extended position in which said needle is irreversibly concealed;
said generally tubular needle shield comprising a distal end for contacting an injection site, and a proximal end;
e. a spring urging distal movement of said needle shield; and said needle shield comprising a spring seat;
f. a needle sheath (NS) remover, designed to mate with and irreversibly grip said needle sheath (NS), for removal of said needle sheath prior to injection;
g. a locking mechanism for preventing premature advancement of said needle; wherein said locking mechanism is constructed such that depressing upon said distal end of said generally tubular needle shield, results in release of said locking mechanism; and said tubular needle shield cannot be depressed prior to removal of said needle sheath (NS);
h. a plunger rod for engaging said piston of said prefilled syringe, wherein the speed of depressing of said plunger is manually controllable by a user;
i. an interlock, for preventing depressing of a plunger, prior to advancement of said syringe-support to a needle penetration location, and said interlock comprises an outwardly facing locking face; and wherein movement of said interlock, and premature pressing of said plunger, are prevented during storage, by engagement of locking face protrusions located upon an anterior plunger pusher, within appropriate grooves of locking faces of a rear cap; and said outwardly facing locking face of said interlock prevents said locking face protrusions from bending inwardly;
wherein in use of said device, said NS remover is grasped and removed; said distal end of said needle shield is brought into contact with and pressed upon an injection site, resulting in release of said locking mechanism, and in drive of said syringe-support and said associated syringe, distally until needle penetration; and upon depressing of said plunger, a medicament may be injected.

3. The device of claim 2, wherein said drive mechanism (c) comprises a compressed spring and a spring seat, for urging said syringe-support distally towards said injection site.

4. The device of claim 2, wherein said plunger rod comprises at least one locking tab to prevent pulling of said plunger rod in the proximal direction, instead of pressing of said plunger rod.

5. The device of claim 4, further comprising a rear cap having a hollow center through which said plunger rod enters, and an internal lock bracket, said lock bracket interacting with said locking tab of said plunger to prevent pulling of said plunger, ensuring unidirectional movement of said plunger.

6. The device of claim 2, comprising a locking mechanism for locking said needle shield after injection, in said third fully extended position, fully covering a needle tip.

7. The device of claim 6, wherein said needle shield locking mechanism comprises: lower locking arms present upon said main housing, which hold said needle shield in a fully extended position covering said needle, after use.

8. The device of claim 2, comprising a transparent viewing window on said main housing, allowing viewing of the state of a medicament present in a prefilled syringe held in said device when said tubular needle shield is in said first position.

9. The device of claim 2, wherein a terminal distal end of said NS remover comprises bumpers to receive and dampen axial load applied to said NS remover when said device is dropped; thereby preventing breakage of a prefilled syringe.

10. The device of claim 2, wherein said NS remover is comprised of an inner tubular portion comprising snap teeth for mating with an NS, and an outer concentric tubular portion comprising a grip face; and flexible connection arms connect said inner and outer portions.

11. The device of claim 2, wherein release of said interlock is performed by distal movement of said syringe-support, by said drive mechanism; resulting in distal movement of said interlock's locking face from its previous position opposite said locking face protrusions of said anterior plunger pusher; said protrusions are free to bend inwardly and disengage from said internal grooved locking faces of said rear cap; allowing said anterior plunger pusher to be pressed by a user.

12. The device of claim 2, wherein said plunger rod is a tri-component plunger having one-way ratchet teeth.

13. The device of claim 12, wherein said tri-component plunger comprises: an anterior plunger pusher; and a proximal plunger having angled one-way ratchet teeth, which may engage appropriate one-way ratchet teeth upon a distal plunger; and said proximal plunger comprises in an internal face a storage area in which said ratchet teeth are disengaged prior to use of said device, said storage area allowing movement of said distal plunger due to internal air pressure in a syringe.

14. The device of claim 13, wherein said tri-component plunger, advantageously does not prevent movement of said syringe-support for needle penetration, when a user forcefully grasps the anterior plunger pusher during use.

15. The device of claim 2, wherein said NS remover is comprised of:
an internal part for mating with said NS;
and an external part for transferring impact forces upon dropping of said device, to a stopper on said main housing;
and ratchet teeth are present on one of: said internal part, and said external part; for engaging flexible teeth upon the other of: said external part and internal part; said ratchet teeth allowing tolerance in position of said NS during storage.

16. The device of claim 15, wherein said NS remover internal part is guided axially on said needle shield thus preventing a bending load on the needle.

17. The device of claim 2, wherein said locking mechanism (g) comprises locking arms present on said syringe-support; said locking arms entering stop windows on said main housing; and wherein in release of said locking mechanism, activation slopes located at the terminal end of said locking arms slide against activation slopes of said proximally moving needle shield; thereby bending said locking arms inward and removing said locking arms from said stop windows.

18. The device of claim 2, wherein said interlock is structured to block pressing of said plunger until said syringe-support has advanced distally to a needle penetration position; thus preventing user error of premature discharge of a medicament.

19. The device of claim 18, wherein said plunger comprises a plurality of locking teeth present upon the length of said plunger;

and said interlock comprises a pivot hinge, and a flexible load beam for urging pivoting of said interlock on said hinge upon user initiation of an injection;

and said interlock terminates in at least one locking tooth designed to engage one or more of said locking teeth present upon said plunger, said engagement preventing said plunger from being pressed; and said engagement occurring prior to needle penetration.

20. The device of claim 19, wherein said interlock locking tooth is designed to engage said at least one plunger locking tooth, after use of said device.

21. The device of claim 19, wherein said interlock comprises one or more guiding holes designed to mate with and accept therein, one or more lengthened release fingers present upon said syringe-support; said mating preventing said at least one locking tooth of said interlock from disengaging from said locking teeth of said plunger; wherein distal advancement of said syringe-support towards an injection site results in removal of said one or more lengthened release fingers from within said one or more guiding holes.

22. The device of claim 2, comprising a plunger one-way ratchet system for preventing pulling of said plunger proximally and allowing only pressing of a plunger distally.

23. The device of claim 22, wherein said plunger is a two component plunger comprised of a proximal plunger component and a distal plunger component; each of said plunger components having at least one ratchet tooth allowing mating of said two plunger components during pressing of a plunger; and said plunger components have a pre-engagement positioning, allowing said components to slide upon one another allowing for tolerance in axial positioning, prior to pressing of said plunger.

24. The device of claim 3, wherein said interlock is additionally structured to block movement said plunger after use of said device.

25. The device of claim 24, wherein said interlock comprises two terminal locking teeth angled in opposing directions and engaging appropriately angled locking teeth, present upon the length of said plunger.

26. The device of claim 2, comprising a plurality of longitudinal ribs located internally within said needle shield, said ribs providing axial support for said prefilled syringe.

27. An NS remover, for use with an injection device comprising a syringe, a needle and a needle sheath; said NS remover comprising:

an internal part for mating with said needle sheath (NS);

and an external part for transferring impact forces upon dropping of said injection device, to a stopper on a main housing of said injection device;

and ratchet teeth are present on one of said internal part and said external part, for engaging flexible teeth upon said other of said external part and said internal part; said ratchet teeth allowing tolerance in position of said needle sheath (NS) during storage.

* * * * *